United States Patent
Mahboobi et al.

(10) Patent No.: US 11,384,076 B2
(45) Date of Patent: Jul. 12, 2022

(54) SYNTHESIS, PHARMACOLOGY AND USE OF NEW AND SELECTIVE FMS-LIKE TYROSINE KINASE 3 (FLT3) FLT3 INHIBITORS

(71) Applicants: UNIVERSITÄT REGENSBURG, Regensburg (DE); UNIVERSITÄTSMEDIZIN DER JOHANNES GUTENBERG-UNIVERSITÄT MAINZ, Mainz (DE)

(72) Inventors: Siavosh Mahboobi, Regensburg (DE); Andreas Sellmer, Lappersdorf (DE); Herwig Pongratz, Regensburg (DE); Bernardette Pilsl, Wenzenbach (DE); Oliver Krämer, Nackenheim (DE); Thomas Kindler, Mainz (DE); Mandy Beyer, Wiesbaden (DE)

(73) Assignees: UNIVERSITÄT REGENSBURG, Regensburg (DE); UNIVERSITÄTSMEDIZIN DER JOHANNES GUTENBERG-UNIVERSITÄT MAINZ, Mainz (DE)

( * ) Notice: Subject to any disclaimer, the term of this patent is extended or adjusted under 35 U.S.C. 154(b) by 73 days.

(21) Appl. No.: 16/639,964

(22) PCT Filed: Aug. 9, 2018

(86) PCT No.: PCT/EP2018/071676
§ 371 (c)(1),
(2) Date: Feb. 18, 2020

(87) PCT Pub. No.: WO2019/034538
PCT Pub. Date: Feb. 21, 2019

(65) Prior Publication Data
US 2020/0190075 A1    Jun. 18, 2020

(30) Foreign Application Priority Data
Aug. 18, 2017    (EP) .................................. 17186903

(51) Int. Cl.
C07D 413/14    (2006.01)
A61P 35/02    (2006.01)

(52) U.S. Cl.
CPC ............ *C07D 413/14* (2013.01); *A61P 35/02* (2018.01)

(58) Field of Classification Search
CPC ............................... C07D 413/14; A61P 35/02
See application file for complete search history.

(56) References Cited

FOREIGN PATENT DOCUMENTS

WO    2007053343 A2    5/2007
WO    2010124648 A1    11/2010

OTHER PUBLICATIONS

Mahboobi, S. et al., "Inhibition of FLT3 and PDGFR tyrosine kinase activity by bis(benzo[b]furan-2-yl)methanones" Bioorganic & Medicinal Chemistry, Jan. 31, 2007, vol. 15, No. 5, pp. 2187-2197.
Chao, Q. et al., "Identification of N-(5-tert-Butyl-isoxazol-3-yl-N'-{4-[7-(2-morpholin-4-yl-ethoxy)imidazo-[2,1-b][1,3] benzothiazol-2-yl]phenyl}urea Dihydrochloride (AC220), a Uniquely Potent, Selective, and Efficacious FMS-Like Tyrosine Kinase-3 (FLT3) Inhibitor" J. Med. Chem., Dec. 10, 2009, vol. 52, pp. 7808-7816.

*Primary Examiner* — Samira J Jean-Louis
(74) *Attorney, Agent, or Firm* — Saliwanchik, Lloyd & Eisenschenk

(57) ABSTRACT

The present invention relates to small molecule compounds of formula (I) and their use as FLT3 inhibitors for the treatment of various diseases, such as acute myeloid leukemia (AML). The present invention further relates to methods of synthesizing the compounds and methods of treatment.

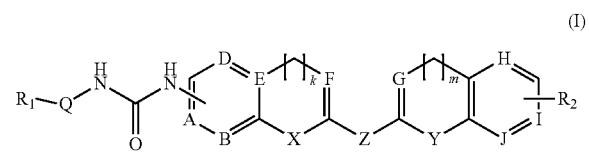

(I)

22 Claims, 15 Drawing Sheets

Fig. 6
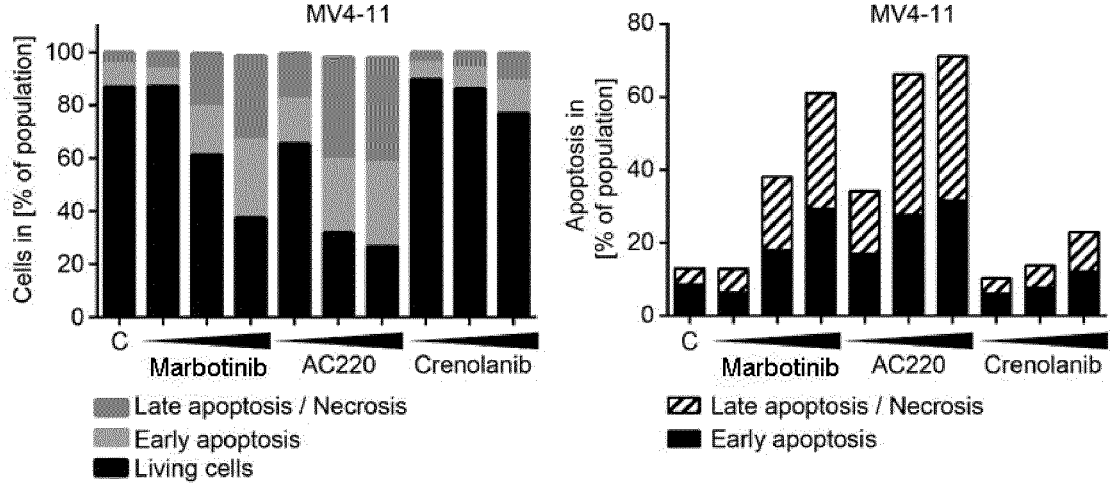
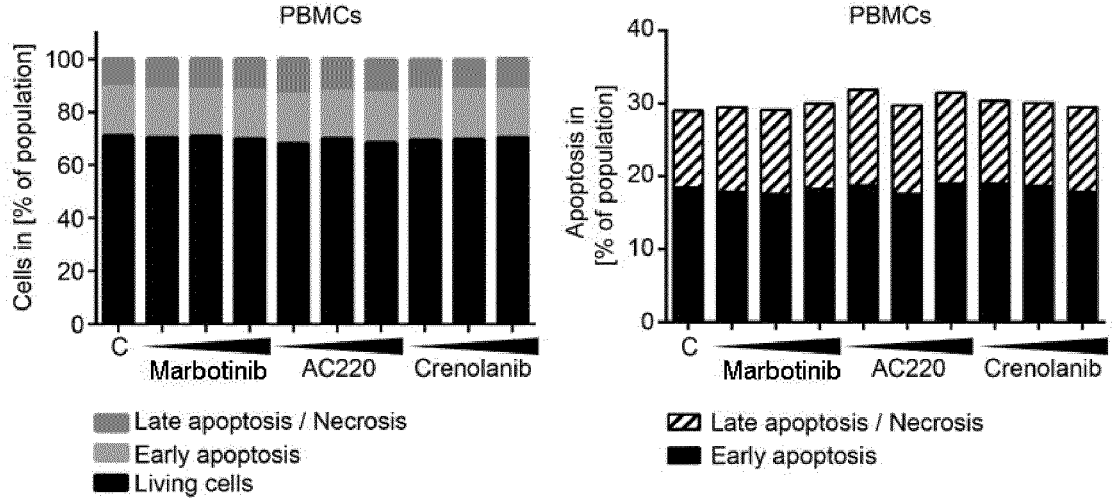

Fig. 7.1
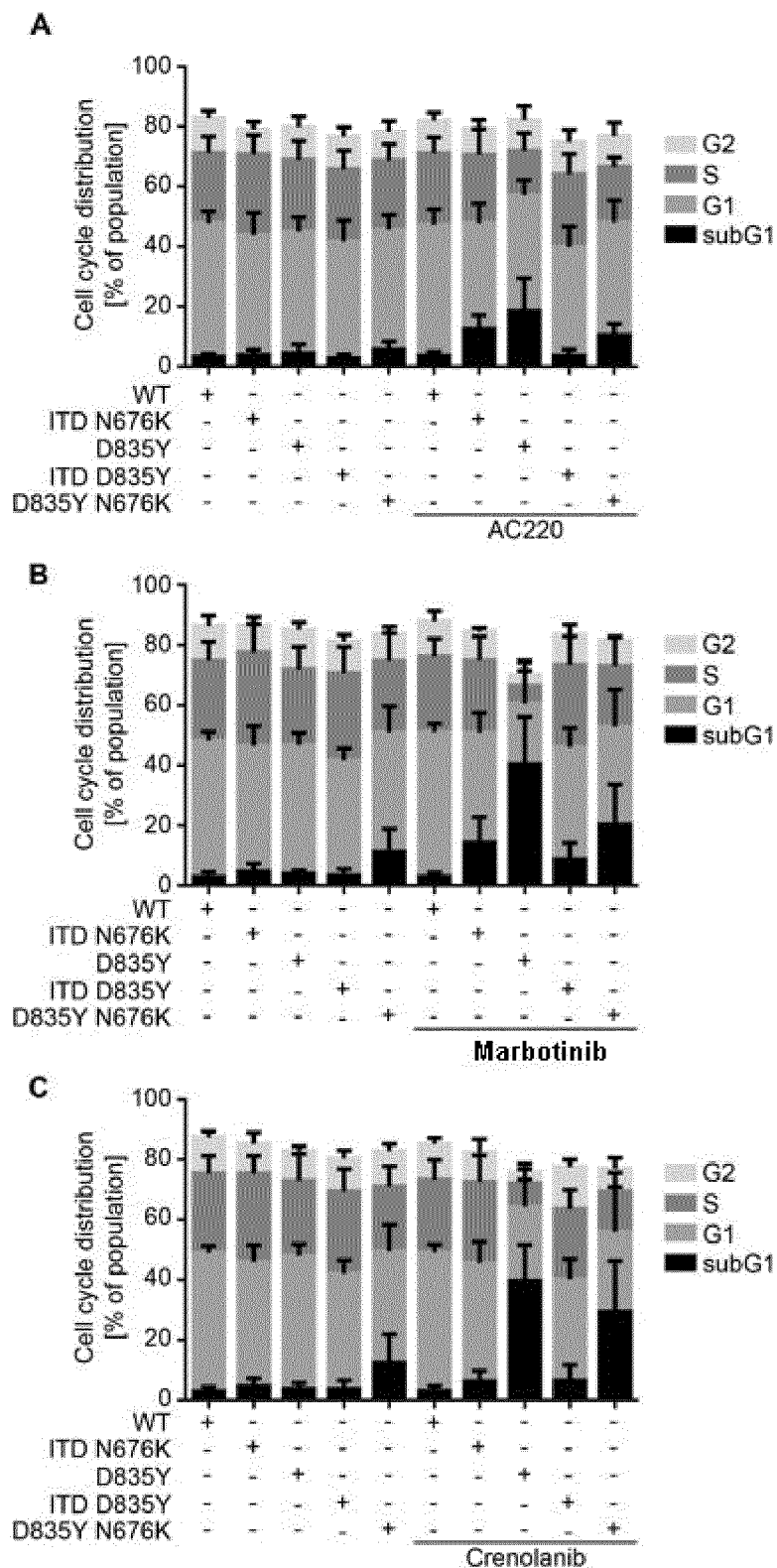

Fig. 7.2
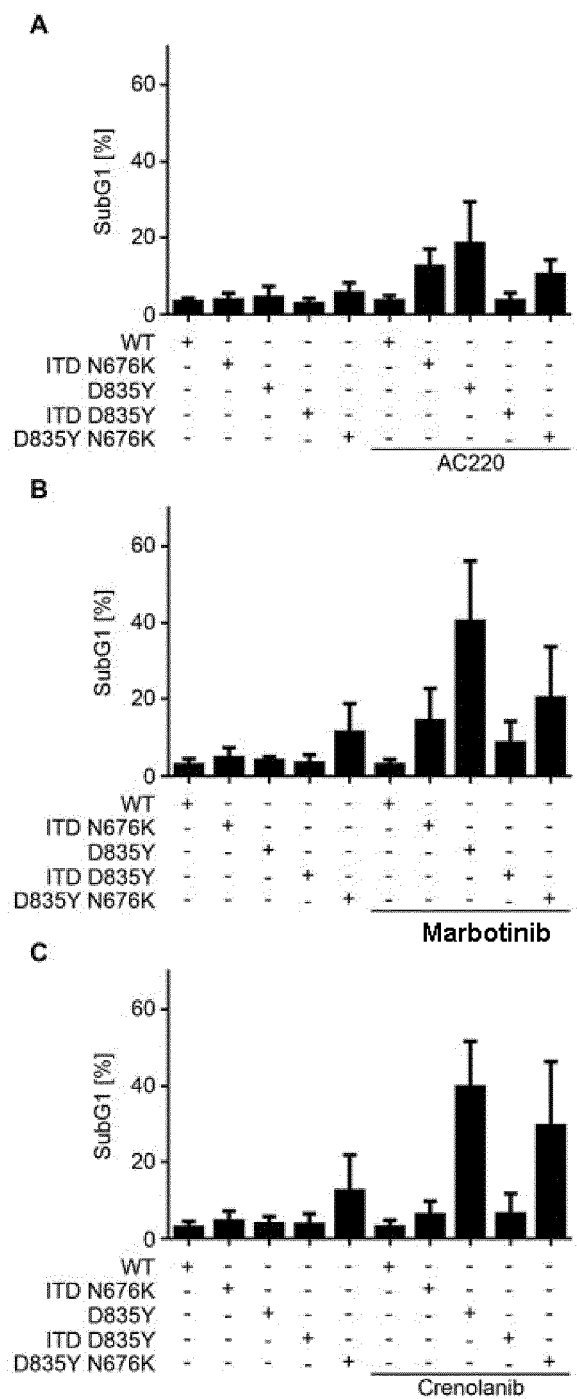

SYNTHESIS, PHARMACOLOGY AND USE OF NEW AND SELECTIVE FMS-LIKE TYROSINE KINASE 3 (FLT3) FLT3 INHIBITORS

CROSS REFERENCE TO RELATED APPLICATIONS

This application is a National Stage Application of International Application Number PCT/EP2018/071676, filed Aug. 9, 2018; which claims priority to European Application No. 17186903.5, filed Aug. 18, 2017.

The present invention relates to small molecule compounds and their use as FLT3 inhibitors for the treatment of various diseases, such as acute myeloid leukemia (AML). The present invention further relates to methods of synthesizing the compounds and methods of treatment.

BACKGROUND OF THE INVENTION

The class III receptor tyrosine kinases (RTK) are required for normal hematopoiesis and they are frequently dysregulated in AML (Berenstein 2015). Therefore, RTK are targets for tailored intervention strategies against AML. Enzymes belonging to this protein family are FMS-like tyrosine kinase 3 (FLT3), macrophage colony stimulating factor receptor (CSF1R, c-FMS), stem cell factor receptor (SCFR, KIT), and platelet-derived growth factor receptor (PDGFRα/β) (Xu, Ong et al. 2014). Each of these factors consists of five immunoglobuline-like domains in the extracellular domain, a transmembrane domain (TMD), a juxtamembrane domain (JM), and two intracellular kinase domains, divided by a kinase insert domain (Small, Levenstein et al. 1994; Lyman 1995; Meshinchi and Appelbaum 2009).

FLT3 is expressed on hematopoietic stem and progenitor cells and plays an indispensable role in stem cell development and cell differentiation (Gilliland and Griffin 2002). FLT3 is activated upon the binding of its ligand. After the ligand-induced dimerization and autophosphorylation of the receptor, the signal transduction pathway is initiated (Heldin 1995). Mutations in FLT3 can be found in about one-third of all patients with AML and such aberrations are associated with poor prognosis (Nakao, Yokota et al. 1996; Yamamoto, Kiyoi, et al. 2001; Gilliland and Griffin 2002). These lesions cause an aberrant activation of FLT3 and its downstream signaling pathway (Mahboobi, Teller et al. 2002; Kayser and Levis 2014). Of note, recent evidence shows that mutant FLT3 is an oncogenic driver in AML (Smith, Wang et al. 2012). Different activating FLT3 mutations are known. 1) Activating FLT3 internal tandem duplications (FLT3-ITD) locate within the JM domain of FLT3. These were first observed in 1996 by Nakao et al. (Nakao, Yokota et al. 1996) and are seen in 15-35% of the patients suffering from AML (Nakao, Yokota et al. 1996; Yokota, Kiyoi et al. 1997; Frohling, Schlenk et al. 2002; Schenone, Brullo et al. 2008; Kayser and Levis 2014). Point mutations in the activation loop of the kinase domain (FLT3-KD) occur in 6-8% of patients with AML (Abu-Duhier, Goodeve et al. 2001; Yamamoto, Kiyoi, et al. 2001; Reindl, Bagrintseva, et al. 2006; Kayser and Levis 2014). Point mutations in the JM are detectable in 2% of AML patients (Reindl, Bagrintseva et al. 2006; Kayser and Levis 2014). The most common of these mutations, FLT3-ITD, induces the loss of the auto-inhibitory functions whereby the kinase becomes constitutively active. This leads to altered intracellular signaling (Schmidt-Arras, Bohmer et al. 2009) and autonomous cell growth (Kayser and Levis 2014).

Due to the frequency of FLT3 mutations in AML, the inhibition of FLT3 and its downstream signaling pathways have logically attracted significant attention in the discovery of new anti-cancer drugs (Konig and Santos 2015). Most of the potential therapeutics currently under development are direct inhibitors of the FLT3 receptor. Such small molecule inhibitors are investigated in monotherapy or in combination with chemotherapy (Kindler, Lipka et al. 2010; Fathi and Levis 2011; Grunwald and Levis 2015; Konig and Santos 2015). Inhibitors of FLT3 are classified into the first and the second generation and are shown in FIG. 1, infra. The first generation of small molecule inhibitors include midostaurin 1 (PKC412) (Kindler, Lipka et al. 2010), lestaurtinib 2 (CEP-701) (Smith, Levis et al. 2004; Knapper, Burnett et al. 2006; Kindler, Lipka et al. 2010), semxanib 3 (SU 5416) (Giles, Stopeck et al. 2003; Kindler, Lipka et al. 2010) and sunitinib 4 (SU 11248) (Kindler, Lipka et al. 2010). They are generally multi-kinase inhibitors and their efficacies are limited, not durable, and at the expense of undesired side effects (Fathi and Levis 2011; Leung, Man et al. 2013).

Therefore, a second generation of TKi against FLT3-ITD has been developed to yield more selective and highly potent agents for treating AML and to overcome resistance (Ustun, DeRemer et al. 2009; Lin, Hsu et al. 2013). Prominent representatives for the second generation are tandutinib 5 (MLN518) (Schittenhelm, Kampa et al. 2009; Fathi and Levis 2011) KW-2449 6 (Pratz, Cortes et al. 2009; Fathi and Levis 2011) and quizartinib 7 (AC 220) (Chao, Sprankle et al. 2009; Kindler, Lipka et al. 2010; Fathi and Levis 2011).

During therapy with FLT3 TKIs it becomes apparent that a significant proportion of a secondary FLT3-TKD mutation emerges (Smith, Wang et al. 2012), and this positions FLT3-ITD as a driver of leukemogenesis (Kindler, Lipka et al. 2010). Mutations in position D835 within the activation loop (Lee, Kim et al. 2014), the gatekeeper F691 (Zimmerman, Turner et al. 2013), or N676 have independently been confirmed to cause a reduction or a loss of response to FLT3 TKi (Kindler, Lipka et al. 2010). Mutations at the activation loop residue D835 stabilize an enzymatically active kinase conformation which cannot accommodate type II FLT3 inhibitors (i.e. such mutations fix the Asp-Phe-Gly motif in the so-called DFG-in conformation (Lewis, Lewis et al. 2009; Smith, Lin et al. 2015)), and gatekeeper mutations impair the binding of AC220 (7) (FIG. 1) (Smith, Shah et al. 2015). These type II FLT3 TKi appear to bind only to the so-called DFG-out conformation of the inactive kinase (Smith, Lasater et al. 2014; Smith, Lin et al. 2015); type I inhibitors bind the ATP binding site and adjacent residues (Liu and Gray 2006)). Especially bulky hydrophobic substitutions (D→Y/V/I/F) at D835 disrupt the interaction of this site with S838 within FLT3-ITD and thereby confer resistance to AC220 and other type II FLT3 TKi (Smith, Lin et al. 2015).

Intense efforts have yielded compounds that also target FLT3-ITD with mutations in its activation loop. Examples are crenolanib 8 (Abu-Duhier, Goodeve et al. 2001; Zimmerman, Turner et al. 2013; Galanis, Ma et al. 2014; Smith, Lasater et al. 2014), G-749 9 (Lee, Kim et al. 2014), TTT-3002 10, as well as dual kinase inhibitors (e.g., CCT137690 11, against FLT3 and Aurora kinase (Moore, Faisal et al. 2012)). The benzamidine quinolone crenolanib 8, which was originally developed as PDGFR inhibitor (Lewis, Lewis et al. 2009), is currently the best described FLT3 TKi against therapy-associated FLT3-ITD mutants.

Independent groups have shown that crenolanib 8 exerts type I TKi properties against FLT3-ITD and mutants thereof (Zimmerman, Turner et al. 2013; Galanis, Ma et al. 2014; Smith, Lasater et al. 2014), i.e. the ability to target kinases in the active, DFG-in conformation (Liu and Gray 2006). Crenolanib 8 shows activity against wild-type FLT3-ITD and FLT3-ITD with secondary KD mutations at D835 or F691 in vitro and in vivo.

Although type I TKi often fail to exert inhibitor specificity (Liu and Gray 2006), crenolanib 8 inhibits FLT3-ITD and its KD mutants about 100-fold more potently than KIT (Smith, Lasater et al. 2014). The latter is important because a combined knock-out of FLT3 and KIT is detrimental for normal hematopoiesis, and because the potent inhibition of FLT3 plus KIT by AC220 7 caused severe myelosuppression in leukemic patients (Smith, Lasater et al. 2014).

Crenolanib 8 delayed the outgrowth of MV4-11 cells in a xenograft mouse model and only by combination with the type II TKI sorafenib 12, a significant decrease in leukemic burden and prolonged survival was observed compared with either type I or II TKI alone (Zimmerman, Turner et al. 2013).

Further, the combination of FLT3 inhibitors with other active principles forms another inventive concept of the use of activated FLT3 versions as therapeutically relevant target structures. Promising combinations comprise the herein disclosed FLT3 inhibitors with histone deacetylase inhibitors (HDACi). The synergism of inhibition of tyrosine kinases and histone deacetylases has previously been shown (Pietschmann et al., Mol Cancer Ther. 2012 November; 11(11):2373-83) and was described for FLT3 (Mahboobi, Siavosh; et al., Journal of Medicinal Chemistry (2009), 52(8), 2265-2279).

Taken together, AC220-resistant FLT3 kinase domain mutants represent high-value targets for future FLT3 inhibitor development efforts (Smith, Wang et al. 2012).

Accordingly, there is a need in the art for improved FLT3 inhibitors.

This objective is solved by provision and the use of compounds according to the invention, which act as FLT3 inhibitors.

The compounds according to the invention can be used in pharmaceutical compositions or generally in medicine.

More precisely, the above objective is solved by compounds according to the invention or pharmaceutical composition of the present invention for use in the treatment of cancer, such as acute myeloid leukemia (AML).

DESCRIPTION OF THE FIGURES

FIG. 6: MV4-11 cells and PBMCs were treated with Marbotinib, AC220 or Crenolanib in different dosis (2 nM, 5 nM and 10 nM) for 24 h and stained with AnnexinV FITC/PI and analyzed by flow cytometry. Illustrated are the different populations of living cells, early apoptosis and late apoptosis/necrosis. To elucidate the apoptotic effects the population of cells in early apoptosis and late apoptosis/necrosis is represented in a separate diagram. A) MV4-11 cell line; B) PBMCs; n=1

FIG. 7.1: Murine Ba/F3 WT vs. mutant cells were treated with different doses Marbotinib in comparison to AC220 and Crenolanib (2 nM, 5 nM and 10 nM) for 48 h. Cells were stained with PI; cell cycle was analyzed by flow cytometry. (n=3) A) AC220; B) Marbotinib; C) Crenolanib FIG. 7.2: To elucidate an increase of apoptosis, subG1 fraction is represented in a separate diagram from FIG. 7.1. SubG1 population of Ba/F3 WT and mutants are treated with A) 5 nM AC220, B) 5 nM Marbotinib or C) 5 nM Crenolanib for 48 h is illustrated. (n=3)

SUMMARY OF THE INVENTION

Figure 1:
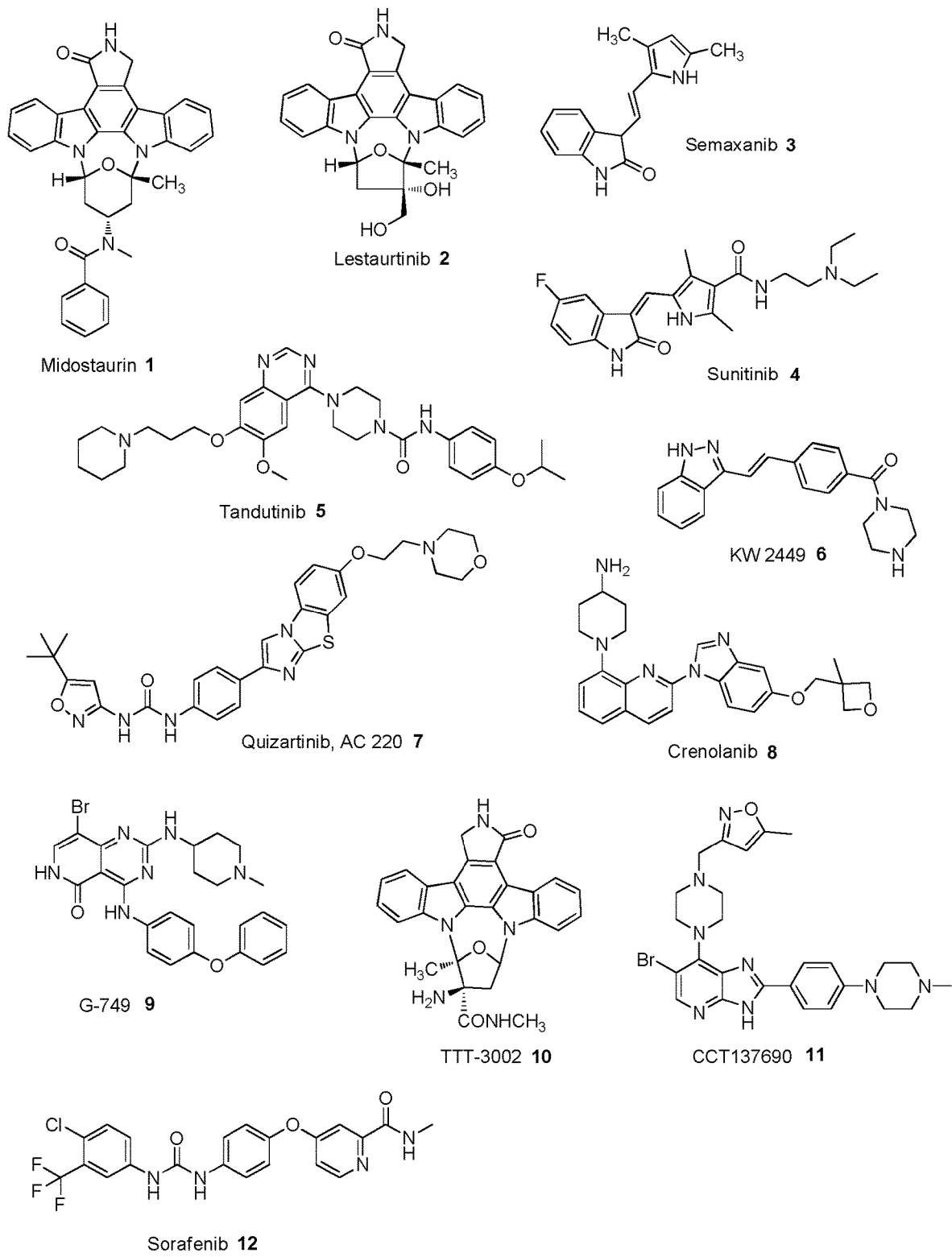
FIG. 1: Overview of FLT3 inhibitors investigated for treatment of AML (1-12).

Subject-matter of the present invention solving the above-mentioned problems is/are a compound(s) having the general formula I:

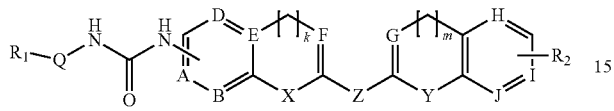

wherein

A, B, D, E, F, G, H, I and J are independently from each other CH or N, k and m are independently from each other 0 or 1, X and Y are independently from each other NH, O or S, Z is C=O, C=S or CHOH (preferably C=O), Q is a five or six membered aromatic or heteroaromatic system (preferably isoxazole), $R_1$ is selected from the group comprising H, alkyl, branched or unbranched (preferably tert-Butyl), and $R_2$ is selected from the group comprising H, alkyl residues, OH (preferably OH), an ester, a carbamate, alkoxy, alkoxy or an ester or a carbamate substituted with a group comprising amino, alkylamino, cylic alkylamino, cyclic diaminoalkyl as piperazinyl or 1-methylpiperazinyl, heterocyclic alkylamino as morpholinyl; 2-hydroxysuccinic acid, an amino acid, especially a basic amino acid such as lysine, proline, histidine or arginine and pharmaceutically acceptable salts thereof. Salts thereof comprise hydrochlorides, sulfates, phosphates, mesylates, tosylates, formiates or acetates as examples, but are not limited to these. Examples for $R_2$ with n=0-6 are shown below.

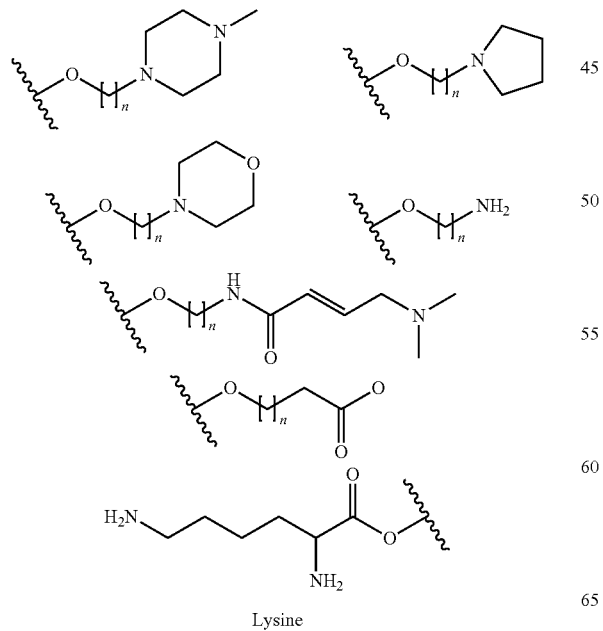

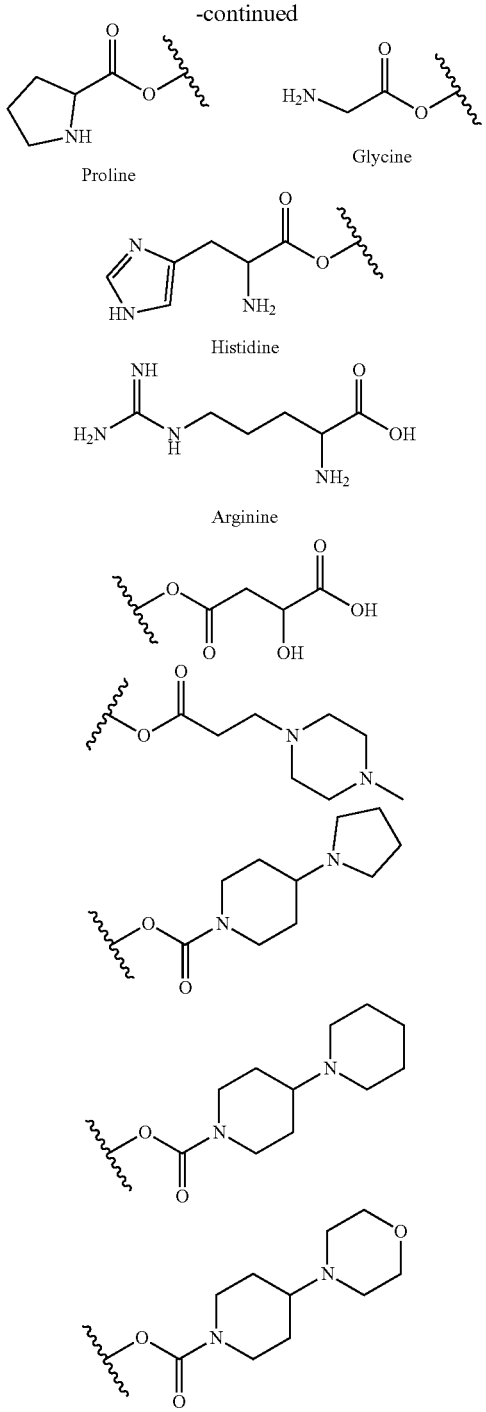

Subject-matter of the present invention is also a pharmaceutical composition comprising (a) at least one compound according to the invention, (b) optionally, a further active agent or drug, (c) optionally, pharmaceutically acceptable excipient(s) and/or carrier.

According to the present invention the inventive compounds act as FLT3 inhibitors.

Subject-matter of the present invention is/are also (a) compound(s) referred to above or pharmaceutical composition comprising the same for use in medicine.

Subject matter of the present invention are also compounds according to the invention referred to herein or pharmaceutical composition of the present invention as disclosed herein for use in the treatment of cancer, such as leukemia, especially such as acute myeloid leukemia (AML).

In the following disclosure, embodiments of the present invention are described and explanations of various terms are provided. Whenever a given embodiment refers back to one of more preceding embodiments, the wording describing the subject matter of such preceding embodiments shall be considered repeated. Combinations of alternatives referred to in one or more given embodiments are explicitly contemplated unless, for obvious technical reasons, a person skilled in the art would have excluded such combination or combinations.

In more detail, subject-matter of the invention is, e.g., a compound of formula II:

(II)

$$R_1-Q-\overset{H}{N}-\underset{O}{\overset{}{C}}-\overset{H}{N}-\text{[ring A/B/X]}-Z-Y-\text{[indole with }R_2\text{]}$$

wherein

A and B are independently from each other selected from the group comprising CH or N, X and Y are independently from each other selected from the group comprising NH, O or S, Z is selected from the group comprising C=O, C=S or CHOH, Q is selected from the group comprising five or six membered aromatic or heteroaromatic systems, $R_1$ is selected from the group comprising H, alkyl, branched or unbranched, and $R_2$ is selected from the group comprising H, alkyl residues, OH, an ester, a carbamate, alkoxy, alkoxy or an ester or a carbamate substituted with a group comprising amino, alkylamino, cyclic alkylamino, cyclic diaminoalkyl (such as piperazinyl or 1-methylpiperazinyl), heterocyclic alkylamino as morpholinyl; 2-hydroxysuccinic acid, an amino acid, and pharmaceutically acceptable salts or solvates thereof.

Subject-matter of the invention is also a compound according to the preceding embodiment, wherein Q is isoxazole, or a salt or solvate thereof.

Subject-matter of the invention is also a compound according to any one of the preceding embodiments, wherein $R_1$ is tert-Butyl, or a salt or solvate thereof.

Subject-matter of the invention is also a compound according to any one of the preceding embodiments, wherein $R_2$ is OH or an amino acid, or a salt or solvate thereof.

Subject-matter of the invention is also a compound according to any one of the preceding embodiments, wherein X is O, or a salt or solvate thereof.

Subject-matter of the invention is also a compound according to any one of the preceding embodiments, wherein Y is NH, or a salt or solvate thereof.

Subject-matter of the invention is also a compound according to any one of the preceding embodiments, wherein Z is C=O, or a salt or solvate thereof.

Subject-matter of the invention is also a compound according to any one of the preceding embodiments, wherein A is CH, or a salt or solvate thereof.

Subject-matter of the invention is also a compound according to any one of the preceding embodiments, wherein B is CH, or a salt or solvate thereof.

Subject-matter of the invention is also a compound according to any one of the preceding embodiments having formula III (III)

$$\text{tert-butyl-isoxazole}-\overset{H}{N}-\underset{O}{\overset{}{C}}-\overset{H}{N}-\text{benzofuran}-C(=O)-\text{indole-OH}$$

or a salt or solvate thereof.

Subject-matter of the present invention is also a compound according to formula (III), wherein the phenolic OH group is modified into a carbamate, i.e. a carbamate derivative of formula (III), or a salt or solvate of such carbamate derivative. An example of such carbamate derivative is compound 48a or 48b, as shown further below, e.g. in Scheme 10.

Subject-matter of the invention is also a compound according to any one of the preceding embodiments, wherein the salt is selected from the group of salts comprising hydrochloride, sulfate, phosphate, mesylate, tosylate, formiate, and acetate or in case of $R_2$=OH a salt of the respective phenolate comprising sodium, potassium, calcium, zinc or another suitable kation and its solvates.

Subject-matter of the invention is also a pharmaceutical composition comprising a compound of formulae (I), (II) and/or (III) as defined in any one of the preceding embodiments. It is possible to provide pharmaceutical compositions that comprise more than one alternative falling under the definitions for formulae (I), (II) and/or (III).

Subject-matter of the invention is also a compound according to any one of the preceding embodiments or a pharmaceutical composition according to the preceding embodiment for use in the treatment of cancer.

Subject-matter of the invention is also a compound according to any one of the preceding embodiments or a pharmaceutical composition according to the preceding embodiments for use in the treatment of blood cancer.

Subject-matter of the invention is also a compound according to any one of the preceding embodiments or a pharmaceutical composition according to the preceding embodiments for use in the treatment to AML.

Subject-matter of the invention is also a compound according to any one of the preceding embodiments or a pharmaceutical composition according to the preceding embodiments for use in the treatment of a cancer patient having a mutation in the Flt3 gene.

Subject-matter of the invention is also a compound according to any one of the preceding embodiments or a pharmaceutical composition according to the preceding embodiments for use in the treatment of cancer in a patient that is subjected to treatment with at least one further drug, particularly with at least one anti-cancer drug, more preferably with at least one pan- or isoform selective HDAC inhibitor, wherein said HDAc inhibitor may be selected from the group comprising Suberoylanilid Hydroxamic Acid (SAHA, Vorinostat), Panobinostat (LBH589)) und Benzamide (z.B. MS-275, MGCD-0103). Other combinations comprise co-treatments with transcription inhibitors known in the art. In certain embodiments the transcription inhibitor is a cyclin dependent kinase (CDK) inhibitor as a CDK1, CDK2, CDK3, CDK4, CDK5, CDK6, CDK7, CDK8, CDK9, CDK19, CDK11 or CDK12 inhibitor. In certain embodiments, the CDK inhibitor is THZ1, E9, YLK-01-116, THZ-5-31-1, Dinaciclip, DCA or palbociclib. In certain embodiments, the transcription inhibitor is a bromodomain-containing protein inhibitor (e.g. BRD2, BRD3, BDR4), a CREB binding protein inhibitor or a E1A binding protein p300 (EP300) inhibitor.

Subject-matter of the invention is also a compound according to any one of the preceding embodiments or a pharmaceutical composition according to the preceding embodiments for use in the inhibition of FLT3.

Subject-matter of the invention is also a method of treatment of an individual in need thereof and/or the amelioration of and/or the prevention of deterioration of a disease in an individual in need thereof, e.g., in a patient having a cancer as defined in any one of the preceding embodiments, by administration to said individual of a therapeutically efficient amount of any of the compounds and/or salts or and/or solvates thereof and/or pharmaceutical compositions as defined above.

Subject matter of the present invention is also the use of a compound as defined above, for the manufacture of a medicament for the treatment of cancer, as defined above.

As discussed above, the invention provides a compound having the general formula (II)

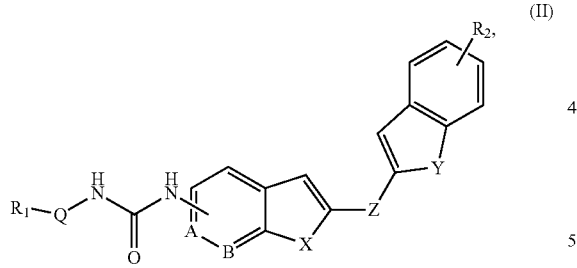

(II)

wherein
A and B are independently from each other CH or N,
X and Y are independently from each other NH, O or S
Z is C=O, C=S or CHOH (preferably C=O)
Q is a five or six membered aromatic or hetroaromatic system (preferably isoxazole)
$R_1$ is selected from the group comprising H, alkyl, branched or unbranched (preferably tert-Butyl) and
$R_2$ is selected from the group comprising H, alkyl residues, OH (preferably OH), an ester, a carbamate, alkoxy, alkoxy or an ester or a carbamate substituted with a group comprising amino, alkylamino, cylic alkylamino, cyclic diaminoalkyl as piperazine or 1-methylpiperazine, heterocyclic alkylamino as morpholine; 2-hydroxysuccinic acid, aminoacids, especially basic amino acids as lysine, proline, histidine or arginine and pharmaceutically acceptable salts thereof. Salts thereof comprise hydrochlorides, sulfates, phosphates, mesylates, tosylates, formiates or acetates or in case of $R_2$=OH a salt of the respective phenolate comprising sodium, potassium, calcium, zinc and its solvates as examples, but are not limited to these.

Some of the preferred embodiments of the compound according to formula (I) have been discussed above.

Examples for $R_2$ with n=0-6 are shown below.

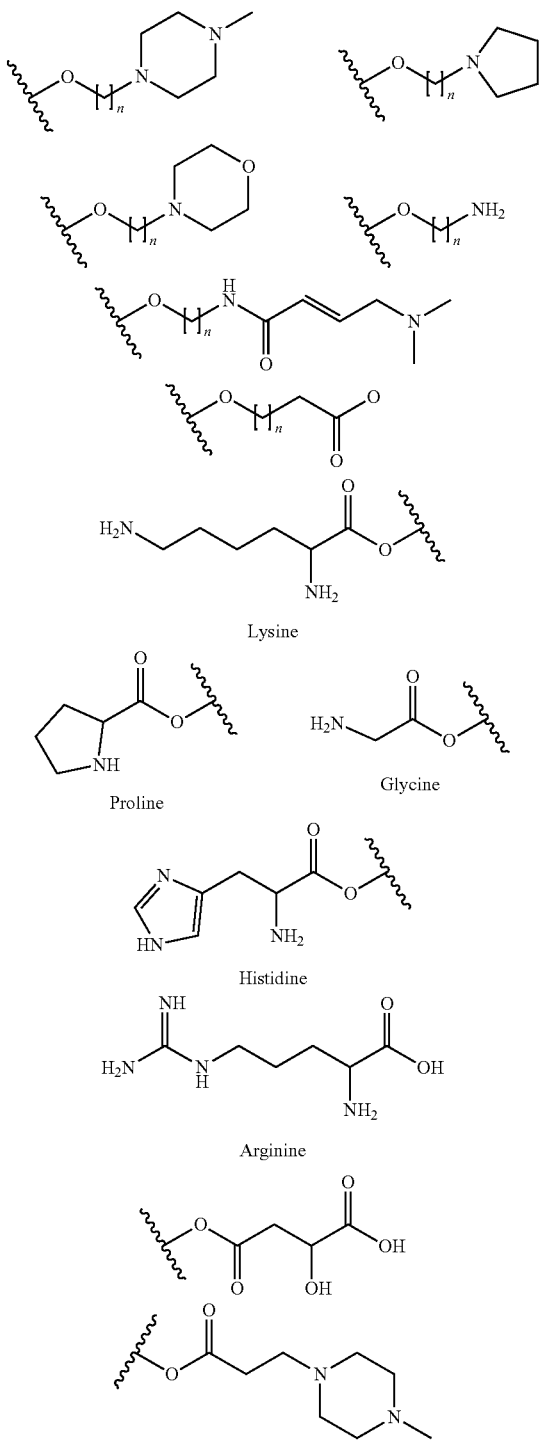

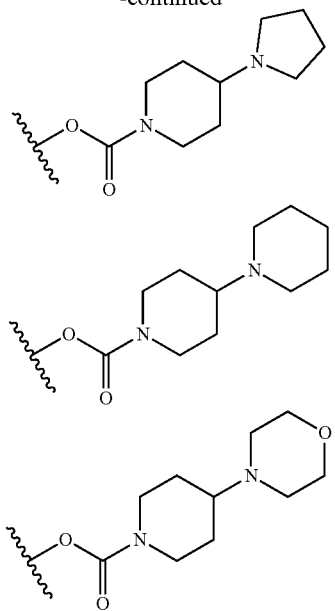

The compounds of the present invention are novel tyrosine kinase inhibitors, in particular FLT3 inhibitors. In one embodiment, the compound of the present invention has the general formula (I).

In a preferred embodiment the inventive compound has the general formula (IV)

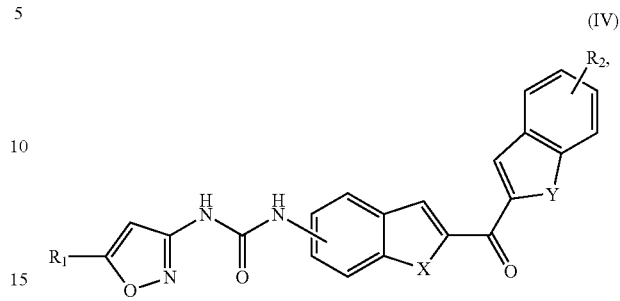

(IV)

wherein X and Y are independently from each other NH, O or S, and wherein $R_1$ and $R_2$ are as defined above.

In further embodiments, the compound(s) of the present invention is/are selected from the compound depicted in the following Table 1. Each of the compounds may be used as defined above, and/or may be at least one active ingredient in pharmaceutical compositions or formulations described above, which can be used in the methods of treatment or are for use in the treatment of cancer as detailed herein.

TABLE 1

1-(5-(tert-Butyl)isoxazol-3-yl)-3-(2-(5-hydroxy-1H-indole-2-carbonyl)benzofuran-5-yl)urea (28) (Marbotinib)

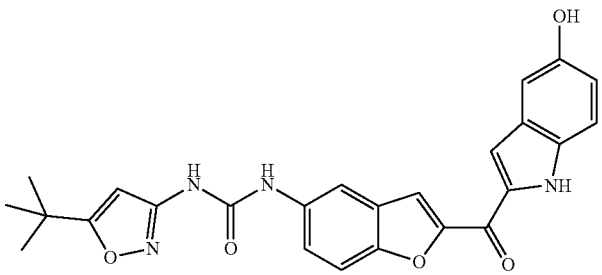 [SMILES: CC(C)(C)c1cc(NC(=O)Nc2ccc3oc(C(=O)c4cc5cc(O)ccc5[nH]4)cc3c2)no1]

1-(5-(tert-butyl)isoxazol-3-yl)-3-(2-(4-methyl-1H-indole-2-carbonyl)-1H-indol-4-yl)urea (36a):

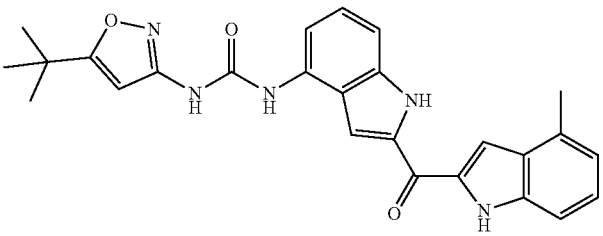 [SMILES: Cc1cccc2[nH]c(C(=O)c3cc4c(NC(=O)Nc5cc(C(C)(C)C)on5)cccc4[nH]3)cc12]

1-(5-(tert-Butyl)isoxazol-3-yl)-3-(2-(4-methyl-1H-indole-2-carbonyl)-1H-indol-5-yl)urea (36b):

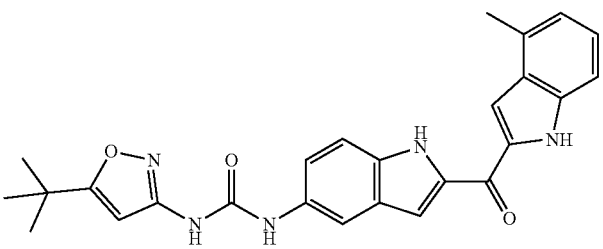 [SMILES: Cc1cccc2[nH]c(C(=O)c3cc4cc(NC(=O)Nc5cc(C(C)(C)C)on5)ccc4[nH]3)cc12]

TABLE 1-continued

| | |
|---|---|
| 1-(5-(tert-Butyl)isoxazol-3-yl)-3-(2-(4-methyl-1H-indole-2-carbonyl)-1H-indol-6-yl)urea (36c): | 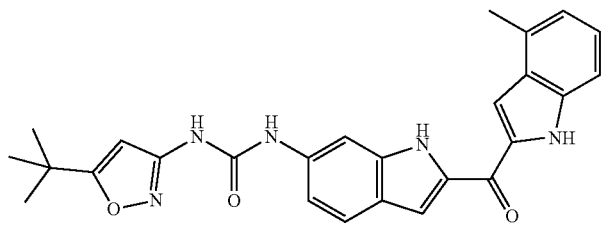 [SMILES: Cc1cccc2[nH]c(C(=O)c3cc4ccc(NC(=O)Nc5cc(C(C)(C)C)on5)cc4[nH]3)cc12] |
| 1-(5-(tert-butyl)isoxazol-3-yl)-3-(2-(4-methyl-1H-indole-2-carbonyl)-1H-indol-7-yl)urea (36d) | 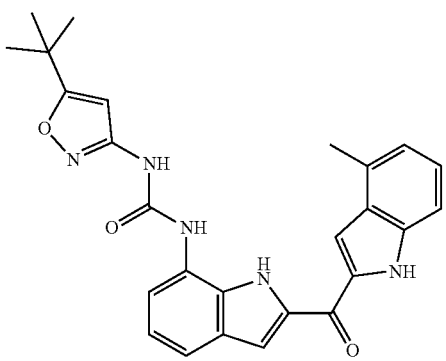 [SMILES: Cc1cccc2[nH]c(C(=O)c3cc4cccc(NC(=O)Nc5cc(C(C)(C)C)on5)c4[nH]3)cc12] |
| 1-(5-(tert-Butyl)isoxazol-3-yl)-3-(2-(5-hydroxy-1H-indole-2-carbonyl)-1H-indol-5-yl)urea (36e) | 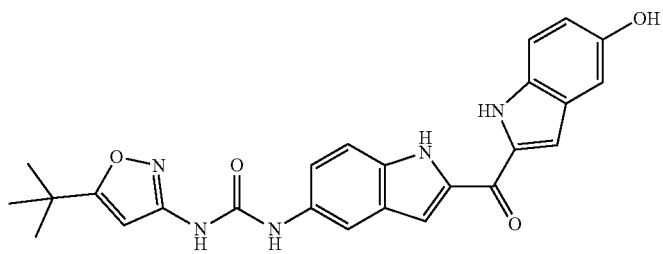 |
| 1-(5-(tert-butyl)isoxazol-3-yl)-3-(2-(5-hydroxy-1H-indole-2-carbonyl)-1H-pyrrolo[2,3-b]pyridin-5-yl)urea (36f) | 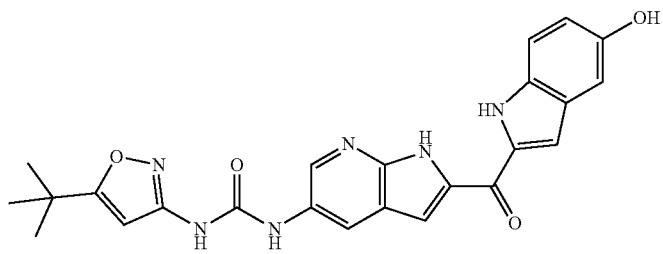 [SMILES: CC(C)(C)c1cc(NC(=O)Nc2cnc3[nH]c(C(=O)c4cc5cc(O)ccc5[nH]4)cc3c2)no1] |
| 1-(5-(tert-Butyl)isoxazol-3-yl)-3-(2-(5-hydroxy-1H-indole-2-carbonyl)-1H-pyrrolo[2,3-c]pyridin-5-yl)urea (36g) | 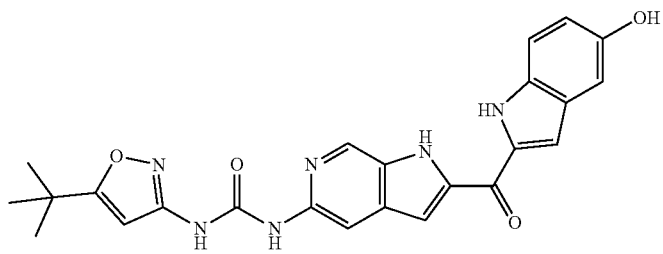 [SMILES: CC(C)(C)c1cc(NC(=O)Nc2cc3cc(C(=O)c4cc5cc(O)ccc5[nH]4)[nH]c3cn2)no1] |
| 1-(5-(tert-Butyl)isoxazol-3-yl)-3-(2-(5-hydroxybenzofuran-2-carbonyl)-1H-indol-5-yl)urea (36h) | 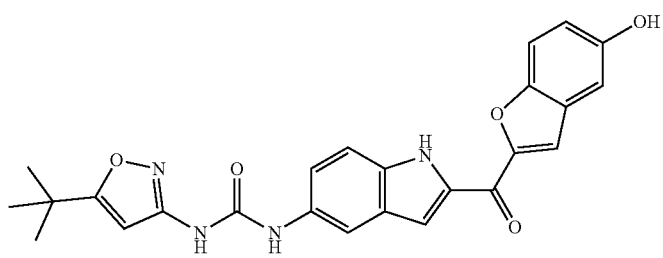 [SMILES: CC(C)(C)c1cc(NC(=O)Nc2ccc3[nH]c(C(=O)c4cc5cc(O)ccc5o4)cc3c2)no1] |

TABLE 1-continued 1-(5-(tert-Butyl)isoxazol-3-yl)-3-(2-(5-hydroxybenzofuran-2-carbonyl)-1H-pyrrolo[2,3-c]pyridin-5-yl)urea (36i)

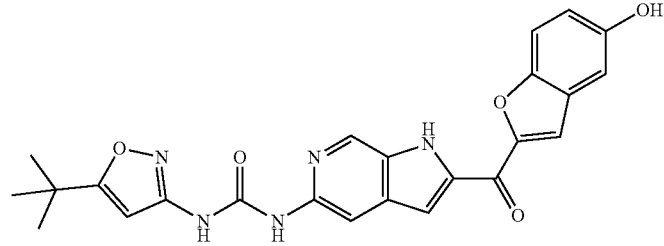 [SMILES: CC(C)(C)c1cc(NC(=O)Nc2cc3cc(C(=O)c4cc5cc(O)ccc5o4)[nH]c3cn2)no1]

1-(5-tert-Butyl-1,3,4-thiadiazol-2-yl)-3-(2-(5-hydroxy-1H-indole-2-carbonyl)-1H-indol-5-yl)urea (46b):

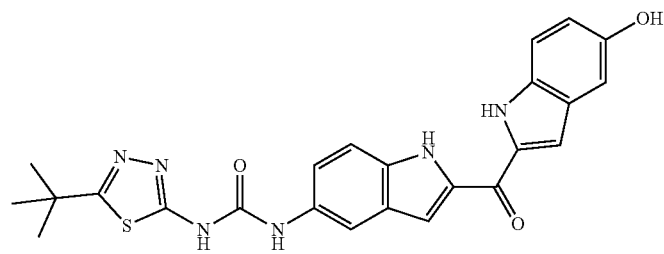 [SMILES: CC(C)(C)c1nnc(NC(=O)Nc2ccc3[nH]c(C(=O)c4cc5cc(O)ccc5[nH]4)cc3c2)s1]

1-(5-tert-Butylisothiazol-3-yl)-3-(2-(5-hydroxy-1H-indol-2-carbonyl)-1H-indol-5-yl) urea (46c):

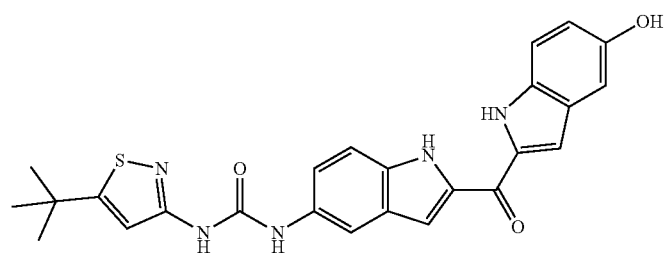 [SMILES: CC(C)(C)c1cc(NC(=O)Nc2ccc3[nH]c(C(=O)c4cc5cc(O)ccc5[nH]4)cc3c2)ns1]

1-(2-(5-Hydroxy-1H-indol-2-carbonyl)-1H-indol-5-yl)-3-(5-methylisoxazol-3-yl) urea (46d):

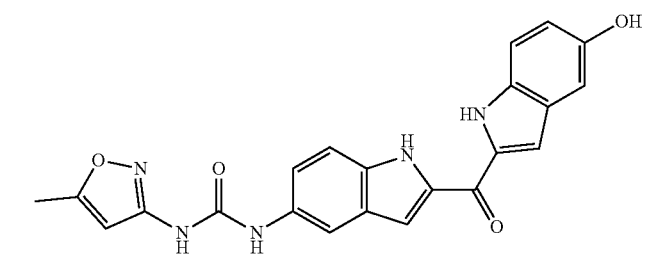 [SMILES: Cc1cc(NC(=O)Nc2ccc3[nH]c(C(=O)c4cc5cc(O)ccc5[nH]4)cc3c2)no1]

6-((2-(5-(3-(5-(tert-Butyl)isoxazol-3-yl)ureido)-1H-indole-2-carbonyl)-1H-indol-5-yl)oxy)hexanoic acid (40a)

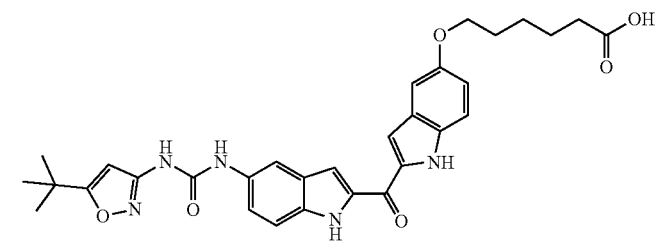 [SMILES: CC(C)(C)c1cc(NC(=O)Nc2ccc3[nH]c(C(=O)c4cc5cc(OCCCCCC(=O)O)ccc5[nH]4)cc3c2)no1]

6-((2-(5-(3-(5-(tert-Butyl)isoxazol-3-yl)ureido)-1H-indole-2-carbonyl)-1H-indol-5-yl)oxy)hexanoic acid (40b)

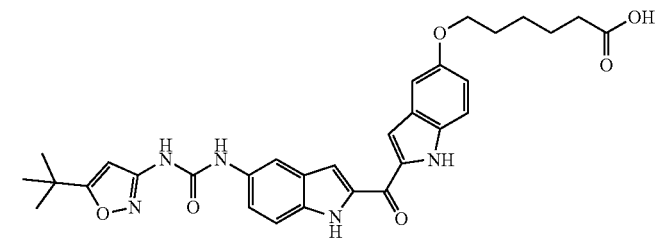 [SMILES: CC(C)(C)c1cc(NC(=O)Nc2ccc3[nH]c(C(=O)c4cc5cc(OCCCCCC(=O)O)ccc5[nH]4)cc3c2)no1]

TABLE 1-continued

| | |
|---|---|
| Methyl 6-((2-(5-(3-(5-(tert-butyl)isoxazol-3-yl)ureido)-1H-indole-2-carbonyl)-1H-indol-5-yl)oxy)hexanoate (41b) | 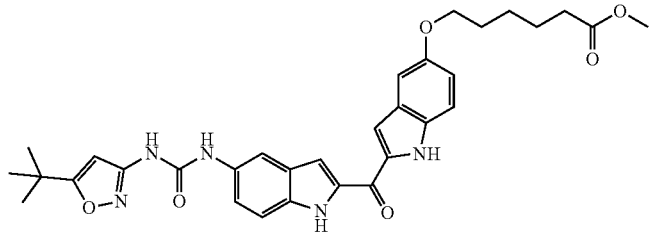 [SMILES: COC(=O)CCCCCOc1ccc2[nH]c(C(=O)c3cc4cc(NC(=O)Nc5cc(C(C)(C)C)on5)ccc4[nH]3)cc2c1] |
| 1-(2-(5-(2-Aminoethoxy)-1H-indole-2-carbonyl)-1H-indol-5-yl)-3-(5-(tert-butyl)isoxazol-3-yl)urea (44) | 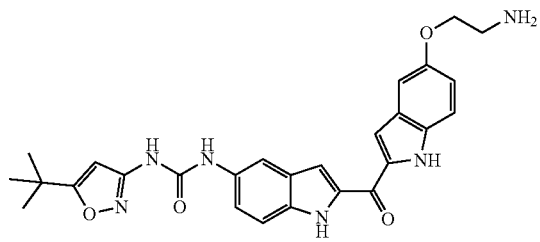 [SMILES: CC(C)(C)c1cc(NC(=O)Nc2ccc3[nH]c(C(=O)c4cc5cc(OCCN)ccc5[nH]4)cc3c2)no1] |
| (E)-N-(2-((2-(5-(3-(5-tert-Butyl-isoxazol-3-yl)ureido)-1H-indol-2-carbonyl)-1H-indol-5-yl)oxy)ethyl)-3-(dimethylamino)acrylamide (45) | 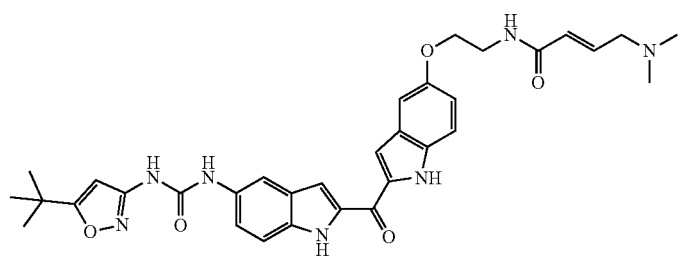 [SMILES: CN(C)C/C=C/C(=O)NCCOc1ccc2[nH]c(C(=O)c3cc4cc(NC(=O)Nc5cc(C(C)(C)C)on5)ccc4[nH]3)cc2c1] |
| 2-(5-(3-(5-(tert-Butyl)isoxazol-3-yl)ureido)benzofuran-2-carbonyl)-1H-indol-5-yl [1,4'-bipiperidine]-1'-carboxylate (48a) | 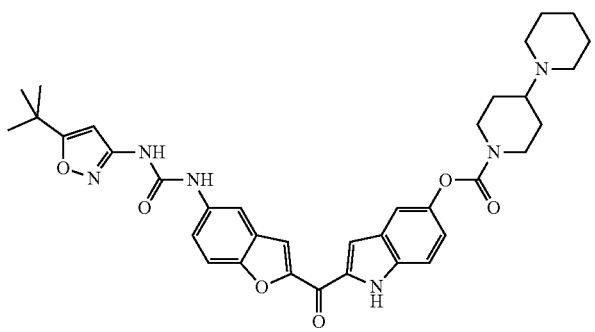 [SMILES: CC(C)(C)c1cc(NC(=O)Nc2ccc3oc(C(=O)c4cc5cc(OC(=O)N6CCC(N7CCCCC7)CC6)ccc5[nH]4)cc3c2)no1] |
| 2-(5-(3-(5-(tert-butyl)isoxazol-3-yl)ureido)benzofuran-2-carbonyl)-1H-indol-5-yl [1,4'-bipiperidine]-1'-carboxylate hydrochloride (48b) | 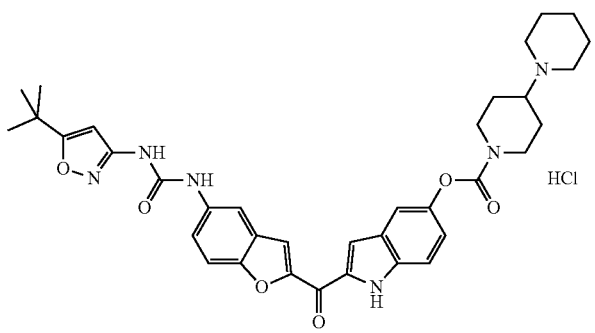 [SMILES: CC(C)(C)c1cc(NC(=O)Nc2ccc3oc(C(=O)c4cc5cc(OC(=O)N6CCC(N7CCCCC7)CC6)ccc5[nH]4)cc3c2)no1 ; Cl] |

Pharmaceutical Compositions and Medical Uses

The present invention provides pharmaceutical compositions comprising (a) at least one compound according to the present invention, and/or (b) optionally, a pharmaceutically acceptable salt or solvate of at least one compound according to the present invention, and/or (c) optionally, an additional pharmaceutically active agent or drug, (d) optionally, pharmaceutically acceptable excipient(s) and/or carrier.

The present invention provides the use of compounds according to the invention as tyrosine kinase inhibitors, preferably Flt3 inhibitor. Further, the present invention provides the use of a pharmaceutically acceptable salt or solvate of the compounds according to the invention as tyrosine kinase inhibitor, preferably Flt3 inhibitor. Still further, the present invention provides compounds according to the present invention or pharmaceutical compositions according to the present invention for use in medicine. The present invention provides also compounds according to the present invention or pharmaceutical compositions according to the present invention for use in the treatment of a disease. Preferably, the disease is selected from neoplastic diseases, referred to as cancer, such as leukemia, particularly from blood cancer, e.g., acute myeloid leukemia (AML).

The administration of the compounds according to this invention and pharmaceutical compositions according to the invention may be performed in any of the generally accepted modes of administration available in the art. Illustrative examples of suitable modes of administration include intravenous, oral, nasal, inhalable, parenteral, topical, transdermal and rectal delivery. Oral and intravenous delivery forms are preferred. In aspects of the invention injectable compositions comprising a therapeutically effective amount of the compounds of the invention are provided, including salts, esters, isomers, solvates, hydrates and polymorphs thereof, at least one vehicle comprising water, aqueous solvents, organic solvents, hydro-alcoholic solvents, oily substances, or mixtures thereof, and optionally one or more pharmaceutically acceptable excipients. Standard knowledge regarding these pharmaceutical ingredients and pharmaceutical formulations/compositions may be found, inter alia, in the 'Handbook of Pharmaceutical Excipients'; Edited by Raymond C Rowe, Paul J Sheskey, Walter G Cook and Marian E Fenton; May 2012 and/or in Remington: The Science and Practice of Pharmacy, 19th edition.

The pharmaceutical compositions may be formulated in the form of a dosage form for oral intravenous, oral, nasal, inhalable, parenteral, topical, transdermal and rectal and may thus comprise further pharmaceutically acceptable excipients, such as buffers, solvents, preservatives, disintegrants, stabilizers, carriers, diluents, fillers, binders, lubricants, glidants, colorants, pigments, taste masking agents, sweeteners, flavorants, plasticizers, and any acceptable auxiliary substances such as absorption enhancers, penetration enhancers, surfactants, co-surfactants, and specialized oils.

The proper excipient(s) is (are) selected based in part on the dosage form, the intended mode of administration, the intended release rate, and manufacturing reliability. Examples of common types of excipients include also various polymers, waxes, calcium phosphates, sugars, etc.

Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; polyalkylene glycols such as polyethylene glycol and polypropylene glycol; and polyacrylic acids including their copolymers and crosslinked polymers thereof, e.g., Eudragit® (Rohm), polycarbophil, and chitosan polymers. Waxes include white beeswax, microcrystalline wax, carnauba wax, hydrogenated castor oil, glyceryl behenate, glycerylpalmito stearate, and saturated polyglycolyzed glycerate. Calcium phosphates include dibasic calcium phosphate, anhydrous dibasic calcium phosphate, and tribasic calcium phosphate. Sugars include simple sugars, such as lactose, maltose, mannitol, fructose, sorbitol, saccharose, xylitol, isomaltose, and glucose, as well as complex sugars (polysaccharides), such as maltodextrin, amylodextrin, starches, and modified starches.

The pharmaceutical compositions of the present invention may be formulated into various types of dosage forms, for instance as solutions or suspensions, or as tablets, capsules, granules, pellets or sachets for oral administration. A particularly preferred pharmaceutical composition is in the form of a solid oral dosage form, preferably tablets. The tablet is preferably a tablet for swallowing. It may optionally be coated with a film coat comprising, in essence, any suitable inert coating material known in the art. The above lists of excipients and forms are not exhaustive.

The pharmaceutical composition of the present invention can be manufactured according to standard methods known in the art. Granulates according to the invention can be obtained by dry compaction or wet granulation. These granulates can subsequently be mixed with e.g. suitable disintegrating agents, glidants and lubricants and the mixture can be compressed into tablets or filled into sachets or capsules of suitable size. Tablets can also be obtained by direct compression of a suitable powder mixture, i.e. without any preceding granulation of the excipients. Suitable powder or granulate mixtures according to the invention are also obtainable by spray drying, lyophilization, melt extrusion, pellet layering, coating of the active pharmaceutical ingredient or any other suitable method. The so obtained powders or granulates can be mixed with one or more suitable ingredients and the resulting mixtures can either be compressed to form tablets or filled into sachets or capsules. The above mentioned methods known in the art also include grinding and sieving techniques permitting the adjustment of desired particle size distributions.

Injectable compositions of the present invention may contain a buffer (for example, sodium dihydrogen phosphate, disodium hydrogen phosphate and the like), an isotonizing agent (for example, glucose, sodium chloride and the like), a stabilizer (for example, sodium hydrogen sulfite and the like), a soothing agent (for example, glucose, benzyl alcohol, mepivacaine hydrochloride, xylocaine hydrochloride, procaine hydrochloride, carbocaine hydrochloride and the like), a preservative (for example, p-oxybenzoic acid ester such as methyl p-oxybenzoate and the like, thimerosal, chlorobutanol, benzyl alcohol and the like) and the like, if necessary. In addition, the injectable composition of the present invention may contain vitamins and the like. Further, injectable compositions of the present invention may contain an aqueous solvent, if necessary. Examples of the aqueous solvent include purified water for injection, physiological saline solution, and glucose solution. In injectable compositions of the present invention, the pharmaceutical compound may be solid. As used herein, the "solid" comprises crystals and amorphous substances which have conventional meanings. The form of the solid component is not particularly limited, but powder is preferred in view of dissolution rate.

Methods of Treatment

As discussed above, the present invention provides a method of treatment of a disease, in particular neoplastic diseases (often referred to as cancer). Treatment includes any of amelioration, alleviation, prevention from worsening, and curing a disease such as defined above, e.g., a cancer, particularly blood cancer, such as leukemia, especially such as acute myeloid leukemia (AML).

Treatment methods of the invention comprise the step of administering to a subject a therapeutically effective amount of a compound according to the invention or a pharmaceutical composition of the invention.

A "therapeutically effective amount" of a compound according to the invention preferably refers to the amount necessary to achieve the therapeutic outcome.

The dosage of the compounds according to the invention is carried out in the order of magnitude customary for FLT3 inhibitors. For example, the customary dose in the case of systemic therapy (p.o.) may be between 0.03 and 60 mg/kg body weight per day, (i.v.) may be between 0.03 and 60 mg/kg/h. In another embodiment, the customary dose in the case of systemic therapy (p.o.) is between 0.3 and 30 mg/kg per day, (i.v.) is between 0.3 and 30 mg/kg/h. The choice of the optimal dosage regime and duration of medication, particularly the optimal dose and manner of administration of the active compounds necessary in each case can be determined by a person skilled in the art on the basis of his/her expert knowledge.

Synthesis of the Compounds of the Invention

Further, the present invention provides a method of generating/synthesizing compounds according to the invention.

Said method may comprise the steps of procedures referred to below as a) or b) or c), wherein a) comprises the steps:

(1) acylation of 5-(benzyloxy)-1-(phenylsulfonyl)-1H-indole, (2) bromination in alpha position, (3) reaction with 2-hydroxy-5-nitrobenzaldehyde and ring closure mediated by a base, such as $K_2CO_3$, (4) Cleavage of the phenylsulfony-protection group by a base as NaOH, followed by catalytic hydrogenolytic cleavage of the benzyloxy group, (5) Reaction with an isocyanate to obtain the substituted urea derivative;

and wherein b) comprises the steps:

1) Lithiation using t-BuLi and reaction of the aryl-lithium intermediate with a carbonyl chloride, 2) Cleavage of the sulfonyl protecting group, 3) Acidic cleavage of the protecting group, e.g., a Boc-group, and 4) reaction with a suitable isocyanate.

and wherein c) comprises the steps:

(1) Reaction with a chlorocarbonyl derivative of an amine in pyridine, or by the reaction of amines with a chlorocarbonyl compound, which can be obtained by treatment of a phenole with phosgen in presence of triethylamine, and (2) transformation to a pharmaceutically acceptable salt by treatment with a suitable organic or anorganic acid, such as HCl.

These method steps are shown below in Schemes 1-10:

Synthesis of Building Blocks Used for the Synthesis Shown in Schemes 3-4

Compounds 16a-16e, which were used for the synthesis shown in the following schemes were prepared as shown in schemes 1 and 2: 13a-e were protected as sulfonamides according to Mahboobi et al. (Mahboobi, Uecker et al. 2006) to yield 14a-e, which were reduced by use of Zn/HCl to the corresponding amines 15a-e. Subsequent reaction with di-tert-butyl dicarbonate (Lougiakis, Marakos et al. 2008) resulted in formation of 16a-e (scheme 1).

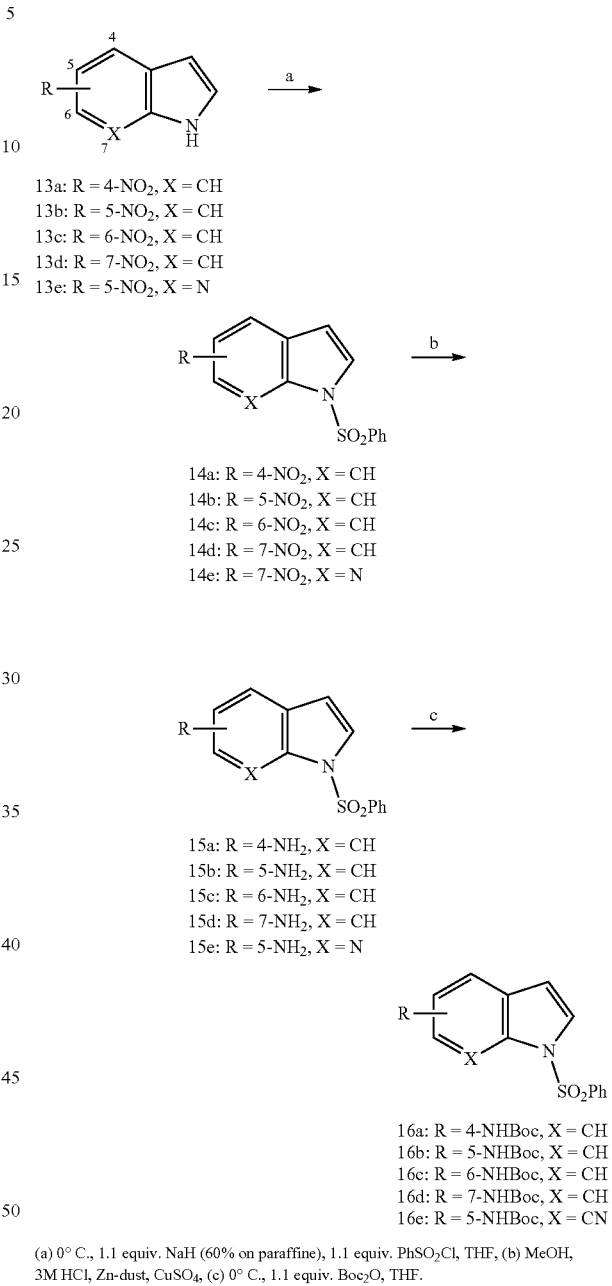

Scheme 1: Synthesis of derivatives of of tert-butyl (1-(phenylsulfonyl)-1H-indolyl)carbamates 16a-d and tert-butyl (1-(phenylsufonyl)-1H-pyrrolo[2,3-b]pyridin-5-yl)carbamate (16e).

13a: R = 4-$NO_2$, X = CH
13b: R = 5-$NO_2$, X = CH
13c: R = 6-$NO_2$, X = CH
13d: R = 7-$NO_2$, X = CH
13e: R = 5-$NO_2$, X = N

14a: R = 4-$NO_2$, X = CH
14b: R = 5-$NO_2$, X = CH
14c: R = 6-$NO_2$, X = CH
14d: R = 7-$NO_2$, X = CH
14e: R = 7-$NO_2$, X = N

15a: R = 4-$NH_2$, X = CH
15b: R = 5-$NH_2$, X = CH
15c: R = 6-$NH_2$, X = CH
15d: R = 7-$NH_2$, X = CH
15e: R = 5-$NH_2$, X = N

16a: R = 4-NHBoc, X = CH
16b: R = 5-NHBoc, X = CH
16c: R = 6-NHBoc, X = CH
16d: R = 7-NHBoc, X = CH
16e: R = 5-NHBoc, X = CN (a) 0° C., 1.1 equiv. NaH (60% on paraffine), 1.1 equiv. $PhSO_2Cl$, THF, (b) MeOH, 3M HCl, Zn-dust, $CuSO_4$, (c) 0° C., 1.1 equiv. $Boc_2O$, THF.

Building block 16f (scheme 2, infra) was synthesized from commercially available 4-methyl-5-nitropyridin-2-amine (17) mainly according to Andaloussi et al. (Andaloussi, Moreau et al. 2007). In the first step 17 was treated with NaH as a base and $Boc_2O$ to yield Boc protected pyridine derivative 18. The desired enamine 19 was prepared using N,N-dimethylformamide dimethyl acetal (DMFDMA) in DMF. Cyclization of 19 by use of Pd/C, $H_2$ revealed tert-butyl 1H-pyrrolo[2,3-c]pyridin-5-ylcarbamate (20), (Andaloussi, Moreau et al. 2007) which was in the following protected with the phenylsulfonyl-group to obtain 16f.

Scheme 2: Synthesis of tert-butyl (1-(phenylsulfonyl)-1H-pyrrolo[2,3-c]pyridin-5-yl)carbamate (16f).

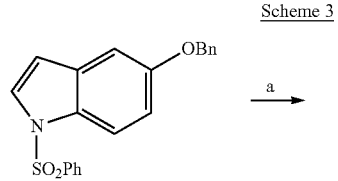

(a) NaH, BOc₂O, (b) DMFDMA, pyrrolidine, DMF, (c) 10% Pd/C, H₂ (30 bar), 70° C., THF, MeOH (2:1), (d) 1.1 equiv. NaH (60% on paraffine), 0° C., 1.1 equiv. PhSO₂Cl, THF.

Synthesis of Arylmethanone-Derivatives

To obtain the desired aryl-methanone derivative 28 also referred to as Marbotinib in the following, 5-benzyloxyindole was protected by use of benzenesulfonyl chloride as described (Mahboobi, Teller et al. 2002) to get 21. After acetylation 22 was obtained, which was brominated in alpha-position to the carbonyl-group using CuBr₂ to give 23. Reaction of 23 with 2-hydroxy-5-nitrobenzaldehyde (24) resulted in the formation of (5-(benzyloxy)-1-(phenylsulfonyl)-1H-indol-2-yl)(5-nitrobenzofuran-2-yl)methanone as an intermediate. After alkaline cleavage of the phenylsulfonyl-protecting group 25 was obtained. By use of ammonium formate and Pd/C the nitro- and Bn-groups were reduced. Finally, reaction of 26 with 5-(tert-butyl)-3-isocyanatoisoxazole 27a in THF led to target compound 28 (Marbotinib)

Scheme 3

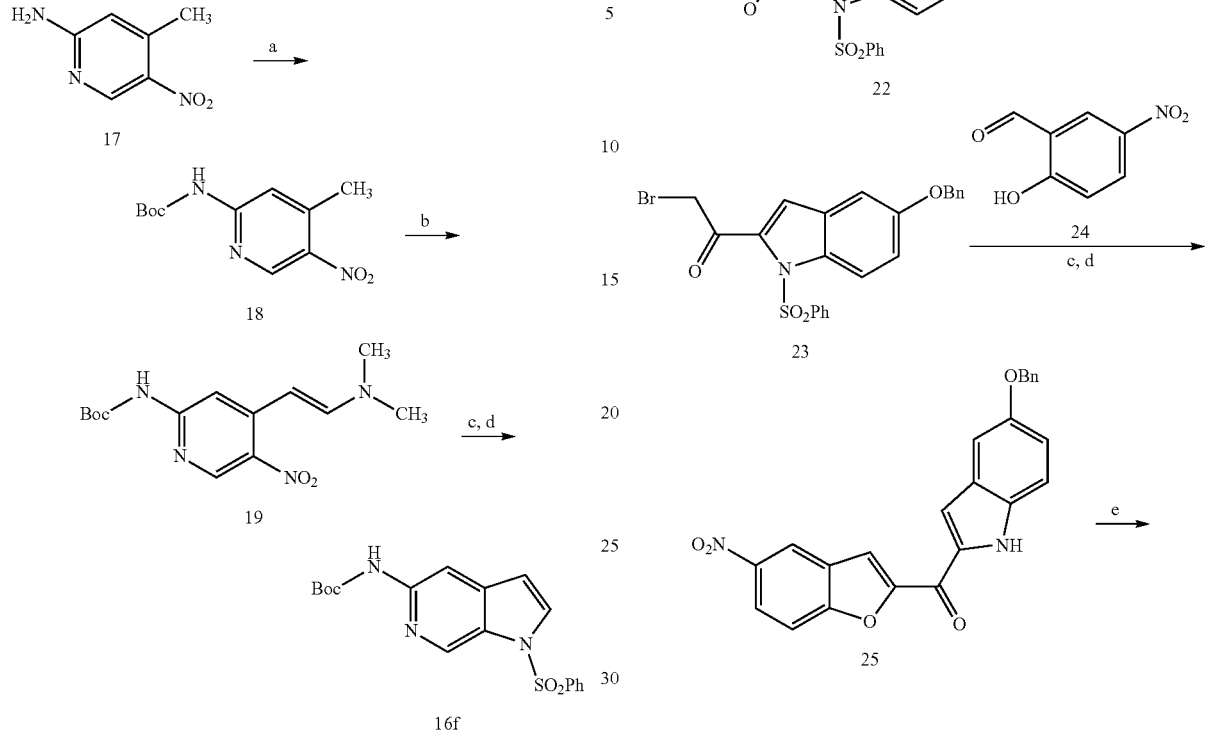

(a) 1.1 equiv. n-BuLi, -78° C. THF, 11.0 equiv. Ac₂O, (b) 2.0 equiv. CuBr₂, EtOAc, HBr (kat.), (c) 1.0 equiv. K₂CO₃, 2-Butanone, 80° C., (d) NaOH (10%), MeOH, THF (1:1:1), reflux, (e) Pd/C (10%), 4.0 equiv. NH₄HCOO, MeOH, THF (1:1), 80° C., (f) 1M 5-(tert-Butyl)-3-isocyanatoisoxazole 27a in THF, THF, Pyridin.

Alternatively, aryl-methanone derivatives 36a-i can be obtained by the synthetic routes shown in schemes 4-6b:

Scheme 4: Synthesis of the amino compounds 31a-d
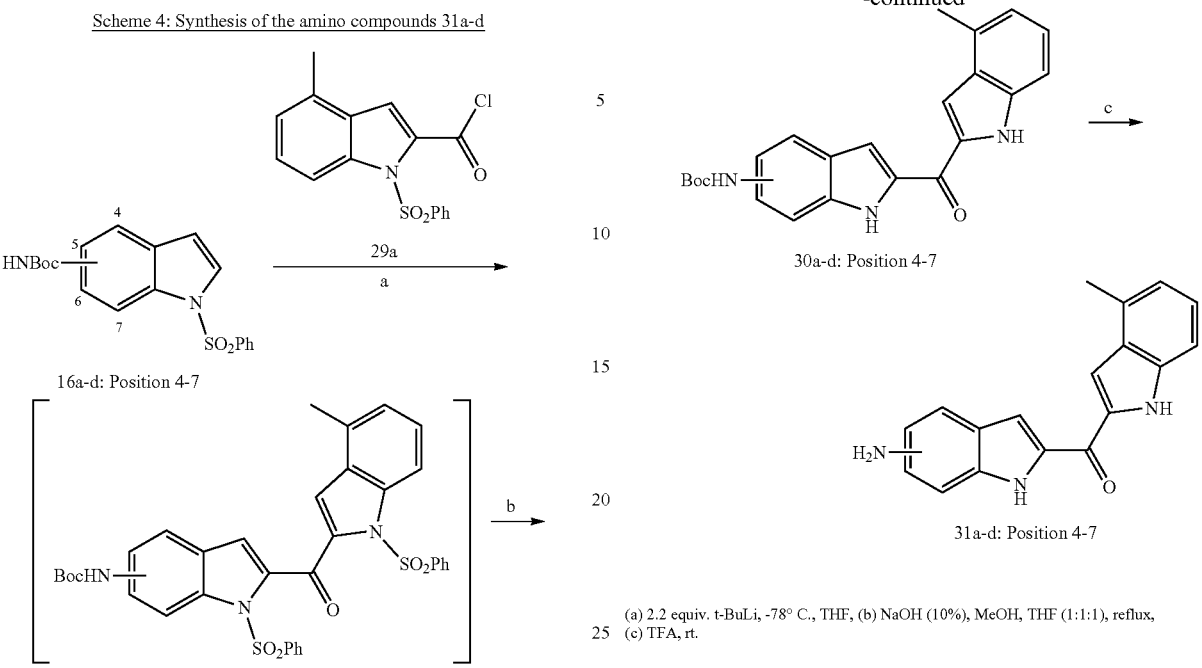
(a) 2.2 equiv. t-BuLi, -78° C., THF, (b) NaOH (10%), MeOH, THF (1:1:1), reflux, (c) TFA, rt.
Scheme 5: Synthesis of the amino compounds 35e, g-i
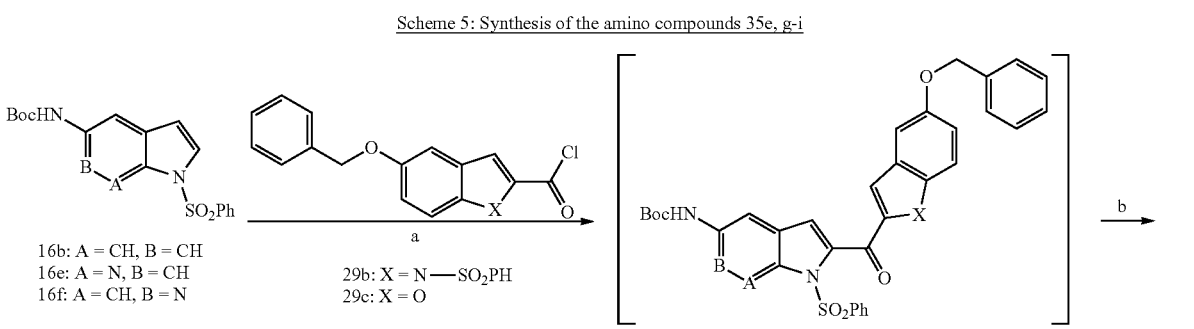
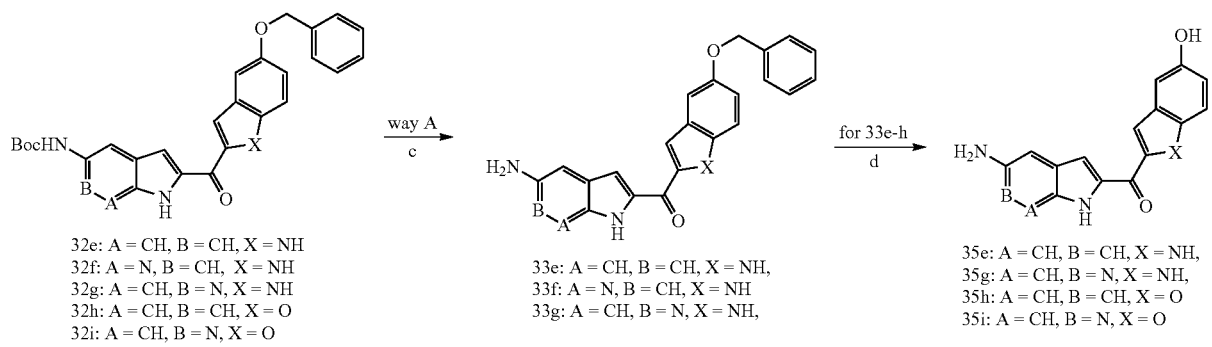

-continued

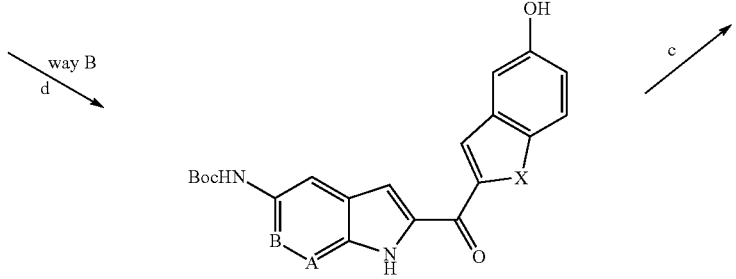

34e: A = CH, B = CH, X = N
34h: A = CH, B = CH, X = O
34i: A = CH, B = N, X = O (a) 2.2 equiv. t-BuLi, -78° C., THF, (b) NaOH (10%), MeOH, THF (1:1:1), reflux, (c) TFA, rt, (d) Pd/C (10%), 4.0 equiv. NH₄HCOO, MeOH, THF (1:1), 80° C., 16a-d (scheme 4), and, respectively, 16b, 16e and 16f (Scheme 5) were lithiated using t-BuLi and the aryl-lithium intermediates reacted with the respective carbonyl chlorides 29a-c, which were prepared in analogy to Mahboobi et al. (Mahboobi, Uecker et al. 2006). After cleavage of the sulfonyl protecting group (Mahboobi, Uecker et al. 2006) 30a-d (scheme 4) and 32e-i (scheme 5) were obtained. Acidic cleavage of the Boc-group with TFA yielded 31a-d (scheme 4) and 33e-g (scheme 5), respectively. To obtain the hydroxy-analogues 35e, 35g-35h the benzyloxy-group was hydrogenolytically cleaved (Mahboobi, Uecker et al. 2006) (way A). The sequence of the synthesis steps c) and d) shown in scheme 5 can moreover be modified. By this alternative route, way B., e.g., 35i was obtained.

-continued

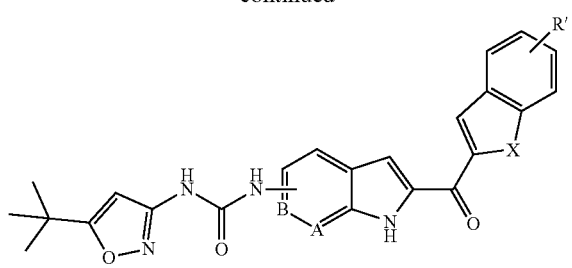

36a-d: Position 4-7,
A = CH, B = CH, X = NH, R' = 4-CH₃

36e: Position 5, A = CH, B = CH, X = NH, R' = 5-OH
36g: Position 5, A = CH, B = N, X = NH, R' = 5-OH
36h: Position 5, A = CH, B = CH, X = O, R' = 5-OH
36i: Position 5, A= CH, B = N, X = O, R' = 5-OH (a) 1M solution of 5-(tert-butyl)-3-isocyanatoisoxazole 27a in THF, THF, pyridine.

Amino compounds 31a-d and 35e-i were treated with 5-(tert-butyl)-3-isocyanatoisoxazole (27a) to obtain 36a-i (Chao, Sprankle et al. 2009) (scheme 6a). As shown in the synthesis of 36f (scheme 6b), the sequence of the synthesis steps can be modified. The benzyloxy-group can also finally be removed from the respective urea.

Scheme 6a: Synthesis of aryl-methanone derivatives 36a-i.

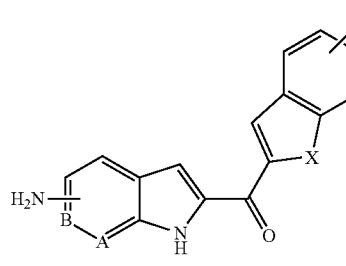

31a-d: Position 4-7,
A = CH, B = CH, X = NH, R' = 4-CH₃

35e: Position 5, A = CH, B = CH, X = NH, R' = 5-OH
35g: Position 5, A = CH, B = N, X = NH, R' = 5-OH
35h: Position 5, A = CH, B = CH, X = O, R' = 5-OH
35i: Position 5, A= CH, B = N, X = O, R' = 5-OH Scheme 6b: Modified reaction sequence for synthesis of 36f by reaction of the isocyanate 27a with 33f. In the first step the urea derivative is formed, followed by hydrogenolytic cleavage to 36f.

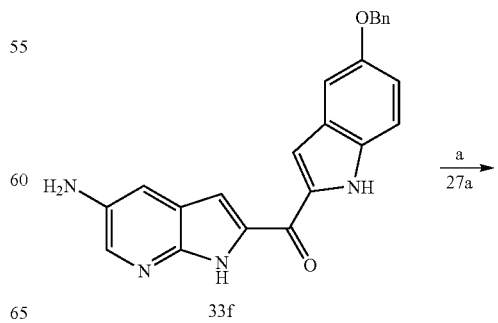

33f

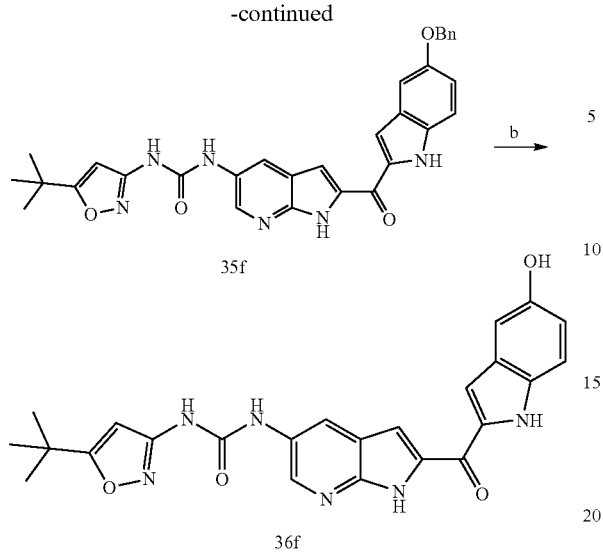

35f

36f (a) 0.1M Solution of 5-(tert-Butyl)-3-isocyantoisoxazole (27a) in THF, THF, kat. Pyridine, RT, (b) Pd/C (10%), 4.0 equiv. NH4HCOO, MeOH, THF (1:1), 80° C.

Further modifications of the compounds, exemplified by modifications of 36e, can be performed with the aim of improving solubility by introduction of suitable substituents or to create irreversible binding inhibitors by introduction of covalent binding groups in addition.

In scheme 7, e.g., the introduction of the 4-ethylmorpholine-substituent or a carboxylic acid residue into the core structure of 36e is shown, which enables the conversion of the compound to a pharmaceutically acceptable salt and to enhance solubility.

Scheme 7: Introduction of the 4-ethylmorpholine-substituent or a carboxylic acid residue into the core structure of 36e.

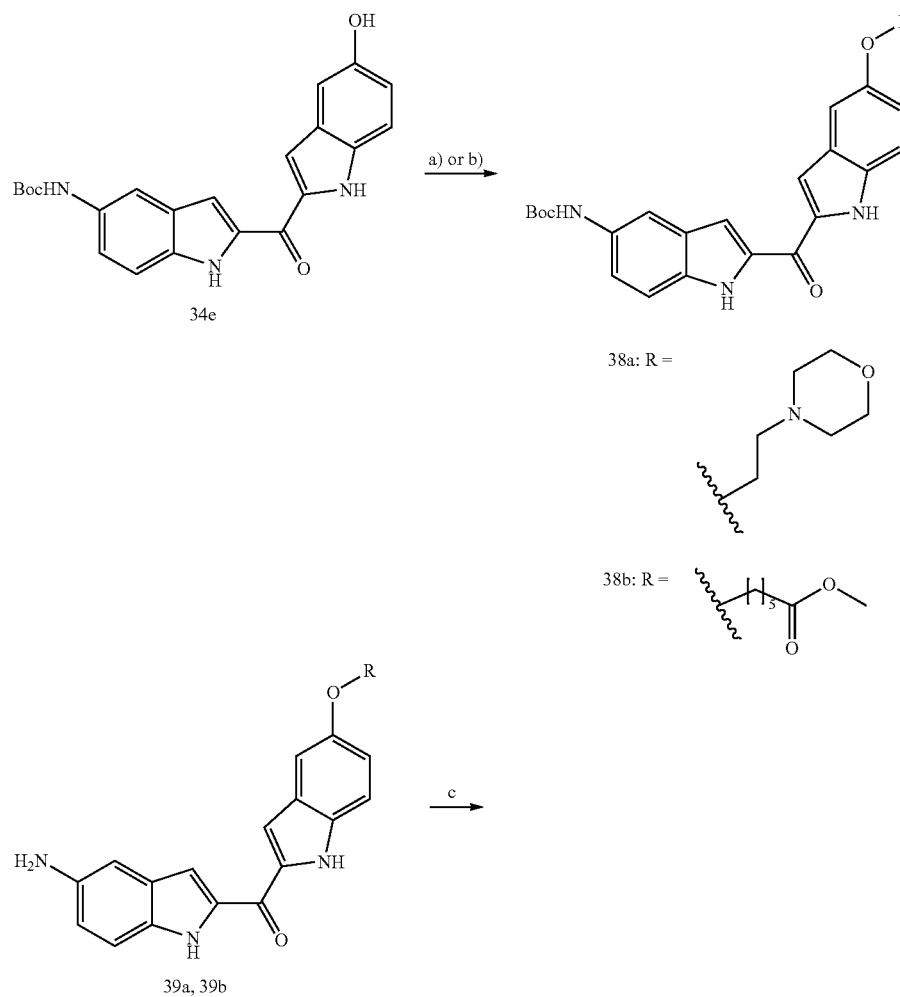

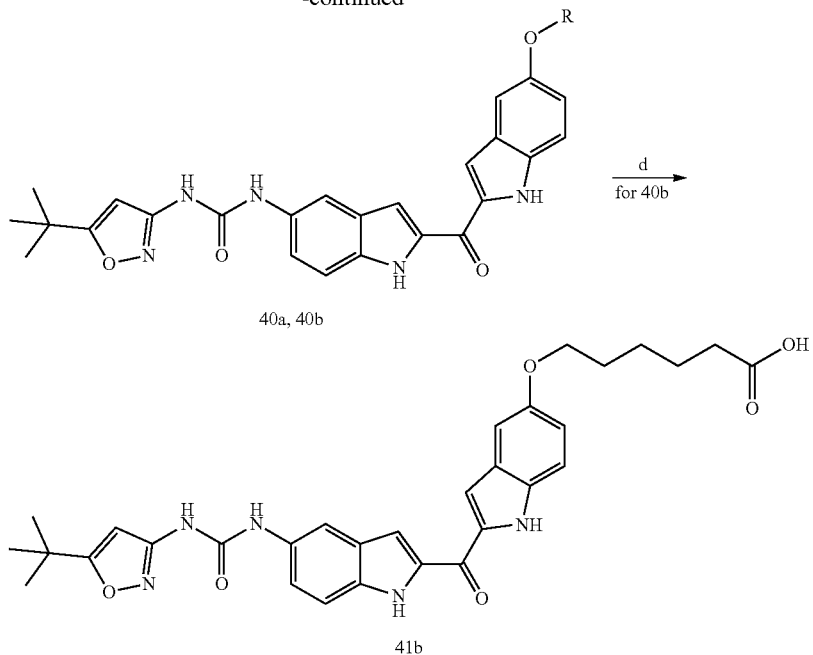

40a, 40b

41b (a) 4-(2-Chloroethyl)morpholine hydrochloride (37), K₂CO₃, DMF, 40° C., 5d, (b) Methyl 6-bromohexanoate (38), K₂CO₃, DMF, 20° C., 3d,
(c) i) TFA, rt, ii) NH₃ (d) 1M solution of 5-(tert-butyl)-3-isocyanatoisoxazole 27a in THF, THF, pyridine, d) LiOH, MeOH, THF, H₂O 1:1:1, 40° C.

As shown in scheme 8, the introduction of the (E)-3-(dimethylamino)-N-ethylacrylamide-substituent and formation of 45 can be performed in 3 steps. First, 43 was formed by Mitsonubu-reaction of 36e with tert-Butyl-(2-hydroxyethyl)carbamate (42) according to Arndt, Chan et al. 2011, followed by deprotection of 43 and amidation of the resulting amine hydrochloride with ((E)-4-(Dimethylamino)but-2-enic acid), mediated by BOP.

Scheme 8: Introduction of the (E)-3-(dimethylamino)-N-ethylacrylamide-substituent into the core structure of 36e.

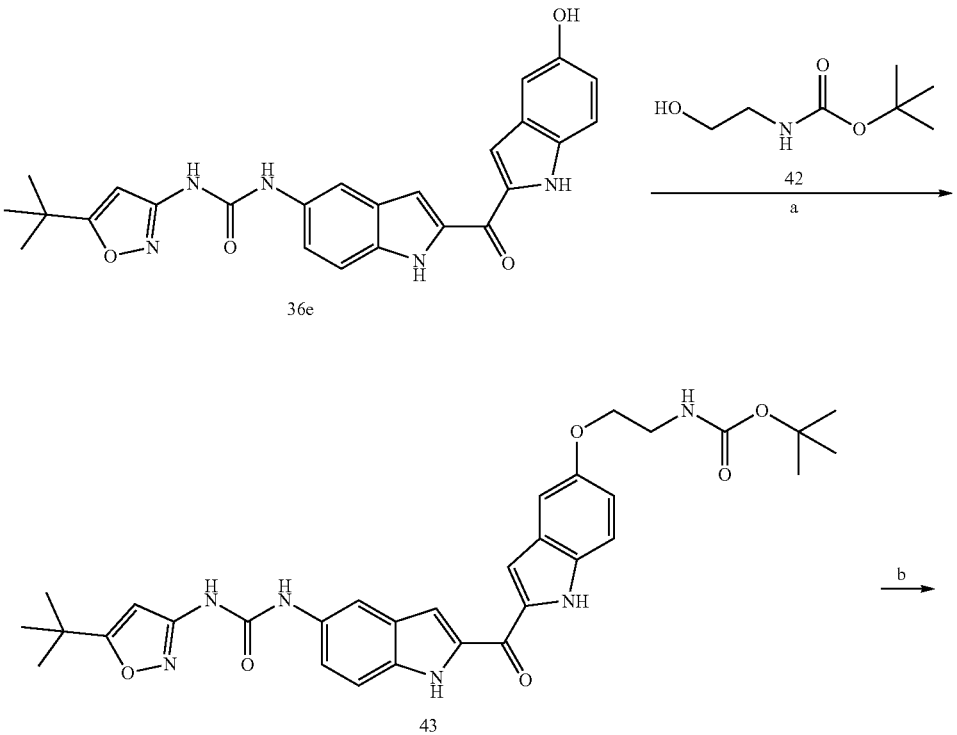

-continued

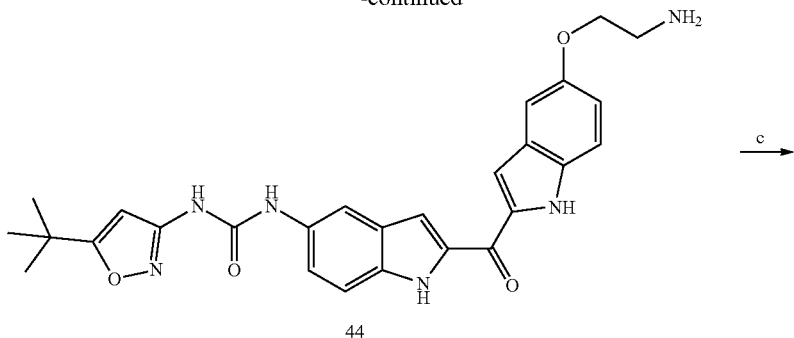

(a) 1.2 equiv. tert-Butyl-(2-hydroxyethyl)carbamate (42), 1.5 equiv. PPh₃, 1.5 equiv. DIAD, THF, 50° C., b) 4M HCl in Dioxane, Dioxane, 40° C.
(c) 1.1 equiv. ((E)-4-(Dimethylamino)but-2-enic acid), 3.5 equiv. NEt₃, 1.2 equiv. BOP, DMF.

To modify the heterocylic aromatic system connected to the urea-group (structural element Q in the general formula I) isocyanate intermediates 27b-d were prepared from arylamines using trichloromethyl chloroformate in THF (Bhagwat, Chao et al. 2007). Subsequently, the generation of 46b-d was performed by reaction with 5-amino-5'-hydroxy aryl methanone 35e (scheme 9).

Scheme 9. Synthesis of aryl-methanone derivatives 46b-d.

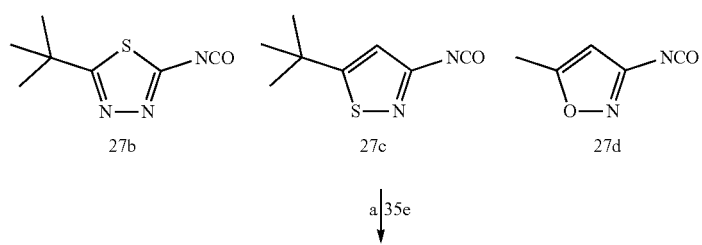

-continued

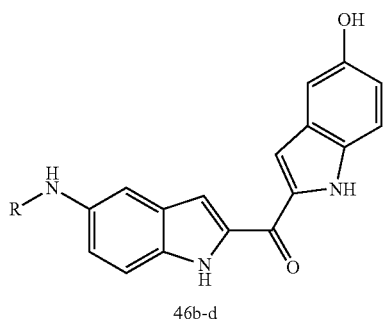
46b-d

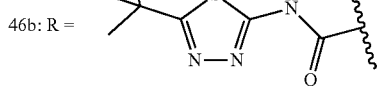
46b: R =

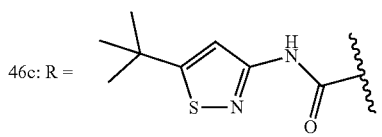
46c: R =

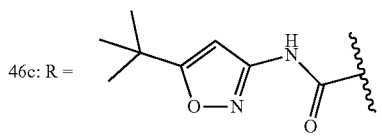
46c: R =

(a) 35e, THF, 50° C.

To modify the phenolic OH group of 28 in order to obtain carbamates with improved water solubility as prodrugs, 28 was reacted with 1,4'-bipiperidine-1'-carbonyl chloride in a mixture of $CH_2Cl_2$ and Pyridine. Alternative 28 can be treated with phosgene and the resulting chlorocarbonyloxy intermediate reacted with the amine.

The respective hydrochloride was obtained by treatment of 48a with HCl in 2-propanol.

Scheme 10. Synthesis of carbamate derivative and their salts.

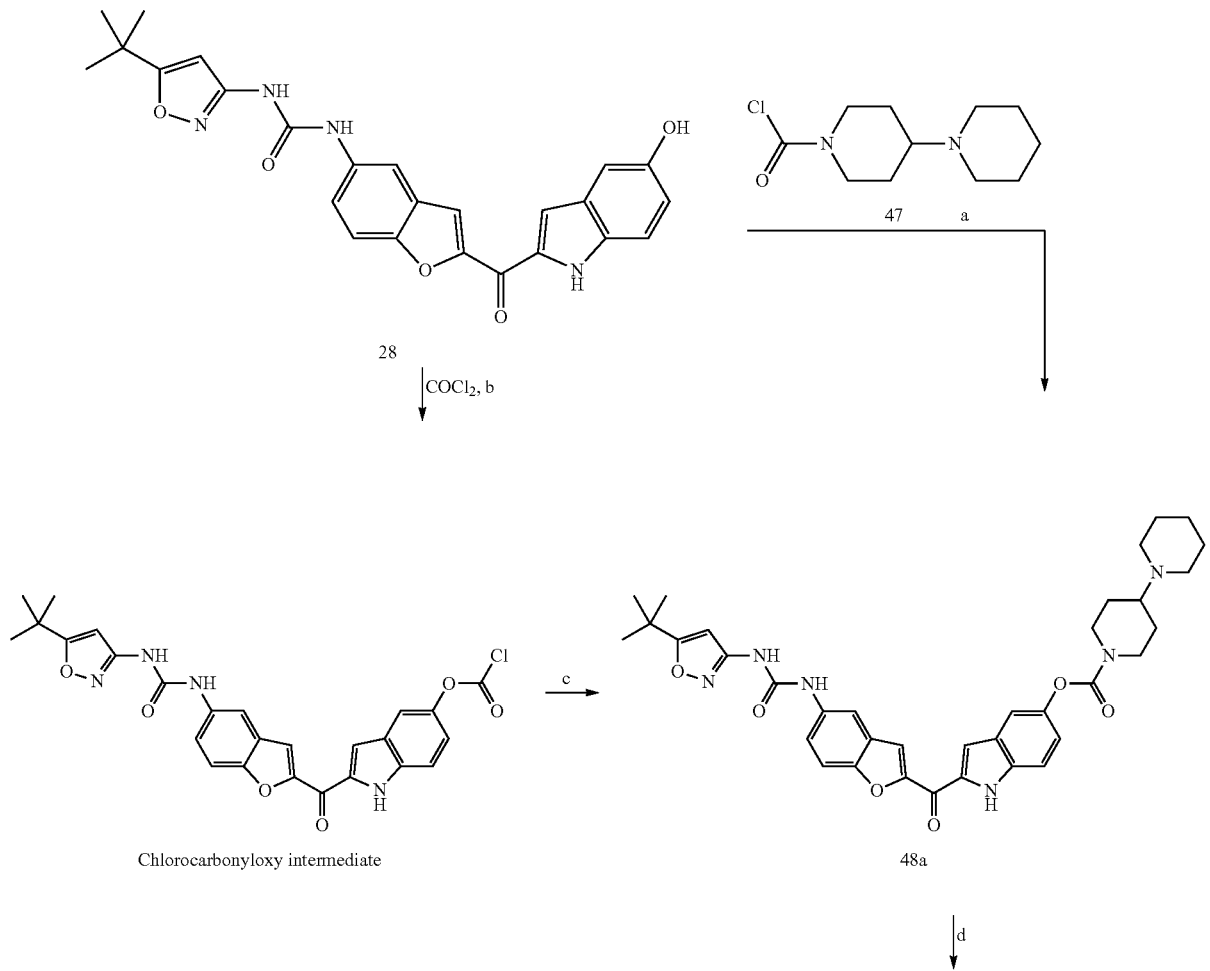

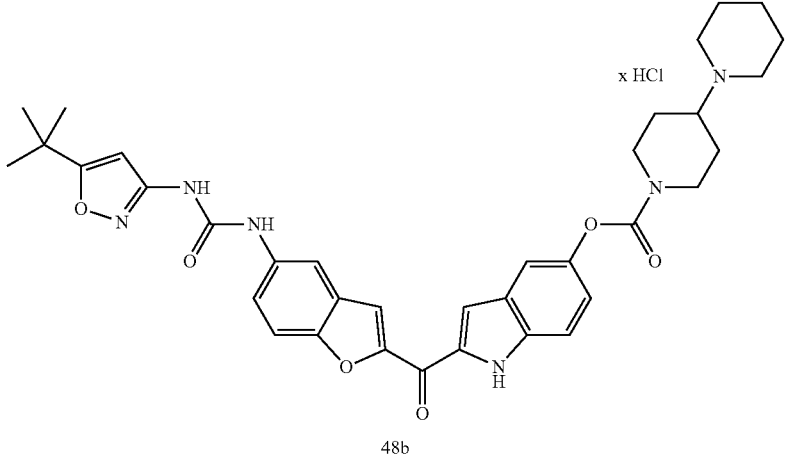

48b (a) Pyridine, CH₂Cl₂, rt, 16 h, ° C., b) CH₂Cl₂, NEt₃ (c) 1,4'-bipiperdine

EXAMPLES

Materials and Methods

Cell Lines and Primaries

MV4-11 and MOLM-13 are human acute myeloid leukemia cell lines that carry a FLT3-ITD mutation (American Type Culture Collection, ATCC Accession No: CRL-9591). Human erythroleukemic cell line K562. NB4 cells derived from acute promyelocytic leukemia.

Murine pro B cell line Ba/F3 Wild type (WT) cells and Ba/F3 ITD N676K, D835Y, ITD D835Y and D835Y N676K mutant cells. Peripheral blood mononuclear cells were freshly isolated from whole blood samples by Ficoll (Sigma Histopaque®-1077).

All cells are cultured in Roswell Park Memorial Institute (RPMI) 1640 medium plus 10% fetal bovine serum and 100 U/mL penicillin and 100 μg/mL streptomycin.

Substances

The following commercially available substances and compounds were used: AC220, Crenolanib, and Staurosporine (all substances provided by Selleckchem).

Flow Cytometry

The assay is carried out as described in (Noack, Mahendrarajah et al. 2016) We treated cells as described in the legends. After incubation, cells were harvested on ice and fixed in 80% ethanol at −20° C. for at least 1 h. Next, the cells were incubated with RNase for 30 min at room temperature, thereafter stained with propidium iodide (PI), and measured immediately with a flow cytometer. PI intercalates into DNA. In the different phases of the cell cycle, cells incorporate various amounts of PI. This allows the quantification of the cell cycle phases. The subG1 population represents the fraction of apoptotic/necrotic cells, which contains only fragmented DNA (DNA content <2N).

To analyze apoptosis cells were treated as indicated and harvested on ice. Thereafter cells were stained with Annexin V FITC for 15 min on ice in the dark. After incubation time cells were stained with PI and measured immediately on flow cytometer. An Annexin V FITC and PI single stained sample was used for compensation and an unstained control sample was used to exclude autofluorescence.

Western Blot Analysis

The assay is carried out as described in (Beyer, Kiweler et al. 2017).

1. Experimental Section:

Chemical Procedures.

In general, NMR spectra were recorded with a Bruker Avance 300 MHz spectrometer at 300K, using TMS as an internal standard. IR spectra (KBr or pure solid) were measured with a Bruker Tensor 27 spectrometer. Melting points were determined with a Bichi B-545. MS spectra were measured with a Finnigan MAT SSQ 710A, a Finnigan MAT 95 or respectively a ThermoQuest Finnigan TSQ 7000. All reactions were carried out under nitrogen atmosphere. Elemental analyses were performed by the Analytical Lab. of the University of Regensburg.

Introduction of the Phenylsulfonyl-Protection Group—General Procedure 1

During 20 min, NaH (60% dispersion in mineral oil, 3.40 g, 90.0 mmol) was added to a stirred solution of the respective indole or pyrrolopyridine (80 mmol) in 60 mL of anhydrous THF at 0° C. After stirring at rt for 1 h, benzenesulfonyl chloride (10.9 mL, 90 mmol) was added slowly. The reaction mixture was stirred for an additional 1 h and then poured into 150 mL of 5% aq. NaHCO₃ and extracted with ether (3×150 mL). The combined organic layers were dried (Na₂SO₄), and the solvent was removed under reduced pressure to give a beige solid. Recrystallization from ethanol afforded the title compound as colorless crystals.

4-Nitro-1-(phenylsulfonyl)-1H-indole (14a)

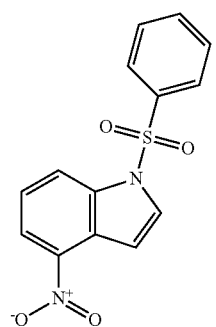

Lit.: (Johansson, Brandt et al. 2005) Preparation from 13a (Maybride) as described in the general procedure 1. Yield: 7.86 g, 26 mmol (95%). $^1$H NMR (DMSO-$d_6$): δ=8.45 (d, J=8.3 Hz, 1H), 8.27-8.18 (m, 2H), 8.15-8.03 (m, 2H), 7.74 (ddd, J=6.6, 3.8, 1.2 Hz, 1H), 7.62 (dd, J=15.7, 8.0 Hz, 3H), 7.36 (dd, J=3.7, 0.6 Hz, 1H).

5-Nitro-1-(phenylsulfonyl)-1H-indole (14b)

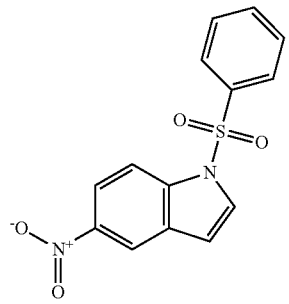

Lit.: (Wagner, Wittmann et al. 2011) Preparation from 13b as described in the general procedure 1. Yield: 4.83 g, 16 mmol (31%). $^1$H NMR (DMSO-$d_6$): δ=8.59 (d, J=1.9 Hz, 1H), 8.27-8.14 (m, 2H), 8.12-8.03 (m, 3H), 7.74 (ddd, J=6.7, 3.8, 1.2 Hz, 1H), 7.66-7.58 (m, 2H), 7.09 (d, J=3.6 Hz, 1H).

6-Nitro-1-(phenylsulfonyl)-1H-indole (14c)

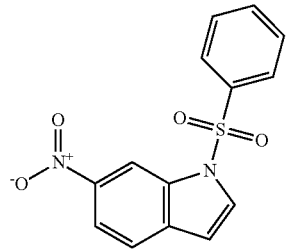

Lit.: (Pelkey and Gribble 1999) Preparation from 13c as described in the general procedure 1. Yield: 13.3 g, 44 mmol (77%). $^1$H NMR (DMSO-$d_6$): δ=8.75 (d, J=2.0 Hz, 1H), 8.24 (d, J=3.6 Hz, 1H), 8.13 (dd, J=8.7, 2.1 Hz, 1H), 8.09-8.00 (m, 2H), 7.85 (d, J=8.7 Hz, 1H), 7.73 (ddd, J=6.6, 3.8, 1.1 Hz, 1H), 7.67-7.56 (m, 2H), 7.06 (dd, J=3.7, 0.6 Hz, 1H).

7-Nitro-1-(phenylsulfonyl)-1H-indole (14d)

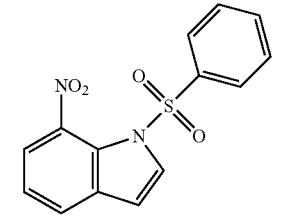 [SMILES: O=[N+]([O-])c1cccc2ccn(S(=O)(=O)c3ccccc3)c12]

Preparation from 13b (Sigma Aldrich) as described in the general procedure 1. Yield: 50 mmol (83%). $^1$H NMR (DMSO-$d_6$): δ=8.75 (s, 1H), 7.83 (d, J=3.8 Hz, 1H), 7.74 (dd, J=7.5, 6.1 Hz, 2H), 7.66 (dt, J=4.1, 2.6 Hz, 1H), 7.60-7.52 (m, 2H), 7.34 (dd, J=7.7, 1.0 Hz, 1H), 7.22 (d, J=7.8 Hz, 1H), 6.90 (t, J=5.3 Hz, 1H). Anal. ($C_{14}H_{10}N_2O_4S$): Cal.: C, 55.62, H, 3.33, N, 9.27, S, 10.61. Found: C, 55.40, H, 3.31, N, 9.35, S, 10.59.

5-Nitro-1-(phenylsulfonyl)-1H-pyrrolo[2,3-b]pyridine (14e)

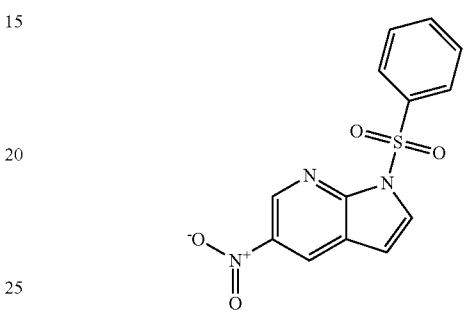

Lit.: (Vanotti, Angelucci et al. 2007) Preparation from 13e as follows: 13e (18.0 g, 80 mmol) was dissolved in DMF and cooled to 0° C. After addition of NaOH (7.7 g, 190 mmol), Bu$_4$N$^+$HSO$_4^-$ (0.20 g, 60 mmol) and benzenesulfonyl chloride (10.5 mL, 80 mmol), the reaction was stirred overnight at rt. After TLC control the reaction mixture was poured into H$_2$O and extracted with EtOAc (3×200 mL). The combined organic layers were dried (Na$_2$SO$_4$) and the solvent was removed under reduced pressure to give 14e. Recrystallization from ethanol afforded colorless crystals. Yield: 18.0 g, 56 mmol (74%). $^1$H NMR (DMSO-$d_6$): δ=9.20 (d, J=2.5 Hz, 1H), 8.95 (d, J=2.5 Hz, 1H), 8.18 (t, J=2.8 Hz, 2H), 8.15 (d, J=1.4 Hz, 1H), 7.81-7.72 (m, 1H), 7.69-7.62 (m, 2H), 7.05 (d, J=4.0 Hz, 1H).

tert-Butyl (1-(phenylsulfonyl)-1H-pyrrolo[2,3-c]pyridin-5-yl)carbamate (16f)

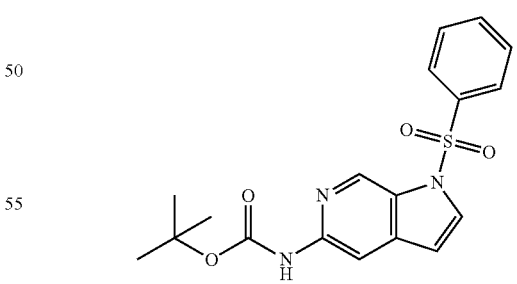

Preparation from tert-butyl 1H-pyrrolo[2,3-c]pyridin-5-ylcarbamate (20) (Andaloussi, Moreau et al. 2007) as described in the general procedure 1. Yield: 5.23 g, 14 mmol (64%). Mp: 138-143° C. $^1$H NMR (DMSO-$d_6$): δ=9.74 (s, 1H), 8.84 (s, 1H), 8.04 (s, 1H), 8.02 (t, J=1.7 Hz, 1H), 7.99 (d, J=3.6 Hz, 1H), 7.96 (d, J=1.0 Hz, 1H), 7.76-7.68 (m, 1H), 7.60 (dd, J=10.4, 4.8 Hz, 2H), 6.88 (d, J=3.5 Hz, 1H), 1.46 (s, 9H). IR (KBr): ν (cm$^{-1}$)=3057, 1673. ESI-MS (70 eV)

m/z (%): 374.12 (100) [MH⁺]. Anal. (C₉H₁₀N₂O): Cal.: C, 57.89, H, 5.13, N, 11.25, S, 8.59. Found: C, 58.20, H, 5.27, N, 10.99, S, 8.38.

Reduction of the Nitro-Aryl Derivatives by Use of Zn-Dust/HCl—General Procedure 2—Synthesis of 15a-e The corresponding nitroindole or nitropyrrolopyridine (62.0 mmol) was dissolved in a mixture of THF:MeOH (200 mL:100 mL). Zn-dust (30.0 g) and $CuSO_4$ (1.0 g) was added and 3M HCl (150 mL) was dropwise added by a dropping funnel. After complete addition of HCl the reaction was stirred for 1 h. The mixture was filtered, alkalized with conc. $NH_3$ and extracted with DCM (3×150 mL). The combined organic layers were dried ($Na_2SO_4$) and the solvent was removed under reduced pressure to give the corresponding aminoindole or aminopyrrolopyridine.

1-(Phenylsulfonyl)-1H-indol-4-amine (15a)

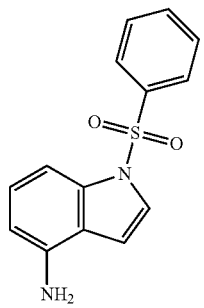 [SMILES: Nc1cccc2c1ccn2S(=O)(=O)c1ccccc1]

Lit.: (Johansson, Brandt et al. 2005) Preparation from 14a according to general procedure 2. Yield: 6.54 g, 24 mmol (98%). ¹H NMR (DMSO-d₆): δ=7.94-7.82 (m, 2H), 7.67 (ddd, J=6.5, 3.8, 1.2 Hz, 1H), 7.62-7.51 (m, 3H), 7.08 (d, J=8.2 Hz, 1H), 6.97 (dd, J=13.5, 5.7 Hz, 2H), 6.35 (d, J=7.7 Hz, 1H), 5.56 (d, J=5.2 Hz, 2H).

1-(Phenylsulfonyl)-1H-indol-5-amine (15b)

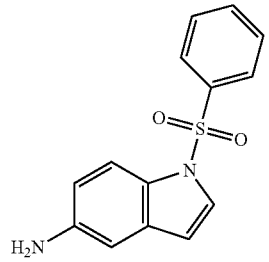 [SMILES: Nc1ccc2c(ccn2S(=O)(=O)c2ccccc2)c1]

Lit.: (Wagner, Wittmann et al. 2011). Prepared from 14a according to general procedure 2. Yield: 3.54 g, 13 mmol (81%). ¹H-NMR (DMSO-d₆): δ=7.89 (s, 1H), 7.86 (t, J=1.7 Hz, 1H), 7.67 (dt, J=4.4, 1.6 Hz, 1H), 7.65-7.59 (m, 2H), 7.55 (ddd, J=7.8, 4.7, 3.0 Hz, 3H), 6.63 (d, J=1.8 Hz, 1H), 6.61-6.56 (m, 1H), 4.97 (s, 2H).

1-(Phenylsulfonyl)-1H-indol-6-amine (15c)

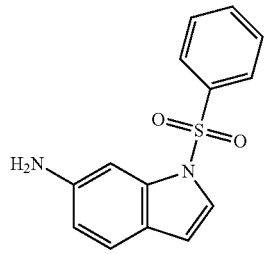 [SMILES: Nc1ccc2ccn(S(=O)(=O)c3ccccc3)c2c1]

Preparation from 14c according to general procedure 2. Yield: 6.5 g, 24 mmol (87%) brown oil. ¹H NMR (DMSO-d₆): δ=8.05-7.79 (m, 2H), 7.71-7.51 (m, 3H), 7.39 (d, J=3.6 Hz, 1H), 7.24-7.12 (m, 2H), 6.57 (qd, J=8.5, 1.8 Hz, 2H), 5.30 (s, 2H).

1-(Phenylsulfonyl)-1H-indol-7-amine (15d)

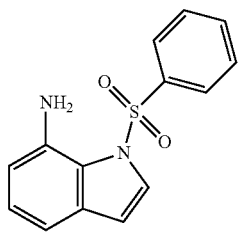 [SMILES: Nc1cccc2ccn(S(=O)(=O)c3ccccc3)c12]

Preparation from 14d according to general procedure 2. Yield: 13.07 g, 48 mmol (96%) as brown oil. ¹H NMR (DMSO-d₆): δ=7.83 (dt, J=3.6, 2.6 Hz, 2H), 7.68-7.44 (m, 4H), 7.02-6.91 (m, 1H), 6.76 (dd, J=9.2, 2.4 Hz, 2H), 6.67 (dd, J=7.8, 1.0 Hz, 1H), 5.88 (s, 2H). IR (KBr): ν (cm⁻¹) =3473, 3383, 3046, 1621, 1594.

1-(Phenylsulfonyl)-1H-pyrrolo[2,3-b]pyridin-5-amine (15e)

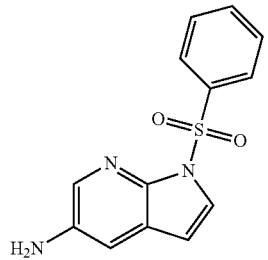 [SMILES: Nc1cnc2c(ccn2S(=O)(=O)c2ccccc2)c1]

Lit.: (Berthel, Chen et al. 2011). Preparation from 14e according to general procedure 2. Yield: 3.82 g, 14 mmol (90%). ¹H-NMR (DMSO-d₆): δ=8.11-7.92 (m, 2H), 7.76 (t, J=8.8 Hz, 1H), 7.71-7.62 (m, 2H), 7.62-7.53 (m, 2H), 7.09 (t, J=3.3 Hz, 1H), 6.59 (d, J=4.0 Hz, 1H), 5.17 (s, 2H, $NH_2$).

Synthesis of Tert-Butyl Carbamates 16a-16e—General Procedure 3

The corresponding aminoindole or aminopyrrolopyridine (24 mmol) was dissolved in THF (100 mL) and cooled to 0°

C. After addition of di-tert-butyl dicarbonate (1.2 equiv., 6.3 g) and a catalytical amount of DMAP, the reaction solution was allowed to warm to rt overnight. The completion of the reaction was controlled by TLC (PE:DCM 2:1). By addition of diethylamine (1.2 equiv., 3 mL) the reaction was stopped and after 1 h the reaction was poured into $H_2O$. After extraction with EtOAc (3×100 mL) the combined organic layers were dried ($Na_2SO_4$) and the solvent was removed under reduced pressure to give the respective tert-butyl carbamates.

tert-Butyl (1-(phenylsulfonyl)-1H-indol-4-yl)carbamate (16a)

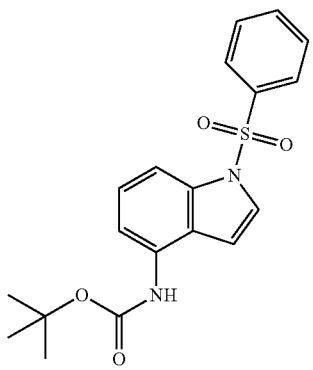 [SMILES: CC(C)(C)OC(=O)Nc1cccc2c1ccn2S(=O)(=O)c1ccccc1]

Preparation from 15a as described in general procedure 3. Yield: 8.57 g, 23 mmol (61%). Mp: 172.8° C. 1H NMR (DMSO-$d_6$): δ=7.97 (dd, J=8.2, 6.9 Hz, 2H), 7.90 (d, J=8.3 Hz, 1H), 7.83 (d, J=3.7 Hz, 1H), 7.69 (t, J=7.4 Hz, 1H), 7.59 (t, J=7.5 Hz, 2H), 7.29 (t, J=8.1 Hz, 1H), 7.04 (t, J=10.3 Hz, 1H), 6.66 (d, J=3.2 Hz, 1H), 1.21 (d, J=8.5 Hz, 9H).

tert-Butyl (1-(phenylsulfonyl)-1H-indol-5-yl)carbamate (16b)

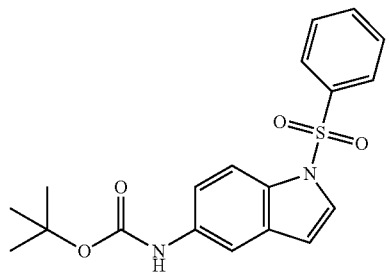 [SMILES: CC(C)(C)OC(=O)Nc1ccc2c(ccn2S(=O)(=O)c2ccccc2)c1]

Lit.: (Wagner, Wittmann et al. 2011). Preparation from 15b as described in general procedure 3. Yield: 4.50 g, 12 mmol (93%). $^1$H-NMR (DMSO-$d_6$): δ=9.38 (s, 1H), 7.93 (dd, J=5.3, 3.4 Hz, 2H), 7.79 (t, J=9.1 Hz, 1H), 7.75-7.64 (m, 3H), 7.56 (dd, J=10.4, 4.8 Hz, 2H), 7.35 (dd, J=9.0, 2.0 Hz, 1H), 6.78 (d, J=3.7 Hz, 1H), 1.46 (s, 9H).

tert-butyl (1-(Phenylsulfonyl)-1H-indol-6-yl)carbamate (16c)

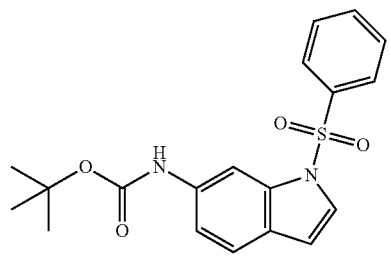 [SMILES: CC(C)(C)OC(=O)Nc1ccc2ccn(S(=O)(=O)c3ccccc3)c2c1]

Preparation from 15c as described in general procedure 3. Yield: 2.35 g, 6.3 mmol (26%) Mp: 168.8-170.2° C. IR (KBr): ν ($cm^1$)=3311, 2980, 1695, 1596, 1542, 1172. $^1$H NMR (DMSO-$d_6$): d=9.37 (s, 1H), 7.93 (m, 2H), 7.81 (d, J=8.9 Hz, 1H), 7.73 (m, 2H), 7.67 (m, 1H), 7.57 (m, 2H), 7.35 (dd, J=2.0 Hz, J=9.0 Hz, 1H), 6.78 (d, J=3.6 Hz, 1H), 1.46 (s, 9H). EI-MS (70 eV) m/z (%): 373 (100) [$M^{+-}$]. Anal. ($C_{19}H_{20}N_2O_4S$): Cal.: C, 61.27, H, 5.41, N, 7.52. Found: C, 61.40, H, 5.49, N, 7.43.

tert-Butyl (1-(phenylsulfonyl)-1H-indol-7-yl)carbamate (16d)

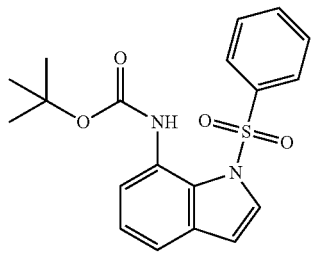 [SMILES: CC(C)(C)OC(=O)Nc1cccc2ccn(S(=O)(=O)c3ccccc3)c12]

Preparation from 15e as described in general procedure 3. Yield: 7.45 g, 20 mmol (81%). $^1$H NMR (DMSO-$d_6$): δ=7.99-7.84 (m, 4H), 7.72-7.62 (m, 2H), 7.56 (dd, J=10.5, 4.8 Hz, 2H), 7.22 (ddd, J=6.7, 5.1, 1.6 Hz, 1H), 6.94-6.87 (m, 1H), 1.37 (s, 9H).

tert-Butyl (1-(phenylsulfonyl)-1H-pyrrolo[2,3-b]pyridin-5-yl)carbamate (16e)

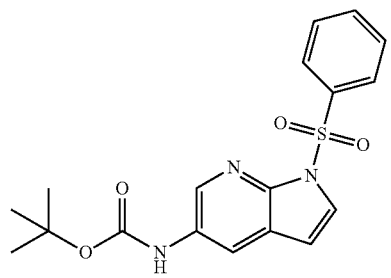 [SMILES: CC(C)(C)OC(=O)Nc1cnc2c(ccn2S(=O)(=O)c2ccccc2)c1]

Preparation from 15e as described in general procedure 3. (Berthel, Chen et al. 2011) Yield: 4.48 g, 12 mmol (86%). $^1$H-NMR (DMSO-$d_6$): δ=8.32 (d, J=2.3 Hz, 1H), 8.15-8.08

(m, 2H), 8.06 (d, J=2.4 Hz, 1H), 7.99 (d, J=4.0 Hz, 1H), 7.72 (t, J=7.4 Hz, 1H), 7.61 (t, J=7.6 Hz, 2H), 6.89 (d, J=4.0 Hz, 1H), 1.35 (s, 9H).

tert-Butyl (4-methyl-5-nitropyridin-2-yl)carbamate (18)

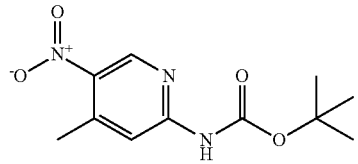

Preparation from 4-methyl-5-nitropyridin-2-amine (17) according literature (Lougiakis, Marakos et al. 2008). Yield: 3.80 g, 15 mmol (45%). $^1$H-NMR (DMSO-d$_6$): δ=10.56 (s, 1H), 8.92 (s, 1H), 7.88 (s, 1H), 2.58 (s, 3H), 1.49 (s, 9H).

(E)-tert-Butyl (4-(2-(dimethylamino)vinyl)-5-nitropyridin-2-yl)carbamate (19)

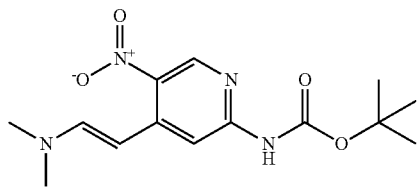

19 was prepared from 18 as follows: 18 (7.3 g, 29 mmol) was dissolved in DMF and treated with DMFDMA (32 mmol) and 2 mL of pyrrolidine. The reaction was stirred for 30 min at 60° C. After cooling down to 0° C., the reaction was poured into H$_2$O, the product filtered off and dried. The product was further processed after NMR monitoring without any purification. Yield: 8.0 g, 26 mmol (90%). $^1$H-NMR (DMSO-d$_6$): δ=9.97 (s, 1H), 8.71 (s, 1H), 7.86 (s, 1H), 7.78 (d, J=13.1 Hz, 1H), 5.89 (d, J=13.1 Hz, 1H), 1.91 (s, 43H), 1.48 (s, 9H), 1.23 (s, 3H).

tert-Butyl 1H-pyrrolo[2,3-c]pyridin-5-ylcarbamate (20)

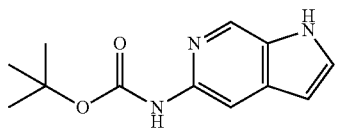 [SMILES: CC(C)(C)OC(=O)Nc1cc2cc[nH]c2cn1]

19 was dissolved in MeOH:THF 2:1 and Pd/C (10%) was added. The mixture was stirred overnight (70° C., 40 bar H$_2$). The catalyst was filtered off and the solvent was removed under reduced pressure. The crude product was purified by cc (EtOAc:DCM 10:1) to give 20. Yield: 1.1 g, 4.7 mmol (59%). $^1$H-NMR (DMSO-d$_6$): δ=11.41 (s, 1H), 9.44 (s, 1H), 8.45 (s, 1H), 7.88 (s, 1H), 7.55 (d, J=2.8 Hz, 1H), 6.50-6.36 (m, 1H), 1.48 (s, 9H). Mp: 192.5-206.7° C. IR (KBr): ν (cm$^{-1}$)=3305, 2983, 1622. ESI-MS (70 eV) m/z (%): 233.9 (100) [MH$^+$]. Anal. (C$_{12}$H$_{15}$N$_3$O$_2$): Cal.: C, 61.79, H, 6.48, N, 18.01. Found: C, 61.80, H, 6.65, N, 17.98.

Reaction Sequence for Synthesis of 28 (Marbotinib)

1-(5-Benzyloxy-1-phenylsulfonyl-1H-indol-2-yl)ethan-1-one (22)

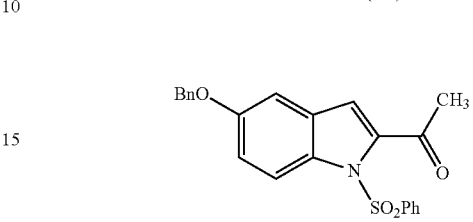

22 was prepared from 5-(benzyloxy)-1-(phenylsulfonyl)-1H-indole (21) (Mahboobi, Uecker et al. 2007) according to literature (Jiang and Gribble 2002). Yield: 10.2 g (28 mmol, 89%) colorless solid after crystallization from EtOH. Mp. 155.6-159.1° C. IR (KBr): ν (cm$^{-1}$)=1672, 1530. $^1$H-NMR (300 MHz, DMSO-d$_6$): δ=7.97 (d, J=9.2 Hz, 1H, ArH), 7.91 (s, 1H, ArH), 7.89 (t, J=1.7 Hz, 1H, ArH), 7.74-7.66 (m, 1H, ArH), 7.59 (dd, J=10.4, 4.8 Hz, 2H, ArH), 7.51 (s, 1H, ArH), 7.49-7.43 (m, 2H, ArH), 7.43-7.30 (m, 3H, ArH), 7.27 (d, J=2.5 Hz, 1H, ArH), 7.20 (dd, J=9.1, 2.6 Hz, 1H, ArH), 5.13 (s, 2H, O—CH$_2$-Ph), 2.59 (s, 3H, CH$_3$). ESI-MS (120 eV) m/z (%): 406.1 (100) [MH$^+$]. Anal. (C$_{23}$H$_{19}$NO$_4$S): Calcd. C, 68.13, H, 4.72, N, 3.45, S, 7.91. Found. C, 67.98, H, 4.76, N, 3.37, S, 7.71.

1-(5-Benzyloxy-1-phenylsulfonyl-1H-indol-2-yl)-2-bromethan-1-one (23)

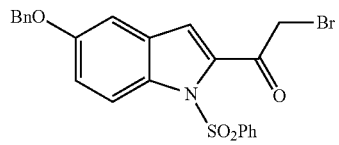

A mixture of CuBr$_2$ (1.12 g, 5.0 mmol, 2.0 equiv.), ethyl acetate (20 mL) and HBr (10 drops, 72%) was heated till reflux. To this mixture a solution of 22 (1.0 g, 2.5 mmol) in CHCl$_3$ (10 mL) was added dropwise. After consumption of the starting material (TLC control) the mixture was filtered over a pad of celite, the organic layer first washed with water (2×10 mL), then with an aqueous NaHCO$_3$-solution (2×10 mL; 5%) and finally with brine 10 mL). The organic layer was dried (Na$_2$SO$_4$) and the solvent removed under reduced pressure. Yield 0.44 g (0.9 mmol, 36%) beige solid from EtOH. Mp. 139.9-141.4° C. IR (KBr): ν (cm$^{-1}$)=3454, 1672, 1530. $^1$H-NMR (300 MHz, DMSO-d$_6$): δ=8.01 (ddd, J=14.1, 9.0, 3.2 Hz, 3H, ArH), 7.79-7.70 (m, 2H, ArH), 7.63 (td, J=7.6, 4.2 Hz, 2H, ArH), 7.48 (t, J=7.0 Hz, 3H, ArH), 7.44-7.32 (m, 4H, ArH), 5.27 (s, 2H, O—CH$_2$-Ph), 5.02 (s, 2H, CH$_2$). ESI-MS (120 eV) m/z (%): 484.02 $^{79}$BrC$_{23}$H$_{18}$NO$_4$S (91) [MH$^+$]. 486.02 $^{81}$BrC$_{23}$H$_{18}$NO$_4$S (90) [MH$^+$] (MW=483.01 g/mol). Anal. (C$_{23}$H$_{18}$BrNO$_4$S): Calcd. C, 57.03, H, 3.75, N, 2.89, S, 6.62. Found. C, 57.04, H, 3.76, N, 2.62, S, 6.51.

(5-Benzyloxy-1H-indol-2-yl)(5-nitrobenzofuran-2-yl)methanone (25)

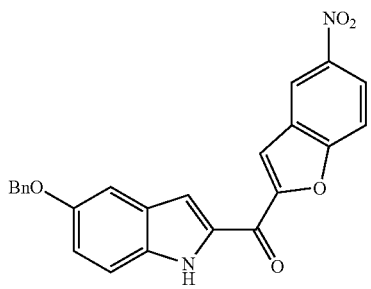 [SMILES: O=C(c1cc2cc(OCc3ccccc3)ccc2[nH]1)c1cc2cc([N+](=O)[O-])ccc2o1]

A mixture of 2-hydroxy-5-nitrobenzaldehyde (24) (0.38 g, 2.3 mmol), $K_2CO_3$ (0.32 g, 2.3 mmol) and 1-(5-benzyloxy-1-phenylsulfonyl-1H-indol-2-yl)-2-bromethan-1-one (23) (1.11 g, 2.3 mmol) in 2-butanone (20.0 mL) was heated till reflux for 4 h. The mixture was filtered and the solvent removed under reduced pressure. The crude solid obtained this way was dissolved in a mixture of in THF/MeOH/NaOH$_{aqu.}$ (10%) 1:1:1 (v/v/v) and heated to reflux for 2 h. Water was added (20 mL), the organic solvents removed under reduced pressure, the precipitating product removed by filtration, washed with water and dried. Yield 0.25 g (0.6 mmol, 27% over 2 steps) after cc (SiO$_2$; light petrol, ethyl acetate 5:2) and crystallization from CH$_2$Cl$_2$/MeOH. Mp. 278.2-281.1° C. IR (KBr): ν (cm$^{-1}$)=3292, 2862, 1610, 1557. $^1$H-NMR (300 MHz, DMSO-d$_6$): δ=12.08 (s, 1H, Indole-NH), 8.83 (d, J=2.4 Hz, 1H, ArH), 8.44 (dd, J=9.1, 2.5 Hz, 1H, ArH), 8.18 (s, 1H, ArH), 8.09 (d, J=9.2 Hz, 1H, ArH), 7.76 (s, 1H, ArH), 7.49 (d, J=6.8 Hz, 2H, ArH), 7.45-7.27 (m, 5H, ArH), 7.12 (dd, J=9.0, 2.4 Hz, 1H, ArH), 5.15 (s, 2H, O—CH$_2$-Ph). ESI-MS (120 eV) m/z (%): 413.1 (100) [MH$^+$] (MW=412.11 g/mol). Anal. (C$_{24}$H$_{16}$N$_2$O$_5$): Calcd. C, 69.90, H, 3.91, N, 6.79. Found. C, 69.72, H, 3.95, N, 6.74.

(5-Aminobenzofuran-2-yl)(5-hydroxy-1H-indol-2-yl)methanone (26)

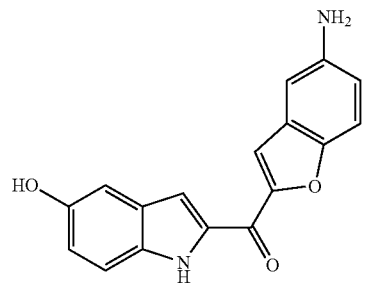 [SMILES: Nc1ccc2oc(C(=O)c3cc4cc(O)ccc4[nH]3)cc2c1]

(5-Benzyloxy-1H-indol-2-yl)(5-nitrobenzofuran-2-yl)methanone (25) (0.40 g, 0.97 mmol) was dissolved in in THF:MeOH (150 mL) (2:1) and ammonium formate (0.24 g, 3.88 mmol) and Pd (40 mg, 10% on charcoal) was added. The mixture was heated to reflux till TLC indicated complete consumption of the starting material. The mixture was filtered over a pad of celite, the solution poured into water (100 mL) and the organic solvents removed under reduced pressure till the product precipitates. Yield 0.10 g (0.34 mmol, 35% light yellow solid) after cc (SiO$_2$, CH$_2$Cl$_2$, MeOH 20:1) and crystallization from DMSO. Mp. 228.4-231.2° C. IR (KBr): ν (cm$^{-1}$)=3453, 1612, 1518. $^1$H-NMR (300 MHz, DMSO-d$_6$): δ=11.74 (s, 1H, Indole-NH), 9.04 (s, 1H, OH), 7.75 (d, J=0.7 Hz, 1H, ArH), 7.58 (d, J=1.5 Hz, 1H, ArH), 7.47 (m, 1H, ArH), 7.31 (m, 1H, ArH), 7.01 (d, J=2.2 Hz, 1H, ArH), 6.88 (dd, J=4.8, 2.2 Hz, 1H, ArH), 6.86 (d, J=2.5 Hz, 2H, ArH), 5.12 (s, 2H, NH$_2$). ESI-MS (120 eV) m/z (%): 293.1 (100) [MH$^+$]. HR-MS (120 eV) m/z: Cacd. 293.0921. Found. 293.0924 (C$_{17}$H$_{13}$N$_2$O$_3$) [MH$^+$]. Anal. (C$_{17}$H$_{17}$N$_2$O$_3$×0.4 DMSO): Cacd. C, 66.08, H, 4.49, N, 8.66. Found. C, 66.04, H, 4.73, N, 8.14.

1-(5-(tert-butyl)isoxazol-3-yl)-3-(2-(5-hydroxy-1H-indole-2-carbonyl)benzofuran-5-yl)urea (28) (Marbotinib)

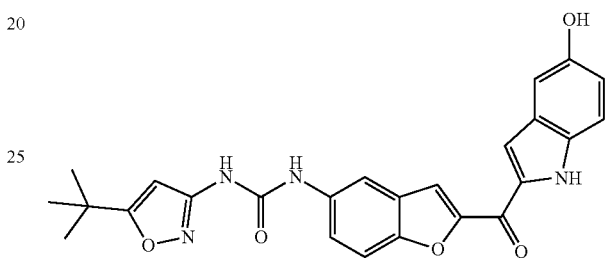

Step A. 5-tert-Butyl-3-isoxazolyl Isocyanate (27a) was prepared according to Lit. (Dumas, Khire et al. 2012) as follows: To a solution of phosgene (1.5 mL, 2.0 M in toluene, 3.0 mmol) in anhydrous CH$_2$Cl$_2$ (10 mL) was added 3-amino-5-tert-butylisoxazole (0.10 g, 0.71 mmol) followed by pyridine (0.5 mL). The mixture was allowed to warm to room temp and stirred overnight (ca. 16 h), then the mixture was concentrated in vacuo. The residue was dissolved in anh. THF (7 mL) and stirred for 10 min. The orange precipitate (pyridinium hydrochloride) was removed and the isocyanate-containing filtrate (approximately 0.1 M in THF) was used as a stock solution.

Step B. (5-Aminobenzofuran-2-yl)(5-hydroxy-1H-indol-2-yl)methanone (26) (0.1 g, 0.34 mmol) was dissolved in a sealed tube under nitrogen atmosphere in the isocyanate-containing stock solution (6.8 mL, 0.64 mmol) and pyridine (0.64 mL) was added. The mixture was stirred at room temperature overnight, poured into water (20.0 mL) and the yellow precipitate removed by filtration. Column chromatograpy (SiO$_2$, CH$_2$Cl$_2$/MeOH; 20:1) and crystallization from ethyl acetate afforded the desired product as yellow crystals. Yield 0.077 g (0.17 mmol, 50%. Mp. 171.2-173.7° C. (Decomposition). IR (KBr): ν (cm$^{-1}$)=3454, 1636, 1577. $^1$H-NMR (300 MHz, DMSO-d$_6$): δ=11.81 (s, 1H, Indole-NH), 9.57 (s, 1H, NH), 9.07 (s, 1H, NH), 8.98 (s, 1H, OH), 8.07 (d, J=2.1 Hz, 1H, ArH), 7.96 (s, 1H, ArH), 7.76 (d, J=8.9 Hz, 1H, ArH), 7.64 (s, 1H, ArH), 7.50 (dd, J=9.0, 2.2 Hz, 1H, ArH), 7.33 (d, J=8.8 Hz, 1H, ArH), 7.03 (s, 1H, ArH), 6.90 (dd, J=8.8, 2.3 Hz, 1H, ArH), 6.53 (s, 1H, Isoxazole-CH), 1.31 (s, 9H, (CH$_3$)$_3$). $^{13}$C-NMR (101 MHz, DMSO-d$_6$): δ=180.6 (C$_q$). 180.2 (C$_q$), 173.1 (C$_q$), 158.4 (C$_q$), 157.9 (C$_q$), 153.0 (C$_q$), 151.6 (C$_q$), 135.3 (C$_q$), 133.9 (C$_q$), 133.2 (C$_q$), 128.0 (C$_q$), 127.2 (C$_q$), 120.7 (+, CH), 118.1 (+, CH), 114.3 (+, CH), 113.4 (+, CH), 112.5 (+, CH), 112.0 (+, CH), 110.3 (+, CH), 105.0 (+, CH), 92.5 (+, CH, Isoxazole-CH), 28.4 (+, (CH$_3$)$_3$). ESI-MS (120 eV) m/z (%): 459.2 (100) [MH$^+$] (MW=458.16 g/mol). Anal.

Carbonyl Chlorides 29a-c

4-Methyl-1-(phenylsulfonyl)-1H-indole-2-carboxylic acid

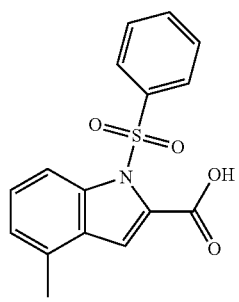 [SMILES: Cc1cccc2c1cc(C(=O)O)n2S(=O)(=O)c1ccccc1]

Preparation from 4-methyl-1-(phenylsulfonyl)-1H-indole analogues literature (Mahboobi, Uecker et al. 2006). Yield: 20.5 g, 65.1 mmol (88%). Mp: 155.2-156.1° C. IR (KBr): ν (cm$^{-1}$)=2918, 1702, 1548, 1169. $^1$H-NMR (DMSO-d$_6$): δ (ppm)=2.44 (s, 3H), 7.11 (d, 1H, J=7.3 Hz), 7.35 (dd, 1H, J=7.5 Hz, J=8.4 Hz), 7.40 (d, 1H, J=0.6 Hz), 7.61 (m, 2H), 7.71 (m, 1H), 7.83 (d, 1H, J=8.5 Hz), 8.02 (m, 2H), 13.58 (s, 1H). +p ESI-MS m/z (%): 316 (20) [M+H]$^+$, 357 (100) [M+NH$_4^+$]$^+$. −p ESI-MS m/z (%): 314 (5) [M−H]$^-$, 629 (100) [2M−H]$^-$, 360 (35) [M+HCOO$^-$]$^-$. Anal. (C$_{16}$H$_{13}$NO$_4$S): Cal.: C, 60.94, H, 4.16, N, 4.44, S, 10.17. Found: C, 60.83, H, 4.25, N, 4.24, S, 10.13.

4-Methyl-1-(phenylsulfonyl)-1H-indole-2-carbonyl chloride (29a)

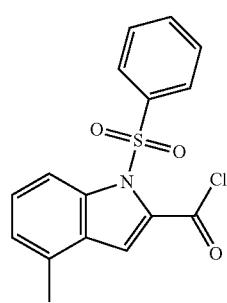 [SMILES: Cc1cccc2c1cc(C(=O)Cl)n2S(=O)(=O)c1ccccc1]

Preparation from 4-methyl-1-(phenylsulfonyl)-1H-indole-2-carboxylic acid analogues literature (Mahboobi, Uecker et al. 2006). IR (KBr): ν (cm$^{-1}$)=3106, 1763. Mp: 116.0-118.0° C.

5-(Benzyloxy)-1-(phenylsulfonyl)-1H-indole-2-carbonyl chloride (29b)

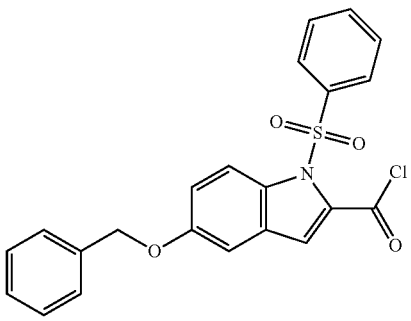 [SMILES: O=C(Cl)c1cc2cc(OCc3ccccc3)ccc2n1S(=O)(=O)c1ccccc1]

Preparation analogues lit. (Mahboobi, Uecker et al. 2006).

5-(Benzyloxy)benzofuran-2-carbonyl Chloride (29c)

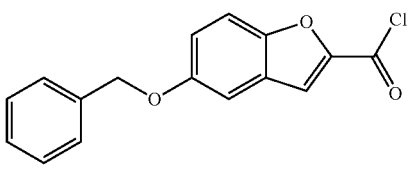 [SMILES: O=C(Cl)c1cc2cc(OCc3ccccc3)ccc2o1]

Preparation analogues literature (Mahboobi, Sellmer et al. 2007).

Preparation of Aryl-Methanone Derivatives—Synthesis of 30a-d and 32e-i tert-Butyl (2-(5-(benzyloxy)-1H-indole-2-carbonyl)-1H-indol-5-yl)carbamate (32e)

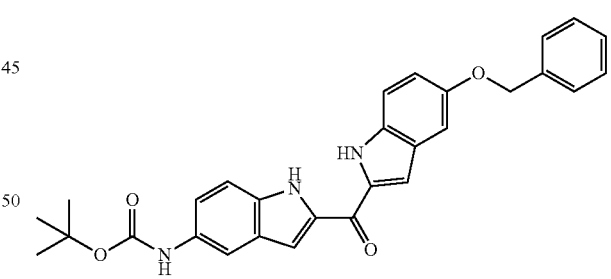

A solution of tert-butyl 1-(phenylsulfonyl)-1H-indol-5-ylcarbamate (16b) (3.72 g, 10.0 mmol) in THF (100 mL) was cooled to −78° C. in a nitrogen atmosphere and 2.1 equiv. $^t$Buli (21.0 mmol 1.6 M in pentane) were added drop wise whilst stirring. The mixture was allowed to warm up to −20° C. within 3-4 hours, cooled to −78° C. again and a −78° C. cold solution of 5-(benzyloxy)-1-(phenylsulfonyl)-1H-indole-2-carbonyl chloride (29b) (10.0 mmol; 4.25 g) in THF (50.0 mL) was added at once. The mixture was stirred for half an hour, put into water whilst stirring, extracted with ethyl acetate (3×50 mL) and the solvent removed under reduced pressure. The resulting crude product was dissolved in THF (100 mL), MeOH (100 mL) and aqueous NaOH (C$_{25}$H$_{22}$N$_4$O$_5$×0.33 EtOAc): Cacd. C, 64.88, H, 5.03, N, 11.49. Found. C, 64.67, H, 5.13, N, 11.21.

(10%; 100 mL) were added and the mixture warmed till reflux for 2 h. The organic solvent was removed under reduced pressure, the precipitated product removed by filtration or extraction with ethyl acetate, crude purified by cc (CH$_2$Cl$_2$, ethyl acetate 6:1; dry load method) and crystallized from CH$_2$Cl$_2$ by dissolving and removing most of the solvent under reduced pressure. Yield: 1.65 g, 3.4 mmol (73%). Mp: 215.7-217.9° C. IR (KBr): ν (cm$^{-1}$)=3451, 3278, 2978, 1665, 1527. $^1$H-NMR (DMSO-d$_6$): δ=11.87 (s, 1H), 9.25 (s, 1H), 7.87 (s, 1H), 7.47 (dd, J=11.9, 9.0 Hz, 4H), 7.45-7.39 (m, 4H), 7.40-7.29 (m, 2H), 7.26 (d, J=2.2 Hz, 1H), 7.05 (dd, J=8.9, 2.3 Hz, 1H), 5.14 (s, 2H), 1.49 (s, 9H). ESI-MS (70 eV) m/z (%): 482.0 (100) [MH$^+$]. Anal. (C$_{29}$H$_{27}$N$_3$O$_4$): Cal.: C, 72.33, H, 5.65, N, 8.73. Found: C, 72.22, H, 5.83, N, 8.75. Cc: DCM:EtOAc 5:1.

tert-Butyl (2-(4-methyl-1H-indole-2-carbonyl)-1H-indol-4-yl)carbamate (30a)

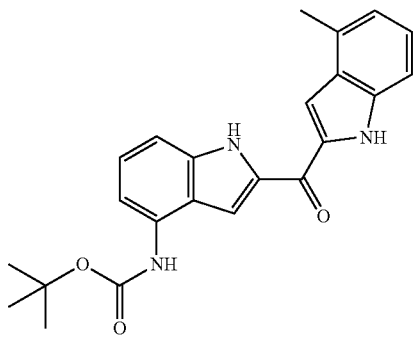 [SMILES: Cc1cccc2[nH]c(C(=O)c3cc4c(NC(=O)OC(C)(C)C)cccc4[nH]3)cc12]

Preparation from tert-butyl 1-(phenylsulfonyl)-1H-indol-4-ylcarbamate (16a) and 4-methyl-1-(phenylsulfonyl)-1H-indole-2-carbonyl chloride (29a) as described above. Yield: 3.70 g, 9.50 mmol (34%). Mp: 216.3° C. IR (KBr): ν (cm$^{-1}$)=3459, 3320, 1690. $^1$H-NMR (DMSO-d$_6$): d=11.94 (s, 2H), 9.36 (s, 1H), 8.03 (s, 1H), 7.67-7.47 (m, 2H), 7.33 (d, J=8.3 Hz, 1H), 7.19 (m, 3H), 6.92 (d, J=7.0 Hz, 1H), 2.62 (s, 3H), 1.54 (s, 9H). EI-MS (70 eV) m/z (%): 390.2 (45) [MH$^+$]. Anal. (C$_{22}$H$_{23}$N$_3$O$_3$): Cal.: C, 70.93, H, 5.95, N, 10.79. Found: C, 70.84, H, 6.14, N, 10.82. Cc: DCM:EtOAc 6:1.

tert-Butyl (2-(4-methyl-1H-indole-2-carbonyl)-1H-indol-5-yl)carbamate (30b)

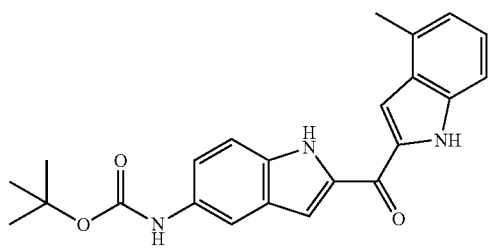 [SMILES: Cc1cccc2[nH]c(C(=O)c3cc4cc(NC(=O)OC(C)(C)C)ccc4[nH]3)cc12]

Preparation from and 4-methyl-1-(phenylsulfonyl)-1H-indole-2-carbonyl chloride (29a) and tert-butyl 1H-indol-5-ylcarbamate (16b) as described above. Yield: 0.40 g, 1.0 mmol (33%). Mp: 279.5° C. IR (KBr): ν (cm$^{-1}$)=3467, 3358, 3284, 1696, 1580, 1528. $^1$H NMR (DMSO-d$_6$): δ=11.90 (s, 1H), 11.80 (s, 1H), 9.24 (s, 1H), 7.91 (s, 1H), 7.62 (s, 2H), 7.38 (m, 2H), 7.32 (d, J=8.3 Hz, 1H), 7.19 (t, J=7.6 Hz, 1H), 6.90 (d, J=6.9 Hz, 1H), 1.50 (s, 9H). EI-MS (70 eV) m/z (%): 390 (100) [M$^{+-}$]. Anal. (C$_{23}$H$_{23}$N$_3$O$_3$): Cal.: C, 70.93, H, 5.95, N, 10.79. Found: C, 70.75, H, 6.15, N, 10.52.

tert-Butyl (2-(4-methyl-1H-indole-2-carbonyl)-1H-indol-6-yl)carbamate (30c)

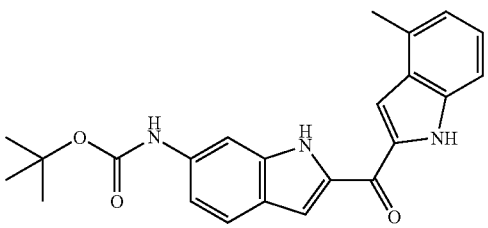 [SMILES: Cc1cccc2[nH]c(C(=O)c3cc4ccc(NC(=O)OC(C)(C)C)cc4[nH]3)cc12]

Preparation from and 4-methyl-1-(phenylsulfonyl)-1H-indole-2-carbonyl chloride (29a) and tert-butyl 1H-indol-6-ylcarbamate (16c) as described above. Yield: 0.44 g, 1.1 mmol (37%). $^1$H NMR (DMSO-d$_6$): δ=11.92 (s, 1H), 11.85 (s, 1H), 9.30 (s, 1H), 7.91 (s, 1H), 7.67 (t, J=9.7 Hz, 1H), 7.58 (d, J=1.5 Hz, 1H), 7.38 (m, 2H), 7.23-7.12 (m, 1H), 7.00 (dd, J=8.7, 1.8 Hz, 1H), 6.90 (d, J=7.0 Hz, 1H), 2.59 (s, 3H), 1.59 (s, 9H). Cc: DCM:EtOAc 6:1.

tert-Butyl (2-(4-methyl-1H-indole-2-carbonyl)-1H-indol-7-yl)carbamate (30d)

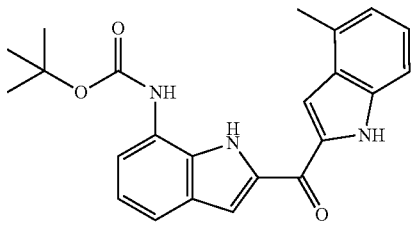 [SMILES: Cc1cccc2[nH]c(C(=O)c3cc4cccc(NC(=O)OC(C)(C)C)c4[nH]3)cc12]

Preparation from and 4-methyl-1-(phenylsulfonyl)-1H-indole-2-carbonyl chloride (29a) and tert-butyl 1H-indol-7-ylcarbamate (16d) as described above. Yield: 0.22 g, 0.56 mmol (6%). Mp: 85.4° C. IR (KBr): ν (cm−1)=3331, 2926, 1693, 1582, 1512. $^1$H NMR (DMSO-d$_6$): δ=11.94 (s, 2H), 9.46 (s, 1H), 7.87 (d, J=7.8 Hz, 1H), 7.72 (d, J=2.0 Hz, 1H), 7.67 (d, J=1.4 Hz, 1H), 7.44 (d, J=8.0 Hz, 1H), 7.33 (d, J=8.1 Hz, 1H), 7.24-7.16 (m, 1H), 7.08 (d, J=7.9 Hz, 1H), 6.90 (d, J=6.9 Hz, 1H), 2.59 (s, 3H), 1.58 (s, 9H). ESI-MS (70 eV) m/z (%): 390.2 (100) [MH$^+$].

tert-Butyl (2-(5-(benzyloxy)-1H-indole-2-carbonyl)-1H-pyrrolo[2,3-b]pyridin-5-yl) Carbamate (32f)

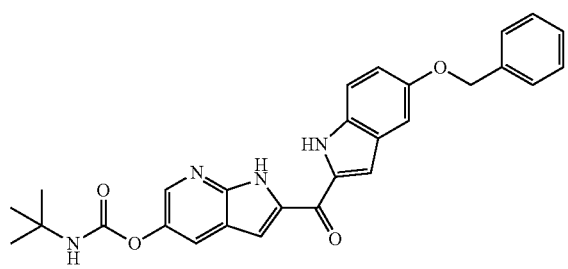 [SMILES: CC(C)(C)NC(=O)Oc1cnc2[nH]c(C(=O)c3cc4cc(OCc5ccccc5)ccc4[nH]3)cc2c1]

Preparation from and 5-(benzyloxy)-1-(phenylsulfonyl)-1H-indole-2-carbonyl chloride (29b) and tert-Butyl (1-(phenylsulfonyl)-1H-pyrrolo[2,3-b]pyridin-5-yl)carbamate (16e) as described above. Yield: 3.4 g, 7.05 mmol (66%). Mp: 205-209° C. IR (KBr): ν (cm$^{-1}$)=3299, 1694, 1525. $^1$H-NMR (DMSO-d$_6$): δ=12.34 (s, 1H), 11.86 (s, 1H), 9.47 (s, 1H), 8.44 (d, J=2.2 Hz, 1H), 8.30 (s, 1H), 7.50 (d, J=1.4 Hz, 1H), 7.48 (d, J=2.1 Hz, 2H), 7.42 (m, 4H), 7.37-7.31 (m, 1H), 7.27 (d, J=2.3 Hz, 1H), 7.07 (dd, J=8.9, 2.4 Hz, 1H), 1.50 (d, J=9.1 Hz, 9H). ESI-MS (70 eV) m/z (%): 483.2 (100) [MH$^+$]. Anal. (C$_{28}$H$_{26}$N$_4$O$_4$×¼EE): Cal.: C, 69.07, H, 5.55, N, 11.11. Found: C, 68.96, H, 5.40, N, 11.43.

tert-Butyl (2-(5-(benzyloxy)-1H-indole-2-carbonyl)-1H-pyrrolo[2,3-c]pyridin-5-yl) carbamate (32g)

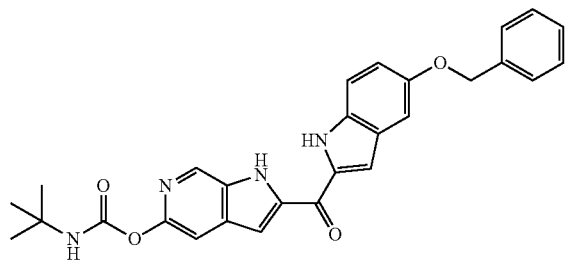 [SMILES: CC(C)(C)NC(=O)Oc1cc2cc(C(=O)c3cc4cc(OCc5ccccc5)ccc4[nH]3)[nH]c2cn1]

Preparation from 5-(benzyloxy)-1-(phenylsulfonyl)-1H-indole-2-carbonyl chloride (29b) and tert-butyl (1-(phenylsulfonyl)-1H-pyrrolo[2,3-c]pyridin-5-yl)carbamate (16f) as described above. Yield: 2.22 g, 4.6 mmol (41%). Mp: 172.1-172.3° C. IR (KBr): ν (cm$^{-1}$)=3455, 3301, 17231, 1524. $^1$H-NMR (DMSO-d$_6$): δ=12.22 (s, 1H), 11.96 (s, 1H), 9.46 (s, 1H), 8.59 (s, 1H), 8.04 (s, 1H), 7.54 (d, J=1.6 Hz, 1H), 7.49 (d, J=7.3 Hz, 3H), 7.45-7.38 (m, 3H), 7.35 (d, J=7.1 Hz, 1H), 7.27 (d, J=2.2 Hz, 1H), 7.09 (dd, J=9.0, 2.4 Hz, 1H), 1.50 (s, 9H). ESI-MS (70 eV) m/z (%): 483.2 (100) [MH$^+$]. Anal. (C$_{28}$H$_{26}$N$_4$O$_4$×H$_2$O): Calc.: C, 67.19, H, 5.64, N, 11.19. Found: C, 67.65, H, 5.35, N, 11.07. Cc: DCM:EtOAc 1:1.

tert-Butyl (2-(5-(benzyloxy)benzofuran-2-carbonyl)-1H-indol-5-yl)carbamate (32h)

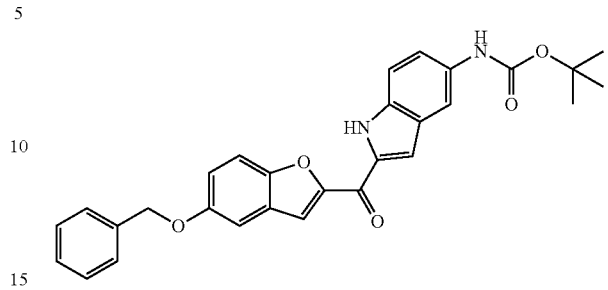

Preparation from 5-(benzyloxy)benzofuran-2-carbonyl chloride (29c) and tert-butyl (1-(phenylsulfonyl)-1H-indol-5-yl)carbamate (16b) as described above. Yield: 2.48 g, 5.14 mmol (26%). Mp: 222.0° C. IR (KBr): ν (cm$^{-1}$)=3419, 3301, 1712, 1606. $^1$H-NMR (DMSO-d$_6$): δ=11.93 (s, 1H), 9.27 (s, 1H), 7.92 (t, J=1.9 Hz, 2H), 7.81-7.70 (m, 2H), 7.56-7.46 (m, 2H), 7.47-7.30 (m, 6H), 7.27 (dd, J=9.1, 2.6 Hz, 1H), 5.19 (s, 2H), 1.49 (s, 9H). ESI-MS (70 eV) m/z (%): 483.2 (80) [MH$^+$]. Anal. (C$_{29}$H$_{26}$N$_2$O$_5$): Cal.: C, 72.18, H, 5.43, N, 5.81. Found: C, 72.17, H, 5.63, N, 5.65. SC: DCM:EtOAc 20:1.

tert-Butyl (2-(5-(benzyloxy)benzofuran-2-carbonyl)-1H-pyrrolo[2,3-c]pyridin-5-yl) carbamate (32i)

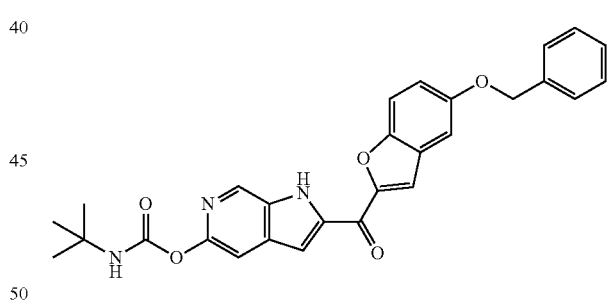

Preparation from 5-(benzyloxy)benzofuran-2-carbonyl chloride (29c) and tert-butyl (1-(phenylsulfonyl)-1H-pyrrolo[2,3-c]pyridin-5-yl)carbamate (16f) as described above. Yield: 1.2 g, 2.5 mmol (21%). $^1$H NMR (Acetone-d$_6$): δ=8.71 (s, 1H), 8.38 (s, 1H), 8.26 (s, 1H), 7.92 (d, J=0.8 Hz, 1H), 7.85 (s, 1H), 7.73 (d, J=9.1 Hz, 1H), 7.54 (d, J=7.3 Hz, 2H), 7.48-7.39 (m, 3H), 7.38-7.30 (m, 2H), 5.23 (s, 2H), 1.54 (s, 9H). EI-MS (70 eV) m/z (%): 484 (100) [MH$^+$].

Deprotection of the Tert-Butyl Carbamate Group—Synthesis of 31a-d and 33e-g, 39a-39b The tert-butyl carbamate derivative was dissolved in TFA and stirred at rt. After 15 min. the reaction mixture was added to ice water and alkalized with conz. NH$_3$ (pH=9). The precipitating product was aspirated.

(4-Amino-1H-indol-2-yl)(4-methyl-1H-indol-2-yl)methanone (31a)

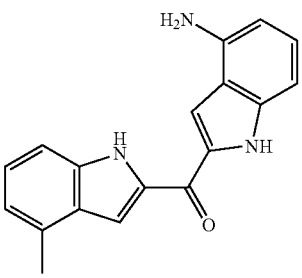 [SMILES: Cc1cccc2[nH]c(C(=O)c3cc4c(N)cccc4[nH]3)cc12]

Preparation from (30a) as described above. Yield: 0.15 g, 0.52 mmol (33%). $^1$H NMR (DMSO-$d_6$): δ=11.86 (s, 1H), 11.56 (s, 1H), 7.89 (s, 1H), 7.57 (s, 1H), 7.32 (d, J=8.5 Hz, 1H), 7.23-7.13 (m, 1H), 7.01-6.87 (m, 2H), 6.61 (dd, J=13.9, 8.0 Hz, 1H), 6.16 (d, J=7.5 Hz, 1H), 5.74 (s, 2H), 2.61 (s, 3H). EI-MS (70 eV) m/z (%): 290 (100) [M$^{+\cdot}$]. Anal. ($C_{18}H_{15}N_3O \times \frac{1}{4}H_2O$): Cal.: C, 73.58, H, 5.32, N, 14.30. Found: C, 73.82, H, 5.26, N, 14.14. Cc: DCM:EtOAc 10:1.

(5-Amino-1H-indol-2-yl)(4-methyl-1H-indol-2-yl)methanone (31b)

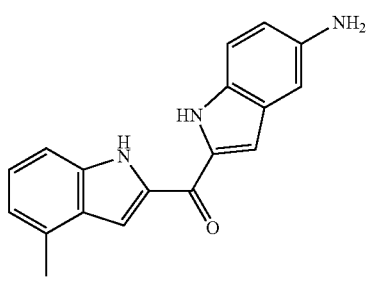 [SMILES: Cc1cccc2[nH]c(C(=O)c3cc4cc(N)ccc4[nH]3)cc12]

Preparation from (30b) as described above. Yield: 0.4 g, 1.4 mmol (92%). Mp: 226.9-227.7° C. IR (KBr): ν (cm−1)=3428, 3266, 1594, 1579, 1530. $^1$H NMR (DMSO-$d_6$): δ=11.85 (s, 1H), 11.50 (s, 1H), 7.37 (s, 1H), 7.55 (s, 1H), 7.31 (d, J=8.3 Hz, 1H), 7.23 (d, J=8.7 Hz, 1H), 7.18 (m, 1H), 6.89 (d, J=6.9 Hz, 1H), 6.81 (s, 1H), 6.75 (dd, J=1.4 Hz, J=8.8 Hz, 1H), 2.58 (s, 3H). EI-MS (70 eV) m/z (%): 290 (100) [M+.]. Anal. ($C_{18}H_{15}N_3O \times \frac{1}{3}H_2O$): Cal.: C, 73.20, H, 5.35, N, 14.23. Found: C, 73.16, H, 5.22, N, 14.29.

(6-Amino-1H-indol-2-yl)(4-methyl-1H-indol-2-yl)methanone (31c)

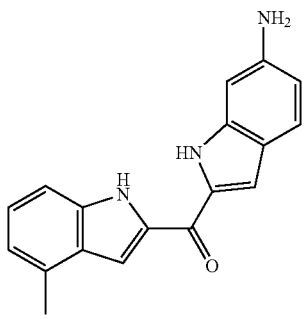 [SMILES: Cc1cccc2[nH]c(C(=O)c3cc4ccc(N)cc4[nH]3)cc12]

Preparation from (30c) as described above. Yield: 0.6 g, 2.1 mmol (90%). The crude product was directly converted in the next step without purification

(7-Amino-1H-indol-2-yl)(4-methyl-1H-indol-2-yl)methanone (31d)

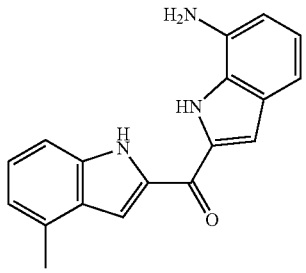 [SMILES: Cc1cccc2[nH]c(C(=O)c3cc4cccc(N)c4[nH]3)cc12]

Preparation from (30d) as described above. Yield: 0.5 g, 1.7 mmol (87%). The crude product was directly converted in the next step without purification.

(5-Amino-1H-indol-2-yl)(5-(benzyloxy)-1H-indol-2-yl)methanone (31e)

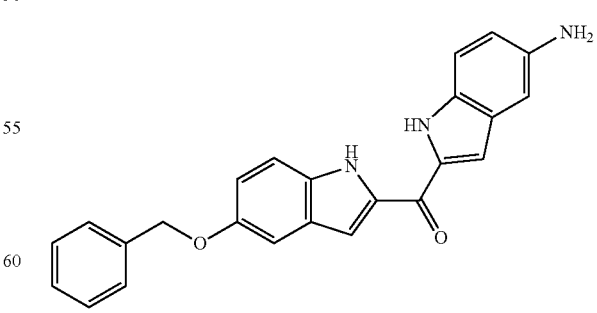

Preparation from (32e) as described above. Yield: 1.3 g, 3.43 mol (62%). Mp: 187.2-191.2° C. IR (KBr): ν (cm$^{-1}$)=3375, 3025, 1526. $^1$H-NMR (DMSO-$d_6$): δ=11.78 (s, 1H), 11.51 (s, 1H), 7.47 (t, J=9.7 Hz, 2H), 7.44-7.29 (m, 5H), 7.24 (dt, J=16.0, 4.8 Hz, 3H), 7.09-6.97 (m, 1H), 6.88-6.65 (m, 2H), 5.13 (s, 2H), 4.80 (s, 1H). ESI-MS (70 eV) m/z (%): 382.0 (100) [MH$^+$]. Anal. (C$_{24}$H$_{19}$N$_3$O$_2$×¼H$_2$O): Cal.: C, 74.69, H, 5.09, N, 10.89. Found: C, 74.66, H, 5.37, N, 10.79.

(5-Amino-1H-pyrrolo[2,3-b]pyridin-2-yl)(5-(benzyloxy)-1H-indol-2-yl)methanone (33f)

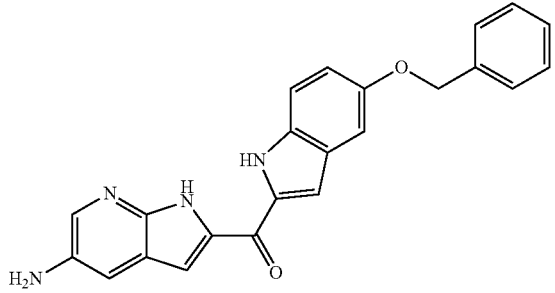 [SMILES: Nc1cnc2[nH]c(C(=O)c3cc4cc(OCc5ccccc5)ccc4[nH]3)cc2c1]

Preparation from (32f) as described above. Yield: 0.7 g, 0.018 mmol (35%). Mp: 290.0° C. IR (KBr): ν (cm$^{-1}$)=3410, 2360, 1595. $^1$H-NMR (DMSO-d$_6$): δ=11.91 (s, 1H), 9.54 (s, 1H), 9.27 (bs, 1H), 7.90 (bs, 1H), 7.87 (d, J=0.7 Hz, 1H), 7.72 (d, J=2.0 Hz, 1H), 7.63 (d, J=9.0 Hz, 1H), 7.38 (s, 2H), 7.12 (d, J=2.4 Hz, 1H), 7.03 (dd, J=8.9, 2.5 Hz, 1H), 1.50 (s, 9H). ESI-MS (70 eV) m/z (%): 383.2 (100) [MH$^+$]. Anal. (C$_{23}$H$_{18}$N$_4$O$_2$×⅔H$_2$O): Cal.: C, 70.04, H, 4.94, N, 14.20. Found: C, 70.04, H, 4.72, N, 14.23.

(5-Amino-1H-pyrrolo[2,3-c]pyridin-2-yl)(5-(benzyloxy)-1H-indol-2-yl)methanone (33g)

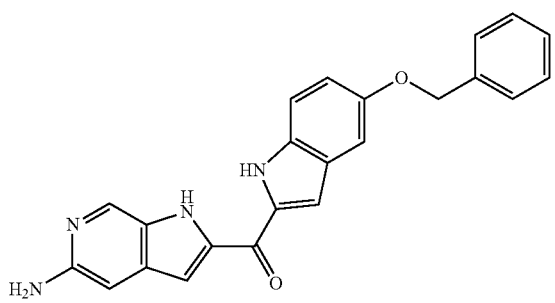 [SMILES: Nc1cc2cc(C(=O)c3cc4cc(OCc5ccccc5)ccc4[nH]3)[nH]c2cn1]

Preparation from (32g) as described above. Yield: 0.80 g, 2.07 mmol (59%). Mp: 288.4° C. (decomposition). IR (KBr): ν (cm$^{-1}$)=3439, 3334, 2978, 1522. $^1$H-NMR (DMSO-d$_6$): δ=12.18 (s, 1H), 11.79 (s, 1H), 9.45 (s, 1H), 9.05 (s, 1H), 8.59 (s, 1H), 8.04 (s, 1H), 7.50 (d, J=1.3 Hz, 1H), 7.47 (d, J=1.6 Hz, 1H), 7.33 (d, J=8.9 Hz, 1H), 7.02 (d, J=2.1 Hz, 1H), 6.89 (dd, J=8.8, 2.3 Hz, 1H), 1.50 (s, 9H). ESI-MS (70 eV) m/z (%): 393.2 (100) [MH$^+$]. Anal. (C$_{21}$H$_{20}$N$_4$O$_4$×⅙EtOAc): Cal.: C, 63.92, H, 5.28, N, 13.76. Found: C, 63.50, H, 5.18, N, 13.94.

(5-Amino-1H-indol-2-yl)(5-hydroxybenzofuran-2-yl)methanone (35h)

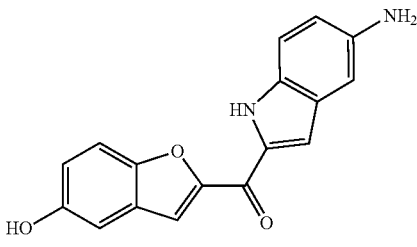 [SMILES: Nc1ccc2[nH]c(C(=O)c3cc4cc(O)ccc4o3)cc2c1]

Preparation from (34h) as described above. Yield: 0.3 g, 1.03 mmol (88%). $^1$H-NMR (DMSO-d$_6$): δ=11.74 (s, 1H), 9.04 (s, 1H), 7.75 (d, J=0.7 Hz, 1H), 7.58 (d, J=1.5 Hz, 1H), 7.47 (d, J=9.5 Hz, 1H), 7.31 (d, J=8.9 Hz, 1H), 7.01 (d, J=2.2 Hz, 1H), 6.91-6.84 (m, 2H), 5.12 (s, 2H). ESI-MS (70 eV) m/z (%): 293.1 (100) [MH$^+$].

(5-Amino-1H-pyrrolo[2,3-c]pyridin-2-yl)(5-hydroxybenzofuran-2-yl)methanone (35i)

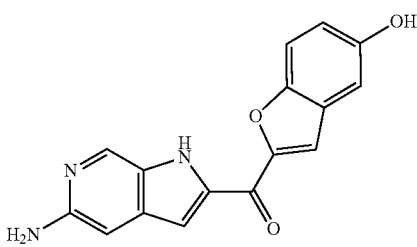 [SMILES: Nc1cc2cc(C(=O)c3cc4cc(O)ccc4o3)[nH]c2cn1]

Preparation from (34i) as described above. Yield: 0.15 g, 0.5 mmol (50%). $^1$H-NMR (DMSO-d$_6$): δ=12.56 (s, 1H), 9.67 (s, 1H), 8.48 (s, 1H), 8.06 (s, 1H), 7.68-7.60 (m, 2H), 7.21-7.13 (m, 2H), 7.10 (dd, J=8.9, 2.5 Hz, 1H). ESI-MS (70 eV) m/z (%): 294.1 (100) [MH$^+$]. Recrystallization was performed from THF.

(5-amino-1H-indol-2-yl)(5-(2-morpholinoethoxy)-1H-indol-2-yl)methanone (39a)

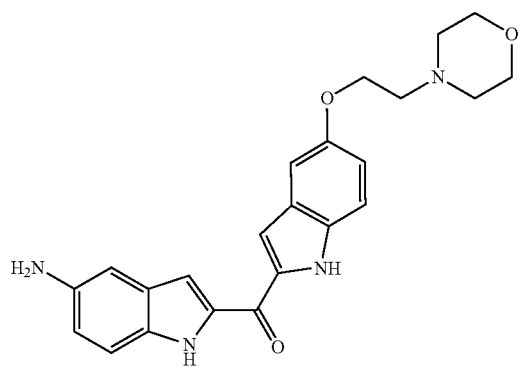 [SMILES: Nc1ccc2[nH]c(C(=O)c3cc4cc(OCCN5CCOCC5)ccc4[nH]3)cc2c1]

Preparation from (38a) as described above. Yield 0.15 g (0.37 mmol, 93%) light yellow solid after cc (SiO$_2$, CH$_2$Cl$_2$, ethyl acetate 1:1). $^1$H NMR (300 MHz, DMSO) δ 11.75 (d, J=1.5 Hz, 1H), 11.49 (s, 1H), 7.45-7.34 (m, 2H), 7.22 (dd, J=14.9, 5.2 Hz, 3H), 6.96 (dd, J=8.9, 2.4 Hz, 1H), 6.83-6.70 (m, 2H), 4.77 (s, 2H), 4.11 (t, J=5.7 Hz, 2H), 3.73-3.49 (m, 4H), 3.32 (s, J=7.0 Hz, 2H), 2.73 (t, J=5.7 Hz, 2H), 2.52 (d, J=2.8 Hz, 2H).

Methyl-6-((2-(5-amino-1H-indole-2-carbonyl)-1H-indol-5-yl)oxy)hexanoate (39b)

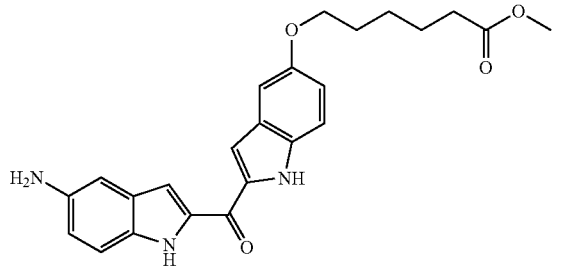 [SMILES: COC(=O)CCCCCOc1ccc2[nH]c(C(=O)c3cc4cc(N)ccc4[nH]3)cc2c1]

Preparation from (38b) as described above. Yield 2.01 g (4.8 mmol, 91%) beige solid. Mp. 67.4-68.2° C. IR (KBr): ν (cm$^{-1}$)=3331, 2945, 1588, 1528. $^1$H-NMR (300 MHz, DMSO-d$_6$): δ=12.18 (s, 1H, Indole-NH), 11.88 (s, 1H, Indole-NH), 9.83 (bs, 2H, NH$_2$), 7.71 (s, 1H, ArH), 7.64 (d, J=9.3 Hz, 1H, ArH), 7.59 (d, J=8.8 Hz, 1H, ArH), 7.52 (s, 1H, ArH), 7.41 (d, J=9.0 Hz, 1H, ArH), 7.25 (d, J=9.9 Hz, 1H, ArH), 7.16 (s, 1H, ArH), 6.98 (dd, J=8.9, 2.2 Hz, 1H, ArH), 3.98 (t, J=6.3 Hz, 2H, CH$_2$), 3.65-3.53 (m, 3H, O—CH$_3$), 2.41-2.26 (m, 2H, CH$_2$), 1.81-1.39 (m, 6H, CH$_2$). ESI-MS (120 eV) m/z (%): 420.0 (90) [MH$^+$]. Anal. (C$_{24}$H$_{25}$N$_3$O$_4$*0.5H$_2$O): Calcd. C, 67.99, H, 6.06, N, 9.91. Found. C, 67.96, H, 6.16, N, 9.73.

Removal of the Benzyloxy Protection Group—Synthesis of 34e, 34h, 34i, 35e-g

The appropriate benzyloxy-derivative was dissolved in THF:MeOH (1:1), NH$_4$HCCO (4 eq) was added and the mixture was heated till reflux. When the temperature was reached, a catalytic amount of Pd on carcoal (10% Pd containing 50% H$_2$O was added and the reaction was monitored by TLC. After completion of the reaction, the mixture was filtered off over a small pad of sodium sulfate to remove the catalyst and an excess of ammonium formate. The pad was washed with a small amount of EtOH twice. To the clear yellow solution obtained water (100 mL) was added and most of the organic solvent removed under reduced pressure till the product precipitates as yellow crystals. The product was removed by filtration, washed with water, dried and crystallized from CH$_2$Cl$_2$ by dissolution in the necessary amount of CH$_2$Cl$_2$ and removing most of the solvent till sufficient crystallization appears.

tert-Butyl-(2-(5-hydroxy-1H-indol-2-carbonyl)-1H-indol-5-yl)carbamate (34e)

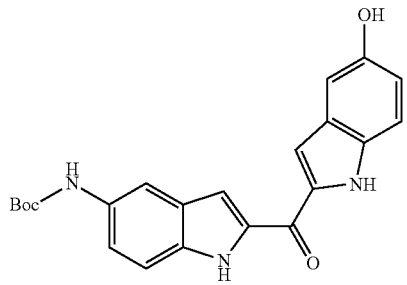 [SMILES: CC(C)(C)OC(=O)Nc1ccc2[nH]c(C(=O)c3cc4cc(O)ccc4[nH]3)cc2c1]

Preparation from (32e) as described above. Yield: 7.43 g, (19.0 mmol, 77%) yellow solid by crystallisation from EtOAc. 225.5-225.7° C. IR (KBr): ν (cm$^{-1}$)=3529, 3345, 2982, 1585, 1534. $^1$H-NMR (300 MHz, DMSO-d$_6$): δ=11.78 (d, J=1.7 Hz, 1H, Indole-NH), 11.66 (d, J=1.7 Hz, 1H, OH), 9.23 (s, 1H, Indole-NH), 8.98 (s, 1H, NH), 7.86 (s, 1H, ArH), 7.48 (d, J=2.1 Hz, 1H, ArH), 7.42-7.27 (m, 4H, ArH), 7.00 (d, J=2.3 Hz, 1H, ArH), 6.85 (dd, J=8.8, 2.3 Hz, 1H, ArH), 1.49 (s, 9H, (CH$_3$)$_3$). ESI-MS (120 eV) m/z (%): 392.0 (80) [MH$^+$]. Anal. (C$_{22}$H$_{21}$N$_3$O$_4$): Calcd. C, 67.51, H, 5.41, N, 10.74. Found. C, 67.19, H, 5.34, N, 10.74.

tert-Butyl (2-(5-hydroxybenzofuran-2-carbonyl)-1H-indol-5-yl)carbamate (34h)

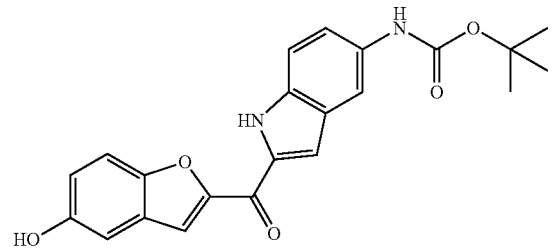 [SMILES: CC(C)(C)OC(=O)Nc1ccc2[nH]c(C(=O)c3cc4cc(O)ccc4o3)cc2c1]

Preparation from (32h) as described above. Yield: 0.7 g, 0.018 mmol (35%). Mp: 217.3-220.2° C. IR (KBr): ν (cm$^{-1}$)=3311, 2978, 1552. $^1$H-NMR (DMSO-d$_6$): δ=11.91 (s, 1H), 9.54 (s, 1H), 9.27 (bs, 1H), 7.90 (bs, 1H), 7.87 (d, J=0.7 Hz, 1H), 7.72 (d, J=2.0 Hz, 1H), 7.63 (d, J=9.0 Hz, 1H), 7.38 (s, 2H), 7.12 (d, J=2.4 Hz, 1H), 7.03 (dd, J=8.9, 2.5 Hz, 1H), 1.50 (s, 9H). ESI-MS (70 eV) m/z (%): 393.2 (100) [MH$^+$]. Anal. (C$_{22}$H$_{20}$N$_2$O$_5$×⅓H$_2$O): Cal.: C, 66.32, H, 5.23, N, 7.03. Found: C, 66.45, H, 5.24, N, 7.03.

tert-Butyl (2-(5-hydroxybenzofuran-2-carbonyl)-1H-pyrrolo[2,3-c]pyridin-5-yl)carbamate (34i)

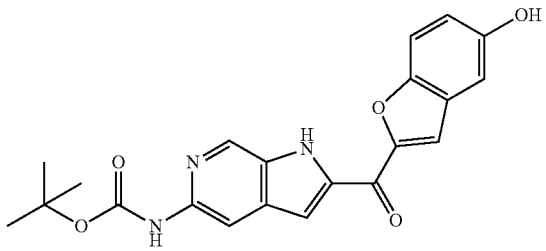 [SMILES: CC(C)(C)OC(=O)Nc1cc2cc(C(=O)c3cc4cc(O)ccc4o3)[nH]c2cn1]

Preparation from (32i) as described above. Yield: 0.40 g, 1.02 mmol (45%). $^1$H-NMR (DMSO-d$_6$): δ=12.29 (s, 1H), 9.59 (s, 1H), 9.50 (s, 1H), 8.61 (s, 1H), 8.06 (s, 1H), 7.98 (d, J=7.6 Hz, 1H), 7.73 (d, J=7.9 Hz, 1H), 7.63 (d, J=8.9 Hz, 1H), 7.14 (d, J=2.4 Hz, 1H), 7.06 (dd, J=8.9, 2.5 Hz, 1H), 1.49 (s, 9H). ESI-MS (70 eV) m/z (%): 394 (100) [MH$^+$]. Anal. (C$_{21}$H$_{19}$N$_3$O$_5$×½Heptan): Cal.: C, 66.35, H, 6.14, N, 9.47. Found: C, 66.23, H, 6.04, N, 9.11. Recrystallization from heptane.

(5-Amino-1H-indol-2-yl)(5-hydroxy-1H-indol-2-yl)methanone (35e)

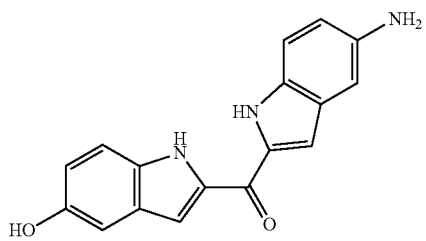 [SMILES: Nc1ccc2[nH]c(C(=O)c3cc4cc(O)ccc4[nH]3)cc2c1]

Preparation from (33e) as described above. Yield: 0.82 g, 2.8 mmol (74%). Mp: 289.1–290.4° C. IR (KBr): ν (cm$^{-1}$) =3416, 1603, 1534. $^1$H-NMR (DMSO-d$_6$): δ=11.61 (s, 1H), 11.47 (s, 1H), 8.97 (s, 1H), 7.35 (t, J=4.0 Hz, 1H), 7.29 (dd, J=11.9, 4.9 Hz, 2H), 7.21 (d, J=8.7 Hz, 1H), 7.02 (t, J=7.7 Hz, 1H), 6.83 (dt, J=7.8, 3.9 Hz, 1H), 6.80–6.69 (m, 2H), 4.72 (bs, 2H). Cl-MS (70 eV) m/z (%): 292.0 (100) [MH$^+$]. Anal. (C$_{17}$H$_{13}$N$_3$O$_2$×⅙H$_2$O): Cal.: C, 69.38, H, 4.50, N, 14.42. Found: C, 69.32, H, 4.61, N, 14.26.

(5-Amino-1H-pyrrolo[2,3-c]pyridin-2-yl)(5-hydroxy-1H-indol-2-yl)methanone (35g)

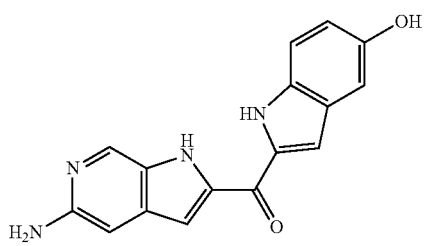 [SMILES: Nc1cc2cc(C(=O)c3cc4cc(O)ccc4[nH]3)[nH]c2cn1]

Preparation from (33g) as described above. Yield: 0.60 g, 2.07 mmol (19%). Mp: 360.0° C. (decomposition). IR (KBr): ν (cm$^1$)=3432, 3323, 1627, 1522. $^1$H-NMR (DMSO-d$_6$): δ=11.73 (s, 2H), 9.02 (s, 1H), 8.37 (s, 1H), 7.43 (d, J=1.7 Hz, 1H), 7.32 (d, J=8.9 Hz, 1H), 7.23 (s, 1H), 7.01 (d, J=2.3 Hz, 1H), 6.87 (dd, J=8.9, 2.3 Hz, 1H), 6.65 (s, 1H), 5.23 (s, 2H). ESI-MS (70 eV) m/z (%): 293.1 (100) [MH$^+$]. Anal. (C$_{16}$H$_{21}$N$_4$O$_2$×H$_2$O): Cal.: C, 61.93, H, 4.55, N, 18.06. Found: C, 62.13, H, 4.46, N, 17.20. Cc: EtOAc: 2.5% MeOH

Preparation of the Corresponding 5-(Tert-Butyl)-3-Isocyanatoisoxazole Derivatives 36a-i Step A. 5-tert-Butyl-3-isoxazolyl Isocyanate was prepared according to Lit. (Dumas, Khire et al. 2012) as follows: To a solution of phosgene (1.5 mL, 2.0 M in toluene, 3.0 mmol) in anhydrous CH$_2$Cl$_2$ (10 mL) was added 3-amino-5-tert-butylisoxazole (0.10 g, 0.71 mmol) followed by pyridine (0.5 mL). The mixture was allowed to warm to room temp and stirred overnight (ca. 16 h), then the mixture was concentrated in vacuo. The residue was dissolved in anh. THF (7 mL) and stirred for 10 min. The orange precipitate (pyridinium hydrochloride) was removed and the isocyanate-containing filtrate (approximately 0.1 M in THF) was used as a stock solution.

Step B. The respective arylamine (0.5 mmol) was dissolved in a sealed tube under nitrogen atmosphere in the isocyanate-containing stock solution (10.0 mL, 1.00 mmol) and pyridine (1.0 mL) was added. The mixture was stirred at room temperature overnight, poured into water (20.0 mL) and the yellow precipitate removed by filtration. Column chromatography (SiO$_2$, CH$_2$Cl$_2$/ethyl acetate; 2:1), respectively in the given solvent, and crystallization by removal of most of the solvent under reduced pressure afforded the desired product as yellow crystals.

1-(5-(tert-Butyl)isoxazol-3-yl)-3-(2-(4-methyl-1H-indole-2-carbonyl)-1H-indol-4-yl)urea (36a)

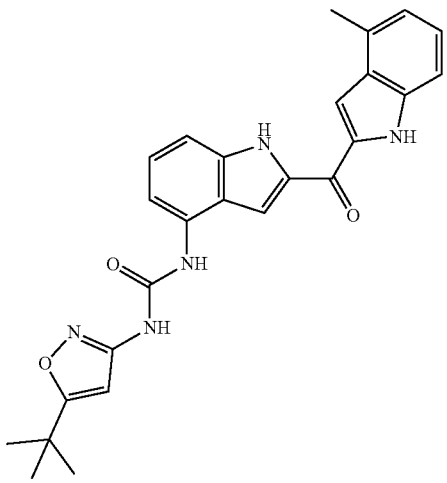 [SMILES: Cc1cccc2[nH]c(C(=O)c3cc4c(NC(=O)Nc5cc(C(C)(C)C)on5)cccc4[nH]3)cc12]

Preparation from (31a) as described above. Yield: 0.07 g, 0.15 mmol (33%). Mp: 265.9° C. IR (KBr): ν (cm$^{-1}$)=3471, 3230, 2966, 1739. $^1$H NMR (DMSO-d$_6$): δ=12.24 (s, 1H), 11.84 (s, 1H), 9.77 (s, 1H), 9.07 (s, 1H), 7.77 (d, J=7.4 Hz, 1H), 7.67 (d, J=1.4 Hz, 1H), 7.56 (d, J=1.4 Hz, 1H), 7.35 (d, J=8.3 Hz, 1H), 7.20 (dd, J=14.3, 6.2 Hz, 2H), 6.93 (d, J=7.0 Hz, 1H), 6.56 (s, 1H), 3.34 (s, 2H), 2.62 (s, 3H), 1.30 (d, J=8.1 Hz, 9H). ESI-MS (70 eV) m/z (%): 465.2 (100) [MH+]. Anal. (C$_{26}$H$_{25}$N$_5$O$_3$): Cal.: C, 68.56, H, 5.53, N, 15.37. Found: C, 68.13, H, 5.61, N, 15.56. Cc: DCM:EtOAc 10:1.

1-(5-(tert-Butyl)isoxazol-3-yl)-3-(2-(4-methyl-1H-indole-2-carbonyl)-1H-indol-5-yl)urea (36b)

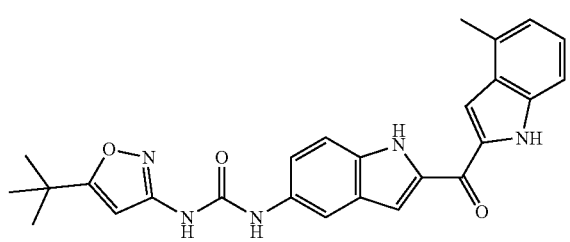 [SMILES: Cc1cccc2[nH]c(C(=O)c3cc4cc(NC(=O)Nc5cc(C(C)(C)C)on5)ccc4[nH]3)cc12]

Preparation from (31b) as described above. Yield: 0.05 g, 0.12 mmol (58%). $^1$H NMR (DMSO-d$_6$): δ=12.09 (s, 1H), 11.72 (s, 2H), 9.47 (s, 1H), 8.76 (s, 1H), 7.95 (d, J=1.7 Hz, 1H), 7.64 (dd, J=9.3, 6.9 Hz, 2H), 7.45 (d, J=8.8 Hz, 1H), 7.26 (ddd, J=31.1, 12.5, 8.2 Hz, 3H), 6.90 (d, J=7.0 Hz, 1H), 6.51 (s, 1H), 2.56 (d, J=20.1 Hz, 3H), 1.24 (m, 9H). EI-MS (70 eV) m/z (%): 456 (100) [M+.]. Anal. (C$_{26}$H$_{27}$N$_5$O$_4$×1H$_2$O): Cal.: C, 65.95, H, 5.75, N, 14.79. Found: C, 65.99, H, 5.72, N, 14.96.

1-(5-(tert-Butyl)isoxazol-3-yl)-3-(2-(4-methyl-1H-indole-2-carbonyl)-1H-indol-6-l)urea (36c)

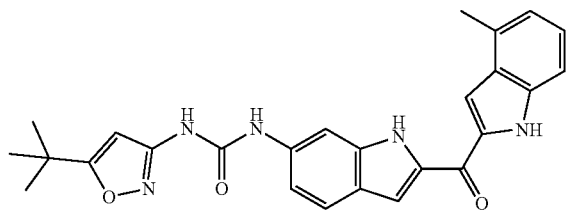 [SMILES: Cc1cccc2[nH]c(C(=O)c3cc4ccc(NC(=O)Nc5cc(C(C)(C)C)on5)cc4[nH]3)cc12]

Preparation from (31c) as described above. Yield: 0.07 g, 0.15 mmol (20%). Mp: 281.4° C. IR (KBr): ν (cm−1)=3283, 2969, 1728, 1595, 1564, 1552. $^1$H NMR (DMSO-d$_6$): δ=12.01 (s, 1H), 11.69 (s, 2H), 9.50 (s, 1H), 8.98 (s, 1H), 7.91 (s, 1H), 7.67 (t, J=9.7 Hz, 1H), 7.58 (d, J=1.5 Hz, 1H), 7.32 (d, J=8.3 Hz, 1H), 7.23-7.12 (m, 1H), 7.00 (dd, J=8.7, 1.8 Hz, 1H), 6.90 (d, J=7.0 Hz, 1H), 6.55 (s, 1H), 2.59 (s, 3H), 1.31 (s, 9H). Cc: DCM:EtOAc 6:1.

1-(5-(tert-Butyl)isoxazol-3-yl)-3-(2-(4-methyl-1H-indole-2-carbon)-1H-indol-7-yl)urea (36d)

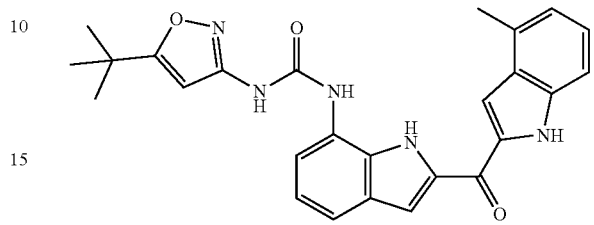

Preparation from (31d) as described above. Yield: 0.06 g, 0.14 mmol (43%). Mp: 235.9° C. IR (KBr): ν (cm−1)=3321, 2968, 1690, 1601, 1582, 1534. $^1$H NMR (DMSO-d$_6$): δ=11.94 (s, 1H), 11.61 (s, 1H), 9.58 (d, J=11.0 Hz, 1H), 9.02 (s, 1H), 7.73 (t, J=8.0 Hz, 1H), 7.68 (d, J=1.4 Hz, 1H), 7.55 (dt, J=10.5, 6.3 Hz, 2H), 7.33 (d, J=8.3 Hz, 1H), 7.25-7.16 (m, 1H), 7.09 (dd, J=13.1, 5.3 Hz, 1H), 6.91 (d, J=6.9 Hz, 1H), 6.55 (s, 1H), 2.65-2.54 (m, 3H), 1.31 (d, J=3.2 Hz, 9H). ESI-MS (70 eV) m/z (%): 465.1 (100) [MH+]. Anal. (C$_{26}$H$_{25}$N$_5$O$_3$×⅔H$_2$O): Cal.: C, 66.80, H, 5.68, N, 14.98. Found: C, 66.46, H, 5.67, N, 15.02. Cc: DCM:EtOAc 10:1.

1-(5-(tert-Butyl)isoxazol-3-yl)-3-(2-(5-hydroxy-1H-indole-2-carbonyl)-1H-indol-5-yl)urea (36e)

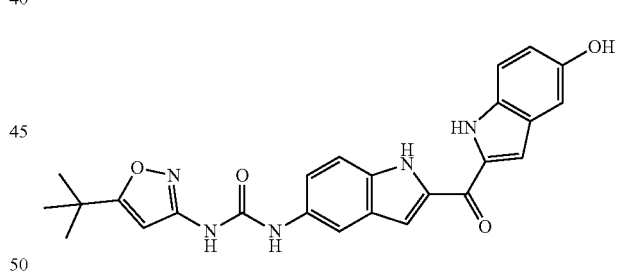

Preparation from (35d) as described above. Yield: 0.80 g, 1.72 mmol (24%). Mp: 268.7° C. IR (KBr): ν (cm$^{−1}$)=3367, 2968, 1627. $^1$H-NMR (DMSO-d$_6$): δ=11.86 (d, J=1.2 Hz, 1H), 11.69 (d, J=1.3 Hz, 1H), 9.46 (s, 1H), 9.00 (s, 1H), 8.75 (s, 1H), 7.91 (d, J=1.5 Hz, 1H), 7.52-7.38 (m, 3H), 7.40-7.23 (m, 2H), 7.02 (d, J=2.1 Hz, 1H), 6.86 (dd, J=8.8, 2.3 Hz, 1H), 6.52 (s, 1H), 1.30 (s, 9H). ESI-MS (70 eV) m/z (%): 458.0 (100) [MH+]. Anal. (C$_{25}$H$_{23}$N$_5$O$_4$): Cal.: C, 65.63, H, 5.07, N, 15.31. Found: C, 65.13, H, 4.95, N, 15.24. Cc: EtOAc:DCM 10:1.

1-(2-(5-(benzyloxy)-1H-indole-2-carbonyl)-1H-pyrrolo[2,3-b]pyridin-5-yl)-3-(5-(tert-butyl)isoxazol-3-yl)urea (35f)

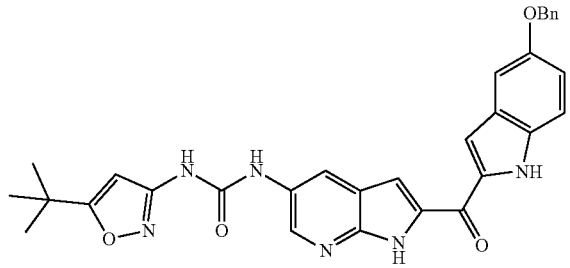 [SMILES: CC(C)(C)c1cc(NC(=O)Nc2cnc3[nH]c(C(=O)c4cc5cc(OCc6ccccc6)ccc5[nH]4)cc3c2)no1]

Preparation from (33f) as described above. Yield 0.35 g (0.64 mmol, 24% brown solid) after cc (SiO$_2$, EtOAc:MeOH 20:1). Mp. 249.7-252.1° C. (Decomposition). IR (KBr): ν (cm$^{-1}$)=3260, 2967, 1653. $^1$H-NMR (300 MHz, DMSO-d$_6$): δ=12.45 (s, 1H, NH), 11.90 (s 1H, NH), 9.65 (s, 1H, NH), 8.92 (s, 1H, ArH), 8.43 (t, J=2.8 Hz, 1H, ArH), 8.38-8.31 (m, 1H, ArH), 7.52-7.45 (m, 4H, ArH), 7.43 (s, 1H, ArH), 7.40 (d, J=1.5 Hz, 1H, ArH), 7.36-7.32 (m, 1H, ArH), 7.28 (d, J=2.3 Hz, 1H, ArH), 7.13-7.03 (m, 1H, ArH), 6.53 (s, 1H, Isoxazol-CH), 5.14 (s, 2H, O—CH$_2$-Ph), 1.30 (s, 9H, (CH$_3$)$_3$). ESI-MS (120 eV) m/z (%): 549.2 (100) [MH$^+$] (MW=548.22 g/mol). Anal. (C$_{31}$H$_{28}$N$_6$O$_4$×0.20 DCM): Cacd. C, 66.26, H, 5.06, N, 14.86. Found. C, 66.42, H, 5.08, N, 14.88.

1-(5-(tert-Butyl)isoxazol-3-yl)-3-(2-(5-hydroxy-1H-indole-2-carbonyl)-1H-pyrrolyl)-1H-pyrrolo[2,3-b]pyridin-5-yl)urea (36f)

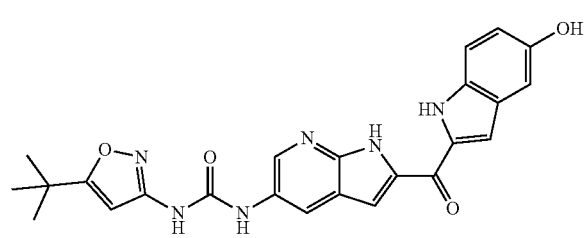 [SMILES: CC(C)(C)c1cc(NC(=O)Nc2cnc3[nH]c(C(=O)c4cc5cc(O)ccc5[nH]4)cc3c2)no1]

Preparation from (35f) as described above for 34h by removal of the benzyloxy protection group. Yield: 0.29 g, 0.64 mmol (97%). Mp: 245.0° C. IR (KBr): ν (cm$^{-1}$)=3419, 3301, 1634, 1652, 1606. $^1$H-NMR (DMSO-d$_6$): δ=13.98 (s, 1H), 12.40 (s, 1H), 11.71 (s, 1H), 10.23 (s, 1H), 9.01 (s, 1H), 8.49 (s, 1H), 8.31 (d, J=2.1 Hz, 1H), 7.51 (d, J=2.0 Hz, 1H), 7.40 (d, J=1.8 Hz, 1H), 7.32 (d, J=5.4 Hz, 1H), 7.00 (t, J=2.6 Hz, 1H), 6.87 (dd, J=8.8, 2.3 Hz, 1H), 1.08 (s, 9H). ESI-MS (70 eV) m/z (%): 461(100) [MH+]. Anal. (C$_{24}$H$_{22}$N$_6$O$_4$× H$_2$O+MeOH): Cal.: C, 59.05, H, 5.55, N, 16.53. Found: C, 59.46, H, 5.42, N, 16.35. Cc: EtOAc:MeOH 20:1.

1-(5-(tert-Butyl)isoxazol-3-yl)-3-(2-(5-hydroxy-1H-indole-2-carbonyl)-1H-pyrrolo[2,3-c]pyridin-5-yl)urea (36g)

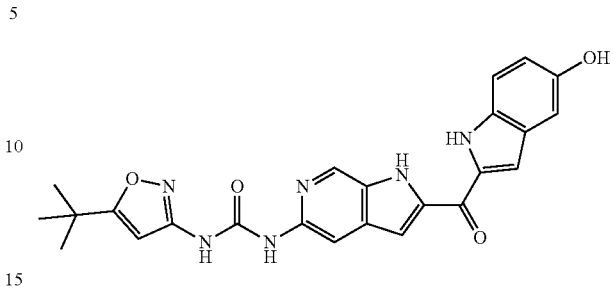

Preparation from (35g) as described above. Yield: 0.74 g, 1.62 mmol (24%). $^1$H-NMR (300 MHz, DMSO-d$_6$) δ=12.29 (s, 1H, Indol-NH), 11.79 (s, 1H, NH), 8.66 (s, 1H, ArH), 8.63 (s, 1H, ArH), 7.35 (s, 1H, ArH), 7.32 (s, 1H, ArH), 7.03 (s, 1H, ArH), 6.91 (d, J=2.3 Hz, 1H, ArH), 6.88 (d, J=2.3 Hz, 1H, ArH), 6.56 (s, 1H, Isoxazol-CH), 1.31 (s, 9H, (CH$_3$)$_3$). ESI-MS (120 eV) m/z (%): 459.2 (100) [MH$^+$]. HR-MS (120 eV) m/z: Ber. 459.1775. Gef. 459.178 (C$_{24}$H$_{23}$N$_6$O$_4$) [MH$^+$].

1-(5-(tert-Butyl)isoxazol-3-yl)-3-(2-(5-hydroxybenzofuran-2-carbonyl)-1H-indol-5-yl)urea (36h)

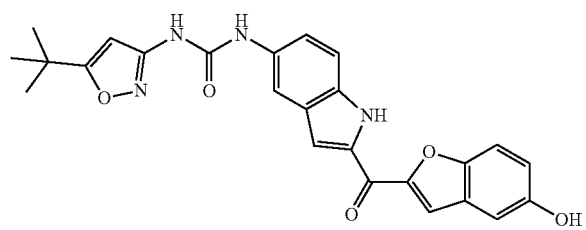 [SMILES: CC(C)(C)c1cc(NC(=O)Nc2ccc3[nH]c(C(=O)c4cc5cc(O)ccc5o4)cc3c2)no1]

Preparation from (35h) as described above. Yield: 0.31 g, 0.68 mmol (32%). Mp: 285.1-285.6° C. IR (KBr): ν (cm$^{-1}$)=3297, 2970, 1630. $^1$H-NMR (DMSO-d$_6$): δ=11.98 (s, 1H), 9.54 (s, 1H), 9.47 (s, 1H), 8.77 (s, 1H), 7.95 (d, J=1.7 Hz, 1H), 7.88 (d, J=0.7 Hz, 1H), 7.74 (d, J=1.4 Hz, 1H), 7.63 (d, J=9.0 Hz, 1H), 7.44 (d, J=8.8 Hz, 1H), 7.32 (dd, J=8.9, 2.0 Hz, 1H), 7.13 (d, J=2.4 Hz, 1H), 7.04 (dd, J=9.0, 2.5 Hz, 1H), 6.52 (s, 1H), 1.30 (d, J=4.5 Hz, 9H). ESI-MS (70 eV) m/z (%): 459.2 (100) [MH+]. Anal. (C$_{25}$H$_{22}$N$_4$O$_5$): Cal.: C, 65.49, H, 4.84, N, 12.22. Found: C, 65.02, H, 4.95, N, 11.81. Cc: EtOAc:DCM 2:1.

1-(5-(tert-Butyl)isoxazol-3-yl)-3-(2-(5-hydroxybenzofuran-2-carbonyl)-1H-pyrrolo[2,3-c]pyridin-5-yl)urea (36i)

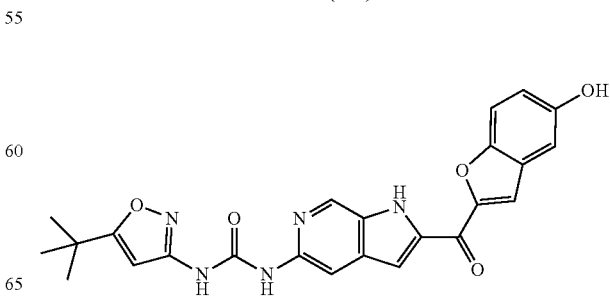

Preparation from (35i) as described above. Yield: 0.31 g, 0.68 mmol (32%). ¹H NMR (400 MHz, DMSO-d₆): δ=12.35 (s, 1H), 9.57 (s, 1H), 9.31 (s, 1H), 8.66 (s, 1H), 8.06 (s, 1H), 7.99 (d, J=0.7 Hz, 1H), 7.74 (d, J=1.3 Hz, 1H), 7.64 (d, J=9.0 Hz, 1H), 7.15 (d, J=2.4 Hz, 1H), 7.07 (dd, J=8.9, 2.5 Hz, 1H), 6.56 (s, 1H), 1.32 (s, 9H). Cc: EtOAc:MeOH 10:1.

1-(5-(tert-Butyl)isoxazol-3-yl)-3-(2-(5-(2-morpholinoethoxy)-1H-indole-2-carbonyl)-1H-indol-5-yl) urea (40a)

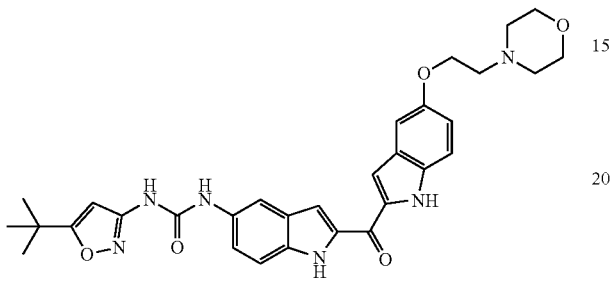

Preparation from (39a) as described above. Yield 0.04 g (0.07 mmol, 21%) yellow solid. 1H NMR (300 MHz, DMSO) δ 11.89 (s, 1H), 11.84 (s, 1H), 9.46 (s, 1H), 8.75 (s, 1H), 7.92 (s, 1H), 7.56-7.36 (m, 4H), 7.29 (dd, J=8.9, 2.0 Hz, 1H), 7.20 (d, J=2.2 Hz, 1H), 6.98 (dd, J=8.9, 2.4 Hz, 1H), 6.52 (s, 1H), 4.11 (t, J=5.7 Hz, 2H), 3.70-3.54 (m, 4H), 3.33 (s, 2H), 2.73 (t, J=5.7 Hz, 2H), 1.30 (s, 9H).

Methyl-6-((2-(5-(3-(5-tert-butyl-isoxazol-3-yl) ureido)-1H-indole-2-carbonyl)-1H-indol-5-yl) oxy) hexanoate (40b)

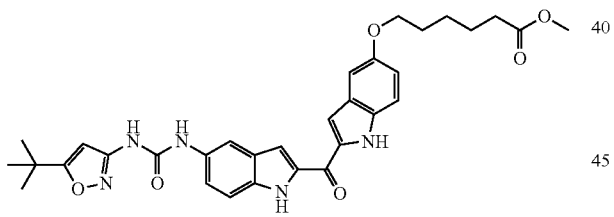

Preparation from (39b) as described above. Yield 0.23 g (0.39 mmol, 51%) light brown solid. Mp. 115.7° C. IR (KBr): ν (cm⁻¹)=3317, 2966, 2947, 1720, 1684. ¹H-NMR (300 MHz, DMSO-d₆): δ=11.88 (s, 1H, Indole-NH), 11.82 (s, 1H, Indole-NH), 9.45 (s, 1H, NH), 8.75 (s, 1H, NH), 7.92 (s, 1H, ArH), 7.51 (d, J=1.1 Hz, 1H, ArH), 7.49-7.36 (m, 3H, ArH), 7.29 (dd, J=8.9, 2.0 Hz, 1H, ArH), 7.17 (d, J=2.2 Hz, 1H, ArH), 6.96 (dd, J=8.9, 2.4 Hz, 1H, ArH), 6.52 (s, 1H, Isoxazole-CH), 3.98 (t, J=6.4 Hz, 2H, CH₂), 3.59 (s, 3H, O—CH₃), 2.40-2.28 (m, 2H, CH₂), 1.82-1.69 (m, 2H, CH₂), 1.68-1.54 (m, 2H, CH₂), 1.54-1.39 (m, 2H, CH₂), 1.30 (s, 9H, (CH₃)₃). ESI-MS (120 eV) m/z (%): 586.1 (100) [MH+]. Anal. (C₃₂H₃₅N₅O₆): Calcd. C, 65.63, H, 6.02, N, 11.96. Found. C, 65.41, H, 6.39, N, 11.81.

Preparation of 46b-d

Compounds 46b-d were prepared by the reaction of isocyanates 27b-27d with (5-amino-1H-indol-2-yl)(5-hydroxy-1H-indol-2-yl)methanone (35e) as described above for 36a-i. The used isocyanates 27b-d were obtained from the respective arylamines by reaction with trichloromethyl chloroformate in THF analogous Lit. (Bhagwat, Chao et al. 2007). Column chromatography (SiO₂, CH₂Cl₂/ethyl acetate; 2:1), respectively in the given solvent, and crystallization by removal of most of the solvent under reduced pressure afforded the desired product as yellow crystals.

1-(5-tert-Butyl-1,3,4-thiadiazol-2-yl)-3-(2-(5-hydroxy-1H-indole-2-carbonyl)-1H-indol-5-yl)urea (46b)

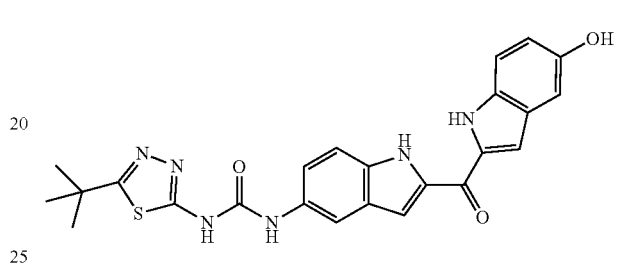

Yield: 0.9 g, 1.9 mmol (8%). Mp: 235.0° C. IR (KBr): ν (cm⁻¹)=3299, 2961, 1699, 1527. ¹H-NMR (DMSO-d₆): δ=11.90 (s, 1H), 11.69 (s, 1H), 10.21 (s, 1H), 9.06 (s, 1H), 8.99 (s, 1H), 7.95 (s, 1H), 7.62-7.27 (m, 5H), 7.01 (d, J=2.1 Hz, 1H), 6.86 (d, 1H), 1.46 (s, 9H). ESI-MS (70 eV) m/z (%): 475.0 (100) [MH+]. Anal. (C₂₄H₂₂N₆O₃S): Cal.: C, 60.75, H, 4.67, N, 17.71, S, 6.76. Found: C, 60.57, H, 4.68, N, 17.53, S, 6.36.

1-(5-tert-Butylisothiazol-3-yl)-3-(2-(5-hydroxy-1H-indol-2-carbonyl)-1H-indol-5-yl) urea (46c)

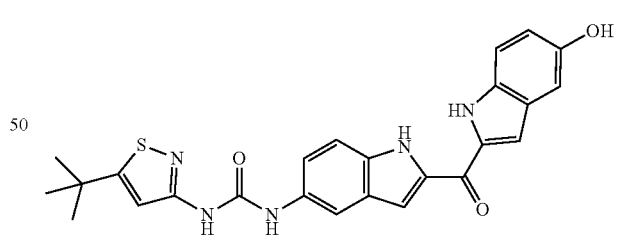

Yield: 0.9 g, 1.92 mmol (13%). Mp: 295.6° C. IR (KBr): ν (cm⁻¹)=3364, 2959, 1678. ¹H-NMR (DMSO-d₆): δ=11.86 (d, J=1.6 Hz, 1H), 11.69 (d, J=1.6 Hz, 1H), 9.72 (s, 1H), 9.37 (s, 1H), 8.99 (s, 1H), 7.95 (d, J=1.7 Hz, 1H), 7.52 (d, J=1.5 Hz, 1H), 7.42 (dd, J=7.9, 5.3 Hz, 2H), 7.34-7.24 (m, 3H), 7.01 (d, J=2.2 Hz, 1H), 6.91-6.81 (m, 1H), 1.29 (s, 9H). ESI-MS (70 eV) m/z (%): 474.0 (100) [MH⁺]. Anal. (C₂₅H₂₃N₅O₃S): Cal.: C, 63.41, H, 4.90, N, 14.79, S, 6.77. Found: C, 62.28, H, 5.09, N, 14.59, S, 6.80.

1-(2-(5-Hydroxy-1H-indol-2-carbonyl)-1H-indol-5-yl)-3-(5-methylisoxazol-3-yl) urea (46d)

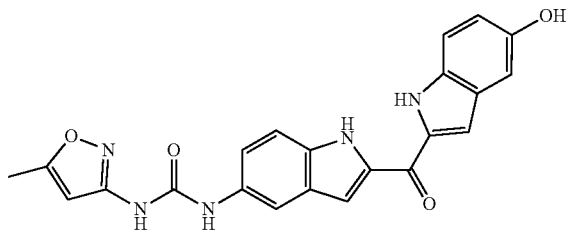 [SMILES: Cc1cc(NC(=O)Nc2ccc3[nH]c(C(=O)c4cc5cc(O)ccc5[nH]4)cc3c2)no1]

Yield: 1.45 g, 3.50 mmol (46%). Mp: 280.6-281.5° C. IR (KBr): ν (cm$^{-1}$)=3343, 1526. $^1$H-NMR (DMSO-d$_6$): δ=11.85 (d, J=1.5 Hz, 1H), 11.69 (t, J=7.2 Hz, 1H), 9.40 (s, 1H), 8.99 (s, 1H), 8.76 (s, 1H), 7.91 (d, J=1.8 Hz, 1H), 7.52 (d, J=1.5 Hz, 1H), 7.44 (d, J=8.8 Hz, 2H), 7.35-7.24 (m, 2H), 7.01 (d, J=2.2 Hz, 1H), 6.93-6.81 (m, 1H), 6.55 (d, J=0.8 Hz, 1H), 2.37 (d, J=0.6 Hz, 3H). ESI-MS (70 eV) m/z (%): 416.0 (100) [MH$^+$]. Anal. (C$_{22}$H$_{17}$N$_5$O$_4$x% EtOAc): Cal.: C, 62.45, H, 4.35, N, 15.50. Found: C, 62.05, H, 4.55, N, 15.95.

Alkylation of 34e—Synthesis of 38a and 38b tert-Butyl 2-(5-hydroxy-1H-indole-2-carbonyl)-1H-indol-5-ylcarbamate (34e) (1.0 g, 2.55 mmol) was dissolved in DMF (10.0 mL) under a nitrogen atmosphere. NaH (1.1 equiv., 60% dispersion in paraffine) was added and the mixture stirred for 15 min at room temperature. The respective alkylans (1.2 equiv., 3.10 mmol) was added. The mixture was stirred at room temperature for 3 d, poured into water, extracted with ethyl acetate (3×100 mL), the combined organic layers dried (Na$_2$SO$_4$), the solvent removed under reduced pressure and the product purified by cc (DCM:EtOAc 5:1) using dry-load technique, followed by crystallization from a saturated DCM solution by adding heptane.

tert-Butyl (2-(5-(2-morpholinoethoxy)-1H-indole-2-carbonyl)-1H-indol-5-yl)carbamate (38a)

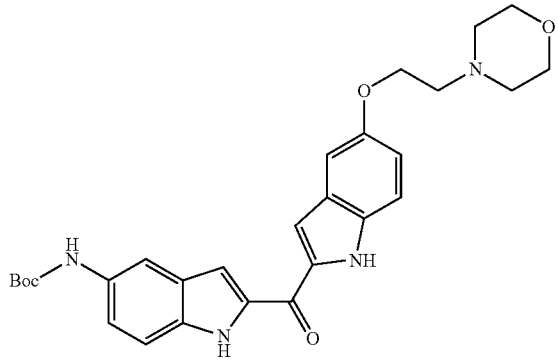 [SMILES: CC(C)(C)OC(=O)Nc1ccc2[nH]c(C(=O)c3cc4cc(OCCN5CCOCC5)ccc4[nH]3)cc2c1]

Preparation from 34e and 4-(2-chloroethyl)morpholine hydrochloride (37) as described above by use of K$_2$CO$_3$ (2.2 equiv.) instead of NaH as base. Reaction time 5d at 40° C. Yield 0.45 g (0.89 mmol, 35%) yellow solid after cc (SiO$_2$, DCM:EtOAc 1:1). $^1$H NMR (300 MHz, DMSO) δ 11.81 (s, 1H), 9.22 (s, 1H), 7.87 (s, 1H), 7.47 (s, 2H), 7.37 (dt, J=16.9, 8.5 Hz, 3H), 7.19 (d, J=2.3 Hz, 1H), 6.97 (dd, J=8.9, 2.4 Hz, 1H), 4.11 (t, J=5.8 Hz, 2H), 3.69-3.47 (m, 4H), 3.32 (s, 2H), 2.73 (t, J=5.7 Hz, 2H), 1.50 (s, 9H).

Methyl 6-((2-(5-((tert-butoxycarbonyl)amino)-1H-indole-2-carbonyl)-1H-indol-5-yl)oxy) hexanoate (38b)

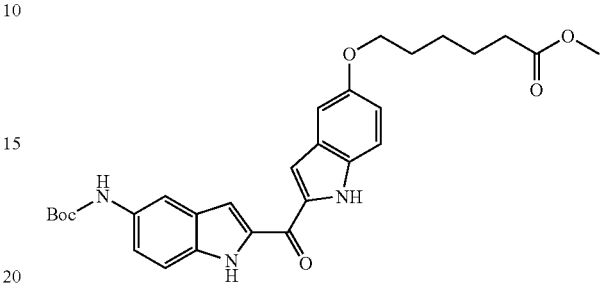

Preparation from 34e and methyl 6-bromohexanoate (38) as described above. Yield 0.62 g (1.2 mmol, 46%) yellow solid after cc (SiO$_2$, DCM:EtOAc 5:1). Mp. 67.4-68.2° C. IR (KBr): ν (cm$^{-1}$)=3363, 2933, 1719, 1527. $^1$H-NMR (300 MHz, DMSO-d$_6$): δ=12.18 (s, 1H, Indole-NH), 11.80 (s, 1H, Indole-NH), 9.22 (s, 1H, NH), 7.87 (s, 1H, ArH), 7.47 (s, 2H, ArH), 7.43-7.32 (m, 3H, ArH), 7.16 (d, J=2.3 Hz, 1H, ArH), 6.96 (dd, J=8.9, 2.4 Hz, 1H, ArH), 3.98 (t, J=6.4 Hz, 2H, CH$_2$), 3.59 (s, 3H, O—CH$_3$), 3.32 (s, 2H, CH$_2$), 2.42-2.26 (m, 2H, CH$_2$), 1.81-1.67 (m, 2H, CH$_2$), 1.60 (dd, J=15.0, 7.5 Hz, 2H, CH$_2$), 1.50 (s, 9H, (CH$_3$)$_3$). ESI-MS (120 eV) m/z (%): 520.0 (90) [MH+]. Anal. (C$_{29}$H$_{33}$N$_3$O$_6$): Calcd. C, 67.04, H, 6.40, N, 8.09. Found. C, 67.04, H, 6.67, N, 7.95.

6-((2-(5-(3-(5-(tert-butyl)isoxazol-3-yl)ureido)-1H-indole-2-carbonyl)-1H-indol-5-yl)oxy)hexanoic acid (41b)

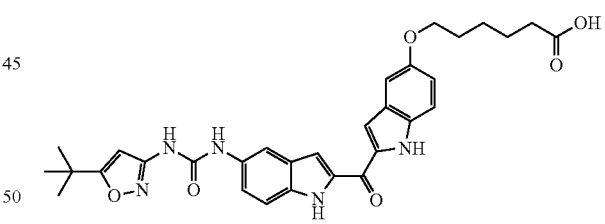

Compound 40b (0.29 g, 0.5 mmol) was dissolved in a mixture of THF:MeOH:H$_2$O 2:1:1 (50.0 mL), LiOH (1.2 equiv.) was added and the solution and stirred at 40° C. overnight. The organic solvents were removed under reduced pressure till the product precipitates. The product was removed by filtration, washed with a small amount of water and dried. Yield 0.19 g (0.33 mmol, 65%) colorless solid. Mp. 200.0° C. (Decomposition). IR (KBr): ν (cm$^1$)=3283, 2966, 1703, 1527. $^1$H-NMR (300 MHz, DMSO-d$_6$): δ=11.78 (s, 2H, Indol-NH), 11.45 (s, 1H, NH), 10.87 (s, 1H, NH), 7.90 (s, 1H, ArH), 7.57 (d, J=8.9 Hz, 1H, ArH), 7.46 (d, J=3.1 Hz, 2H, ArH), 7.38 (dd, J=8.9, 3.6 Hz, 2H, ArH), 7.16 (d, J=2.0 Hz, 1H, ArH), 6.96 (dd, J=8.9, 2.2 Hz, 1H, ArH), 6.53 (s, 1H, Isoxazol-CH), 3.98 (t, J=6.3 Hz, 2H, CH$_2$), 2.14-2.09 (m, 2H, CH$_2$), 1.88-1.69 (m, 2H, CH$_2$), 1.60 (dd, J=14.5, 7.1 Hz, 2H, CH₂), 1.49 (d, J=7.0 Hz, 2H, CH₂), 1.29 (s, 9H, (CH₃)₃). ESI-MS (120 eV) m/z (%): 572.1 (100) [MH⁺]. Anal. (C₃₁H₃₃N₅O₆×0.5H₂O): Calcd. C, 64.13, H, 5.90, N, 12.06. Found. C, 64.15, H, 5.79, N, 11.99.

1-(2-(5-(2-Aminoethoxy)-1H-indol-2-carbonyl)-1H-indole-5-yl)-3-(5-(tert-butyl)isoxazol-3-yl)urea (44)

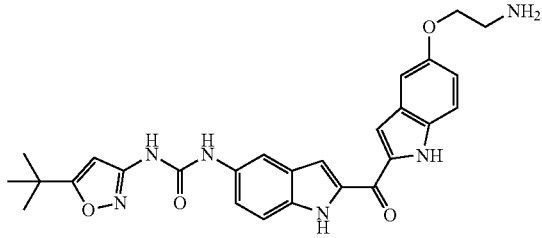 [SMILES: CC(C)(C)c1cc(NC(=O)Nc2ccc3[nH]c(C(=O)c4cc5cc(OCCN)ccc5[nH]4)cc3c2)no1]

Preparation of 44 analogous lit. (Arndt, Chan et al. 2011) from 34e and tert-Butyl-(2-hydroxyethyl)carbamate (42) by use of 1.5 equiv. PPh₃ and 1.5 equiv. DIAD in THF solution at 50° C. Cleavage of the tert-butylcarbamate was performed by use of 4 M HCl in Dioxane at 40° C. in the following as described (Arndt, Chan et al. 2011). Yield 0.35 g (0.70 mmol, 39%) after cc (SiO₂, EtOAc:MeOH 2:3 (v/v)+1% [w] NH₃) and crystallization from THF/light petrol over 2 steps. ¹H-NMR (300 MHz, DMSO-d₆): δ=11.85 (s, 2H, Indole-NH), 9.03 (s, 1H, NH), 7.93 (d, J=1.7 Hz, 1H, ArH), 7.51 (s, 1H, ArH), 7.49 (s, 1H, ArH), 7.42 (t, J=9.1 Hz, 2H, ArH), 7.31 (dd, J=8.9, 2.0 Hz, 1H, ArH), 7.18 (d, J=2.3 Hz, 1H, ArH), 6.99 (dd, J=8.9, 2.4 Hz, 1H, ArH), 6.52 (s, 1H, Isoxazole-CH), 4.03-3.86 (m, 2H, CH₂), 2.91 (t, J=5.6 Hz, 2H, CH₂), 1.30 (s, 9H, (CH₃)₃). ESI-MS (120 eV) m/z (%): 501.2 (100) [MH⁺]. HR-MS (120 eV) m/z: Calcd. 501.2245. Found. 501.2248 (C₂₇H₂₉N₆O₄) [MH⁺].

(E)-N-(2-((2-(5-(3-(5-tert-butyl-isoxazol-3-yl)ureido)-1H-indol-2-carbonyl)-1H-indol-5-yl)oxy)ethyl)-3-(dimethylamino)acrylamid (45)

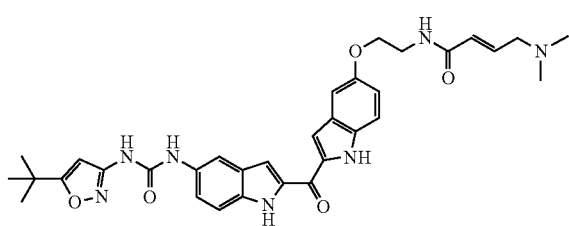 [SMILES: CN(C)C/C=C/C(=O)NCCOc1ccc2[nH]c(C(=O)c3cc4cc(NC(=O)Nc5cc(C(C)(C)C)on5)ccc4[nH]3)cc2c1]

To a solution of 44 (0.20 g, 0.40 mmol) in DMF (15.0 mL), BOP (1.1 equiv.), ((E)-4-(dimethylamino)but-2-enic acid hydrochloride) (0.44 mmol) and 3.5 equiv. NEt₃ were added at room temperature. The mixture was stirred at room temperature overnight, poured into water, the precipitating product removed by filtration, washed with water, dried, and crystallized from CH₂Cl₂. Yield 0.13 g (0.21 mmol, 53%) beige solid. Mp. 184.0-184.9° C. IR (KBr): ν (cm⁻¹)=3458, 1668, 1568. ¹H-NMR (300 MHz, DMSO-d₆): δ=11.90 (s, 1H, NH), 11.86 (s, 1H, NH), 9.51 (s, 1H, NH), 8.86 (s, 1H, NH), 8.36 (d, J=5.4 Hz, 1H, NH), 7.92 (s, 1H, ArH), 7.51 (s, 1H, ArH), 7.48 (s, 1H, ArH), 7.43 (t, J=8.3 Hz, 2H, ArH), 7.29 (dd, J=8.9, 1.8 Hz, 1H, ArH), 7.21 (d, J=1.9 Hz, 1H, ArH), 6.99 (dd, J=8.9, 2.2 Hz, 1H, ArH), 6.59 (dt, J=15.5, 6.3 Hz, 1H, CH), 6.52 (s, 1H, Isoxazol-CH), 6.13 (d, J=15.5 Hz, 1H, CH), 4.05 (t, J=5.3 Hz, 2H, CH₂), 3.54 (d, J=5.4 Hz, 2H, CH₂), 3.11 (d, J=6.0 Hz, 2H, CH₂), 2.20 (d, J=11.2 Hz, 6H, N—(CH₃)₂), 1.30 (s, 9H, (CH₃)₃). ESI-MS (120 eV) m/z (%): 612.3 (100) [MH⁺]. HR-MS (120 eV) m/z: Ber. 612.2929. Gef. 612.2938 (C₃₃H₃₇N₇O₅) [MH⁺].

2-(5-(3-(5-(tert-Butyl)isoxazol-3-yl)ureido)benzo-furan-2-carbonyl)-1H-indol-5-yl [1,4'-bipiperidine]-1'-carboxylate (48a)

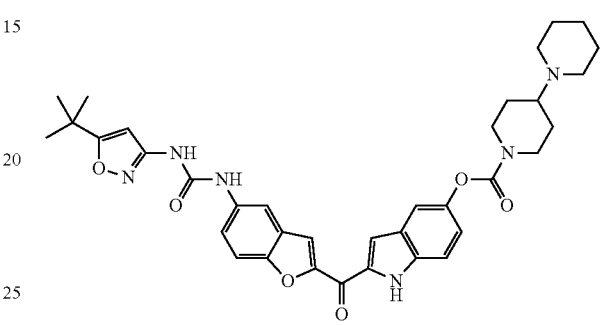

100 mg 28 (0.22 mmol) were dissolved in a mixture of CH₂Cl₂ (5 ml) and Pyridine (5 ml). After addition of 86 mg 1,4'-bipiperidine-1'-carbonyl chloride (0.37 mmol) in 0.5 ml CH₂Cl₂ the solution was stirred at room temperature for 16 h. The mixture was diluted with 40 ml of CH₂Cl₂, washed with water and dried with Na₂SO₄. The solvent was removed under reduced pressure. The residue was suspended in ether and the beige crystals were filtered off, washed with ether and dried.

Yield: 140 mg, 0.21 mmol (95%). Mp: 261.3-262.9° C. IR (KBr): ν (cm⁻¹)=3279, 2931, 1711. ¹H NMR (DMSO-d₆) δ 12.15 (d, J=2.3 Hz, 1H), 9.58 (s, 1H), 9.01 (s, 1H), 8.09 (d, J=2.2 Hz, 1H), 8.01 (s, 1H), 7.81-7.74 (m, 2H), 7.54-7.45 (m, 3H), 7.10 (dd, J=8.9, 2.3 Hz, 1H), 6.53 (s, 1H), 4.30-3.99 (m, 2H), 3.09-2.78 (m, 2H), 2.49-2.41 (m, 4H), 1.86-1.70 (m, 2H), 1.56-1.33 (m, 9H), 1.31 (s, 9H). ESI-MS (70 eV) m/z (%): 653.3 (100) [MH+].

2-(5-(3-(5-(tert-butyl)isoxazol-3-yl)ureido)benzo-furan-2-carbonyl)-1H-indol-5-yl [1,4'-bipiperidine]-1'-carboxylate Hydrochloride (48b)

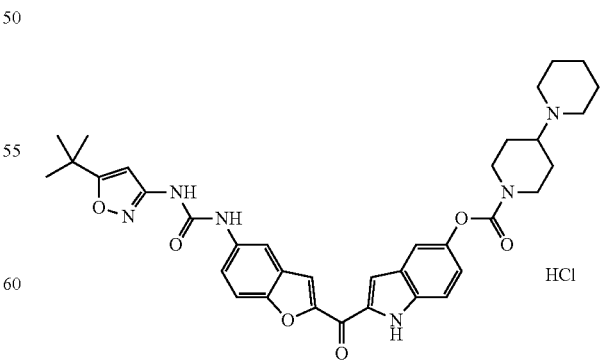

70 mg 48a (0.11 mmol) were dissolved in a mixture of CH₂Cl₂ (10 ml) and methanol (10 ml). After addition of 0.5 ml 6N HCl in 2-propanol the mixture was stirred for 2 h at room temperature. The solvent was removed under reduced pressure and the residue was dried.

Yield: 72 mg, 0.10 mmol (90%). Mp: 173° C. (decomp.). IR (KBr): ν (cm−1)=3370, 3280, 2961, 1700. $^1$H NMR (DMSO-d6) δ 12.17 (d, J=2.3 Hz, 1H), 10.27 (s, 1H), 9.73 (s, 1H), 9.47 (s, 1H), 8.10 (d, J=2.2 Hz, 1H), 8.02 (s, 1H), 7.87-7.69 (m, 2H), 7.58-7.43 (m, 3H), 7.12 (dd, J=8.8, 2.3 Hz, 1H), 6.54 (s, 1H), 4.44-4.07 (m, 2H), 3.51-3.33 (m, 4H), 3.10-2.83 (m, 4H), 2.24-2.06 (m, 2H), 1.91-1.64 (m, 7H), 1.31 (s, 9H).

Enhancement of Solubility by Transformation to a Carbamate Prodrug

Figure 3:
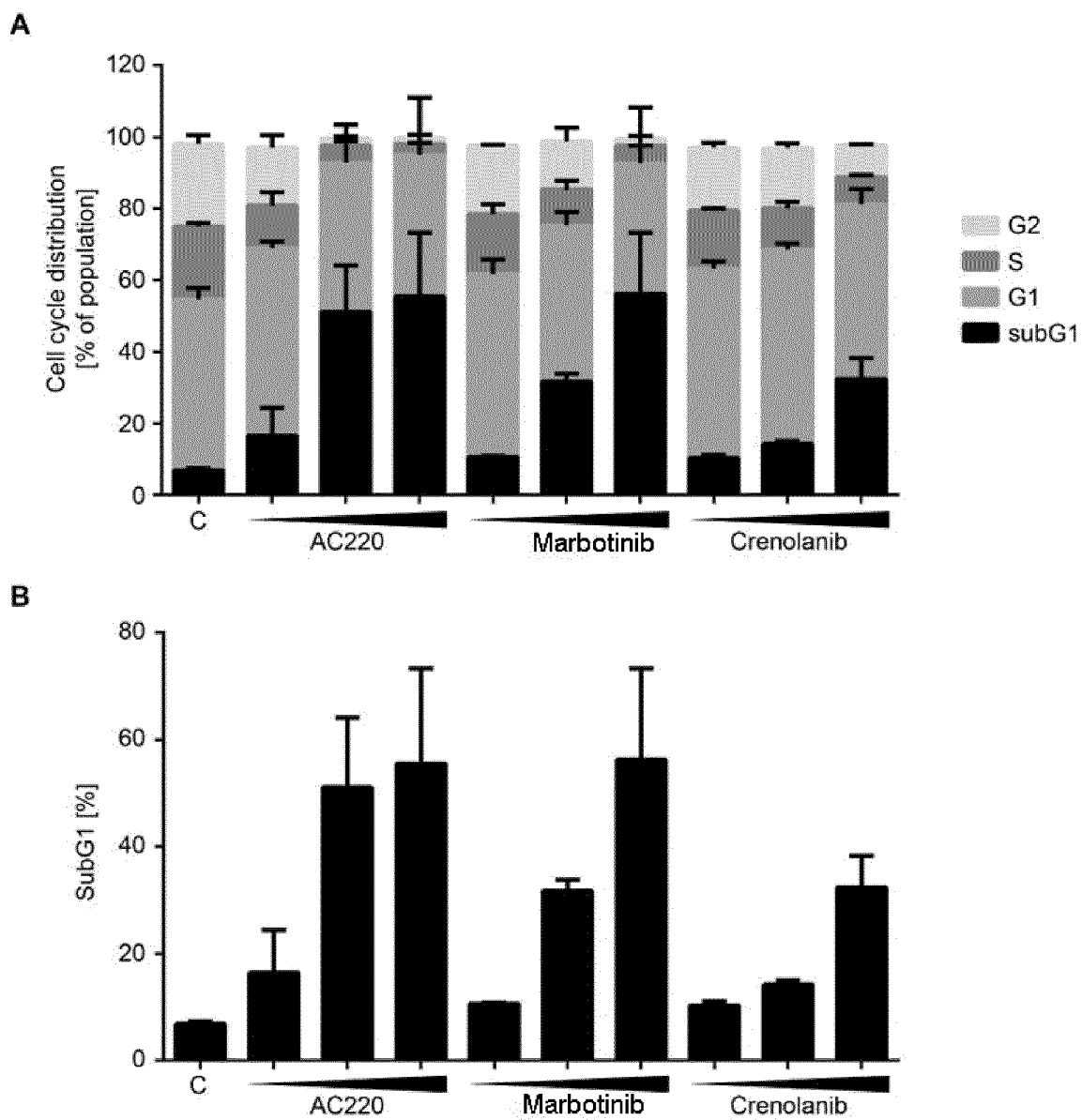
FIG. 3: The human FLT3-ITD positive cell line MV4-11 was stimulated with different FLT3i (2 nM, 5 nM or 10 nM) for 48 h (n=2). Cells were stained with PI and measured by flow cytometry. Data were analyzed with FACS Diva software (Version 7.0, BD Biosciences GmbH, Heidelberg, Germany).

Further experiments show that Marbotinib has a similar potency as AC220 against MV4-11 cells. Crenolanib is less potent than AC220 (as previously known from current literature (Lipka, Heidel et al. 2008; Zimmerman, Turner et al. 2013; Galanis, Ma et al. 2014; Smith, Lasater et al. 2014) and, notably, less potent than Marbotinib (FIG. 3).

The results indicate that the inventive fusion of the basic 5-substituted bisaroylmethanone-structure with the 1-(5-(tert-butyl)isoxazol-3-yl)urea residue is highly active against FLT3-ITD-positive AML cells.

To exclude cell specific effects the human AML cell line MOLM-13 was tested with different doses of Marbotinib for

| Structure | Solubility |
|---|---|
| 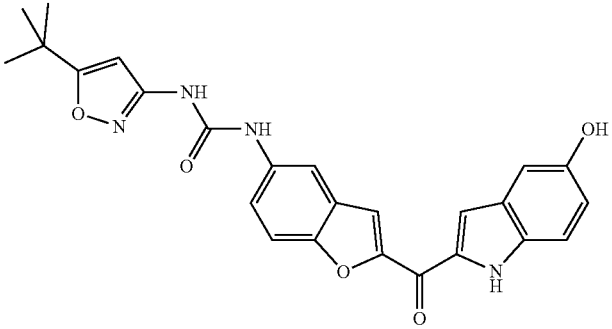 28 | 1 mg/ml< |
| 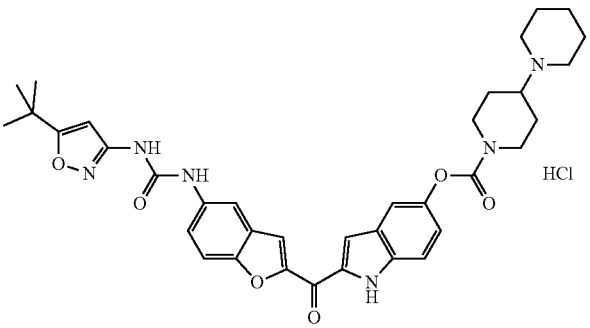 48a | 3-4 mg/ml |

Figure 2A:
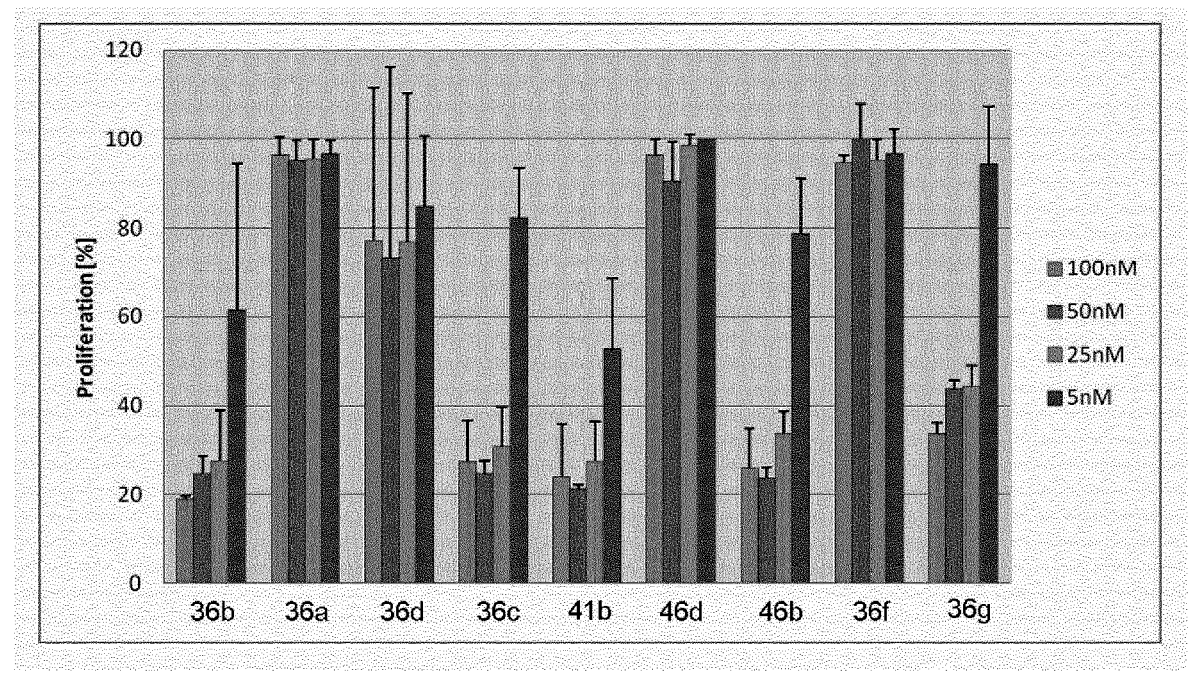
FIGS. 2A and 2B: Proliferation assay of selected compounds of the novel set of TKi against human AML cells (MV4-11 cells).

Example—Biological Evaluation—Biological Activity of the Novel TKi Against Human AML Cells The pharmacological properties of the novel compounds against FLT3-ITD-positive human MV4-11 cells (FIG. 2A+B) were evaluated. Most of the investigated compounds show promising effects in this assay. The most potent compounds exhibited a bisaroylmethanone-skeleton substituted with the tert-butyl-isoxazol-urea platform in position 5 of one of the selected aroyl-systems, either indole or benzofurane.

Figure 2B:
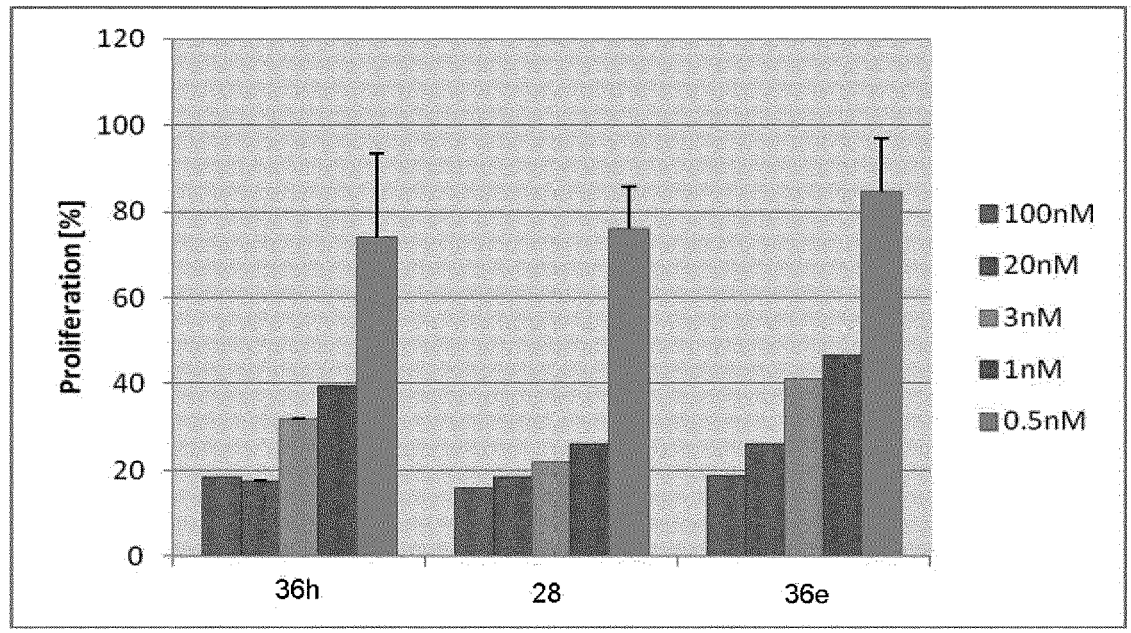

Within this group of agents Marbotinib was most potent. When given once at only 1 nM it inhibited the proliferation of MV4-11 cells by nearly 80% (FIG. 2B). Therefore, this compound was analyzed in further detail.

Analysis of Cell Cycle Distribution and Apoptosis after FLT3i Treatment

The synthesized set of FLT3 inhibitors (FLT3i) was tested in the human FLT3-ITD expressing AML cell line MV4-11 (Buchwald, Pietschmann et al. 2010).

The leading structure Marbotinib is among the substances that increase the subG1 fraction most strongly (FIG. 3).

48 h. MOLM-13 cells carries a FLT3-ITD but in contrast to MV4-11 cells only one allele is mutated. The cells show similar effects like MV4-11 cells (FIG. 4) analyzing cell cycle distribution.

Figure 4:
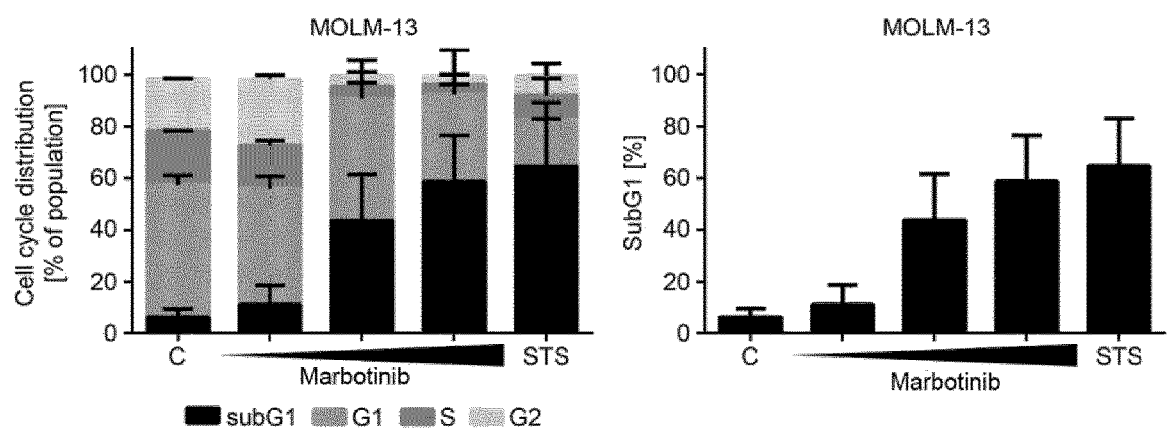
FIG. 4: The human FLT3-ITD positive cell line MOLM-13 was stimulated with 2 nM, 5 nM and 10 nM Marbotinib or 5 μM Staurosporine (STS) for 48 h (n=2). The cells were stained with PI and analyzed by flow cytometry.

Additional experiments were performed to ensure the specificity of Marbotinib. Other human blood cell lines that carry no FLT3-ITD were stimulated with Marbotinib and analyzed. K562 cells derived from a patient with chronic myeloid leukemia. These cells are precursors from erythrocytes and carry a mutation of the tyrosine kinase BCR-ABL. The NB4 cells derived from a patient with acute promyelocytic leukemia and carry a mutation in the PML-RARA fusion protein (Noack, Mahendrarajah et al. 2016). Peripheral blood mononuclear cells (PBMCs) were freshly isolated from whole blood samples and used immediately for experiments. K562, NB4 and PBMCs were stimulated with different concentrations of Marbotinib for 48 h and cell cycle distribution was analyzed by flow cytometry. Marbotinib selectively leads to an increase of subG1 fraction only in FLT3-ITD positive cell lines (FIG. 3 and FIG. 4). Cell lines or cells that carry no FLT3-ITD are not affected by Marbotinib (FIG. 5).

Figure 5:
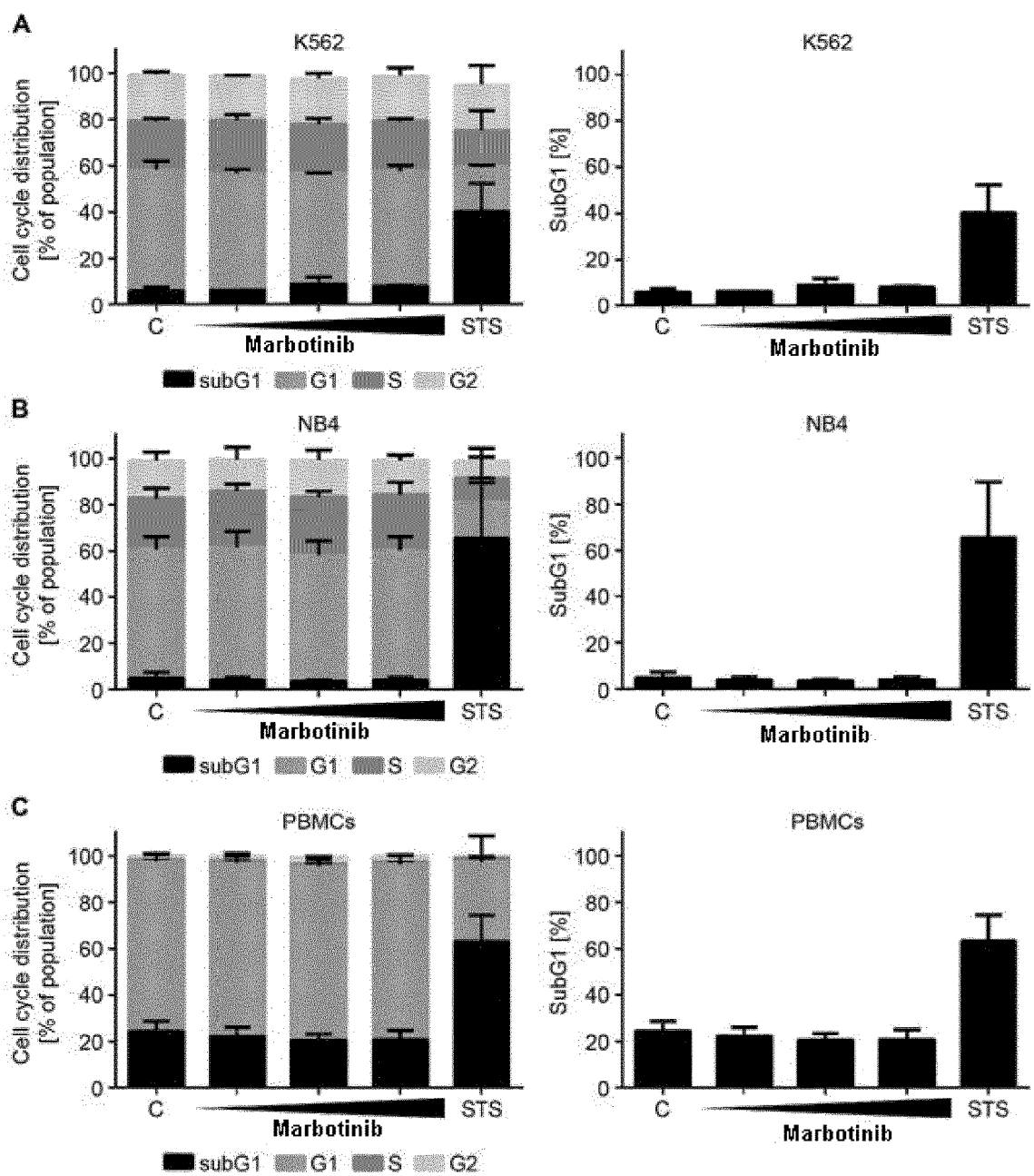
FIG. 5: Diverse human cell lines or cells were treated with different concentrations of Marbotinib (2 nM, 5 nM or 10 nM) or 5 μM STS for 48 h. Cells were harvested and stained with PI; cell cycle distribution were analyzed by flow cytometry. Cell cycle distribution and changes of subG1 fraction are illustrated. A) K562 cell line; B) NB4 cell line; C) PBMCs; n=2

The results show a clear increase in subG1 fraction in FLT3-ITD positive cell lines and no effects in other cell lines or cells (FIG. 3-5). The subG1 fraction is only a hint for apoptosis therefore we stained MV4-11 cells and PBMCs for AnnexinV FITC/PI. This staining allows a differentiation between early apoptosis and late apoptosis. MV4-11 cells show a clear induction of apoptosis after treating these cells with Marbotinib. PBMCs show no changes in basal apoptosis and confirm the results of PI staining (FIG. 6). The results show a strong specificity of Marbotinib and a high potency like AC220. Treating FLT3-ITD positive cells with only 5 nM Marbotinib leads to a strong induction of apoptosis without affecting other cells or cell lines tested here.

As described in the introduction there are several mutations next to ITDs that lead to reduce efficiency or to resistance against FLT3i treatment. The murine pro B cell line Ba/F3 and different mutant forms were analyzed. The proliferation of Ba/F3 wild type (WT) cells is dependent of interleukin-3 (IL-3). These cells were cultivated with 10% WEHI. The effect of Marbotinib in comparison to AC220 and Crenolanib in the following Ba/F3 mutants was investigated:

Ba/F3 WT (IL-3 dependent)
Ba/F3 ITD N676K
Ba/F3 D835Y
Ba/F3 ITD D835Y
Ba/F3 D835Y N676K Based on the results from previous experiments, 5 nM of AC220, Crenolanib and Marbotinib were used and the cells were stimulated for 48 h. The WT and the different mutants were stained with PI and cell cycle distribution was analyzed by flow cytometry. AC220 leads to a clear increase of subG1 fraction in Ba/F3 ITD N676K and D835Y mutants, Crenolanib shows changes in cell cycle distribution in Ba/F3 D835Y and D835Y N676K mutants and with Marbotinib a strong increase of subG1 population in Ba/F3 ITD N676K, D835Y and D835Y N676K mutants was detected. A slight increase can be observed also in the highly resistant mutant Ba/F3 ITD D835Y. In nearly all tested mutants Marbotinib leads to an increase of subG1 fraction via a concentration of 5 nM (FIGS. 7.1 and 7.2).

Determination of FLT3-ITD Signaling after FLT3i Treatment

Figure 8:
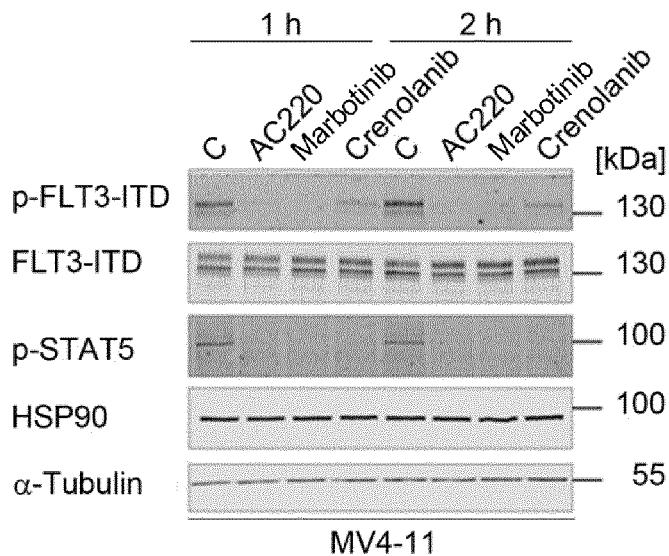
FIG. 8: MV4-11 cells were treated with 5 nM of different FLT3i for 1 h or 2 h. Cell lysates were analyzed by Western blot. α-Tubulin and HSP90 were used as loading control. (n=3)
Figure 9:
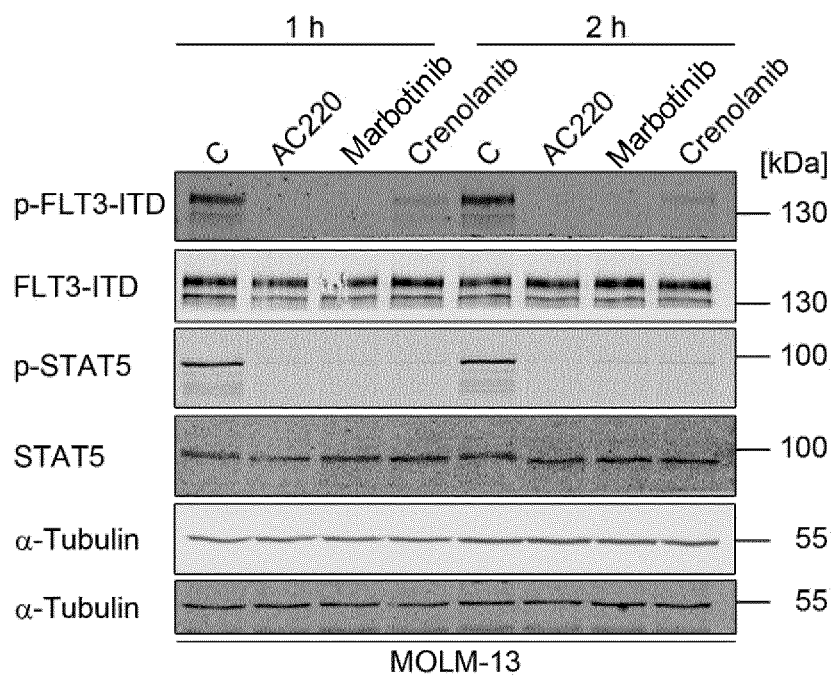
FIG. 9: Human MOLM-13 cells were treated with 5 nM of different FLT3i for 1 h or 2 h. Whole cell lysates were analyzed by Western blot. α-Tubulin was used as loading control. (n=2)

To determine the specificity and potency of Marbotinib, the activity of FLT3-ITD was compared to AC220 and Crenolanib. MV4-11 or MOLM-13 cells were stimulated as indicated and whole cell lysate were prepared and analyzed by immunoblot (FIG. 8-9). A technique was as described in Beyer et al. (Beyer, Kiweler et al. 2017) was used. The specific antibodies against FLT3-ITD, phosphorylated FLT3-ITD (p-FLT3-ITD), and its downstream target signal transducer and activator of transcription-5 (STAT5) (Choudhary, Mueller-Tidow et al. 2005; Kosan, Ginter et al. 2013) allow determining the specificity and potency of Marbotinib. 5 nM Marbotinib clearly reduces p-FLT3-ITD after 1 h in MV4-11 and MOLM-13 cells. Accordingly, a clear reduction of p-STAT5 is detectable (FIG. 8-9).

As different mutations of the FLT3 kinase may lead to a reduction or to a complete loss of efficiency, murine Ba/F3 WT cells were stimulated in a comparative experiment using the mentioned mutant forms with different FLT3i in equimolar doses of 5 nM for 2 h. Whole cell lysates are prepared and analyzed by Western Blot. AC220 leads to a clear reduction of p-FLT3 of the ITD N676K mutant. This result confirmed the observation of flow cytometry. The treatment of the cells with Crenolanib for 2 h did not result in strong effects. The mutants with the strongest changes in cell cycle distribution (Ba/F3 D835Y and Ba/F3 D835Y N676K) only show a weak signal in Western blot in phosphorylation status of STAT5 and FLT3.

Figure 10:
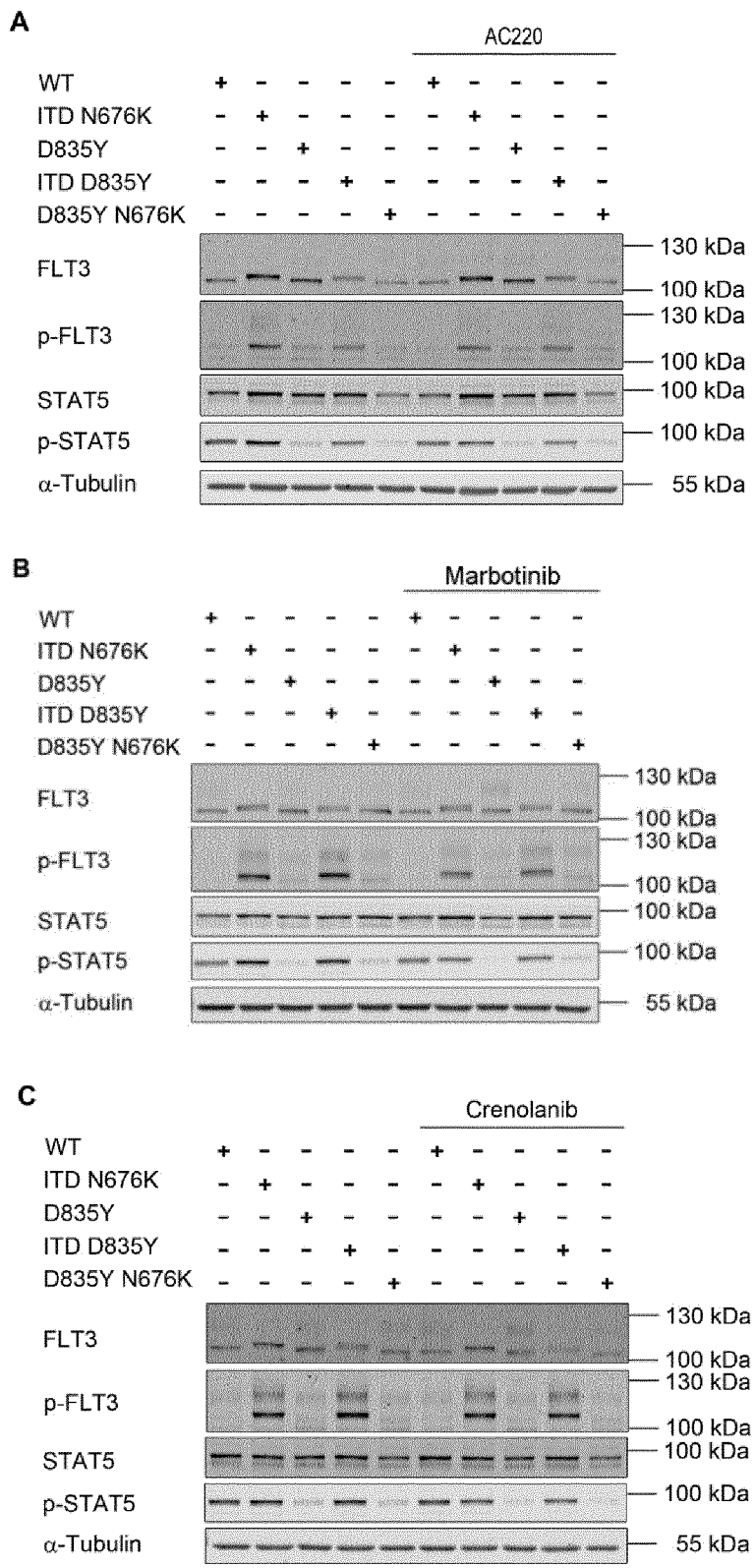
FIG. 10: Murine Ba/F3 WT vs. mutant cells were treated with equimolar doses of Marbotinib in comparison to AC220 and Crenolanib (5 nM) for 2 h. Whole cell lysates were prepared and analyzed by Western blot (n=2) α-Tubulin was used as loading control. A) AC220; B) Marbotinib; C) Crenolanib FIG. 11. Immunoblot analyses of protein lysates derived from MV4;11 xenotransplantation models. Tumor nodes were explanted 24 hours upon start of treatment with indicated concentrations of PKC412 or Marbotinib and protein lysates were prepared. Immunoblot analysis was performed using anti-pSTAT5A/B (Tyr694/699), anti-(total)-t-STAT5 and anti-phospho-FLT3 (Tyr591) antibodies. Anti-GAPDH staining was used as loading control. For each condition 2 tumor samples were blotted.

Marbotinib leads to a strong reduction of the signal of p-FLT3 and p-STAT5 from the Ba/F3 ITD N676K mutant, confirming the results from flow cytometry, and interestingly leads to a strong reduction of also the signal of the very resistant Ba/F3 ITD D835Y mutant (FIG. 7.2 and FIG. 10).

In conclusion the new FLT3 inhibitor Marbotinib shows high efficiency, comparable to AC220 in MV4-11 and MOLM-13 cells in flow cytometry and Western blot. When analyzing Ba/F3 WT and mutant cells, Marbotinib leads to a clear induction of subG1 fraction in more mutant forms than AC220 or Crenolanib. Also in Western blots Marbotinib is more potent in the described mutant cells.

Evaluation in a Mouse Model

Figure 11:
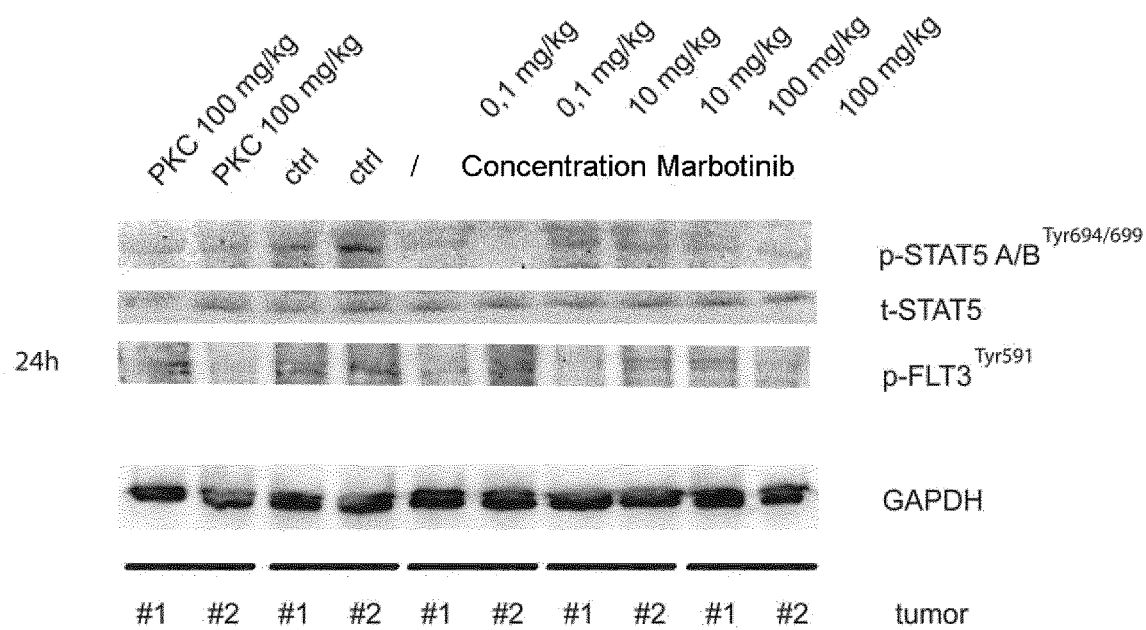

To test the tolerability and in vivo efficacy of Marbotinib, xenotransplantation assays using NOD/SCID/γc (NSG) mice were performed. In a first experiment, $10 \times 10^6$ MV4-11 cells were transplanted subcutaneously into recipient mice (day 0). Tumor growth was observed at day 5 and treatment with Marbotinib (0.1 mg/kg, 10 mg/kg, 100 mg/kg) was initiated at day 11 by oral administration or intraperitoneal injections. As a control, a cohort of transplanted mice were treated with the FLT3-inhibitor PKC412 (100 mg/kg). To investigate target efficacy, mice were sacrificed 24 hours after beginning of treatment. Upon preparation of single cell suspension derived from subcutaneous tumor nodes (90-100 cm$^3$), protein lysates were extracted immunoblot analyses performed. As shown in FIG. 11, one can observe inhibition of FLT3-phosphorylation and STAT5-phosphorylation, the most important downstream mediator of aberrant FLT3 signaling.

Figure 12:
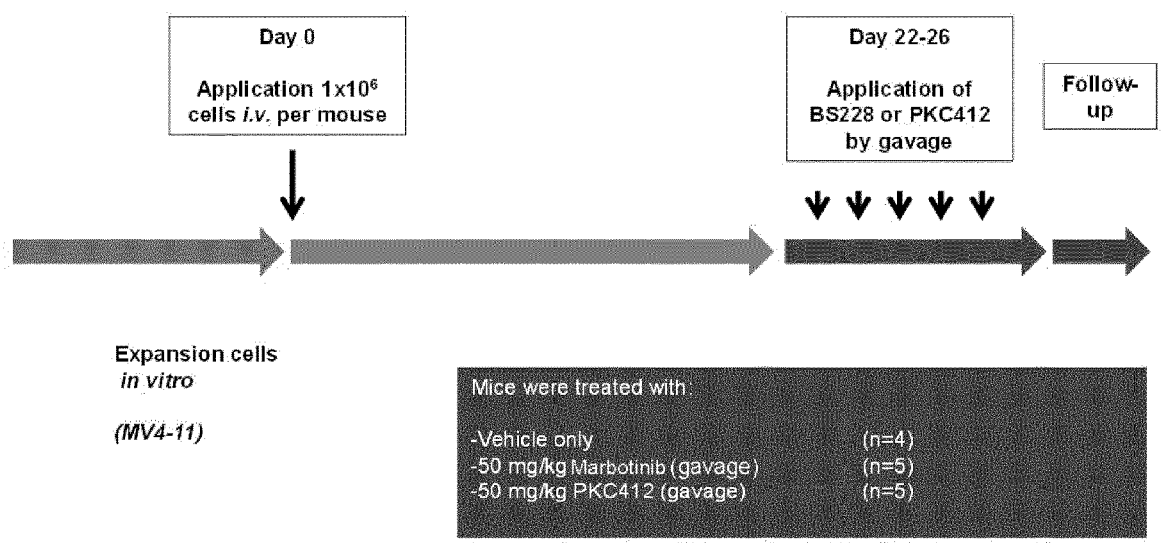
FIG. 12: Description of experimental set-up and treatment strategy.

Altogether, 18 mice were treated with different concentrations of Marbotinib either by oral administration (N=14) or intraperitoneal injections (N=4). Mice were sacrificed either 4 hours (N=9) or 24 hours (N=9) after start of treatment. Of note, no toxic effects were observed in analyzed organs such as liver, lung, heart and kidneys, indicating good tolerability at doses up to 100 mg/kg. To examine long-term efficacy, recipient mice were transplanted with $1 \times 10^6$ MV4;11 cells by tail vein injections. The treatment plan is shown in FIG. 12.

Figure 13:
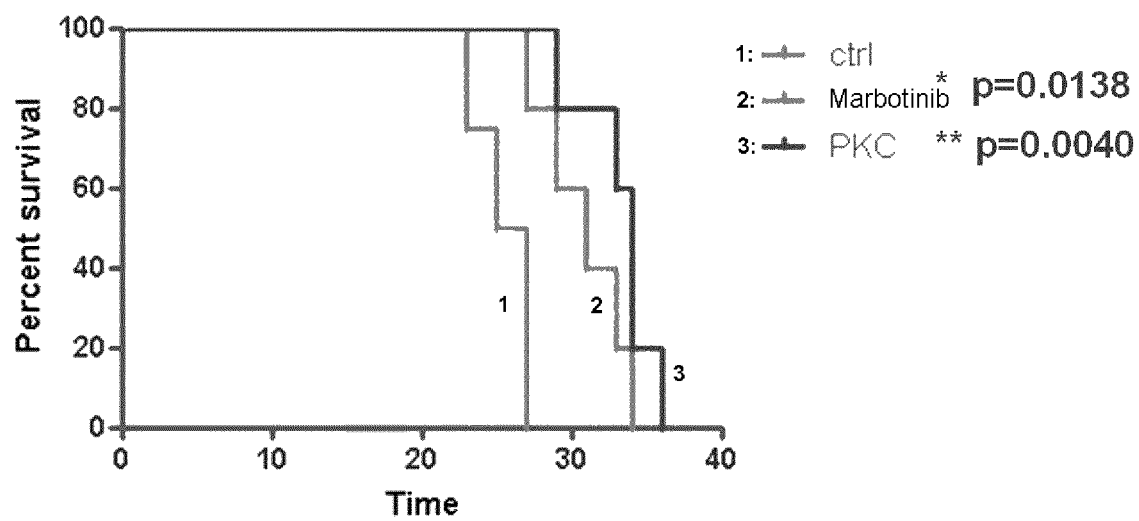
FIG. 13: Kaplan-Meier survival curves. Recipient mice were transplanted with 1×106 MV4;11 cells by intravenous tail vein injection. Treatment with PKC412, (N=5; 50 mg/kg bodyweight, qd) Marbotinib (N=5; 50 mg/kg bodyweight, qd) or vehicle control (N=4) was started at day 22 post transplantation by oral gavage. Mice were treated for 5 days followed by an observation period and moribund mice were sacrificed. Differences in survival were analyzed by log-rank analyses.

Treatment with Marbotinib resulted significant prolonged overall survival compared to vehicle treated mice (FIG. 13). No difference was seen between Marbotinib and PKC412.

Comparison with AC220 a) Vitality Assay

MV4-11 cells were treated with FLT3-inhibitors at different concentrations (1 nM, 5 nM, 10 nM, 100 nM) for 48 h. Viability staining was performed using life cell staining with DAPI. Samples were analysed using flow cytometry via FACS Canto; N=3.

Figure 14:
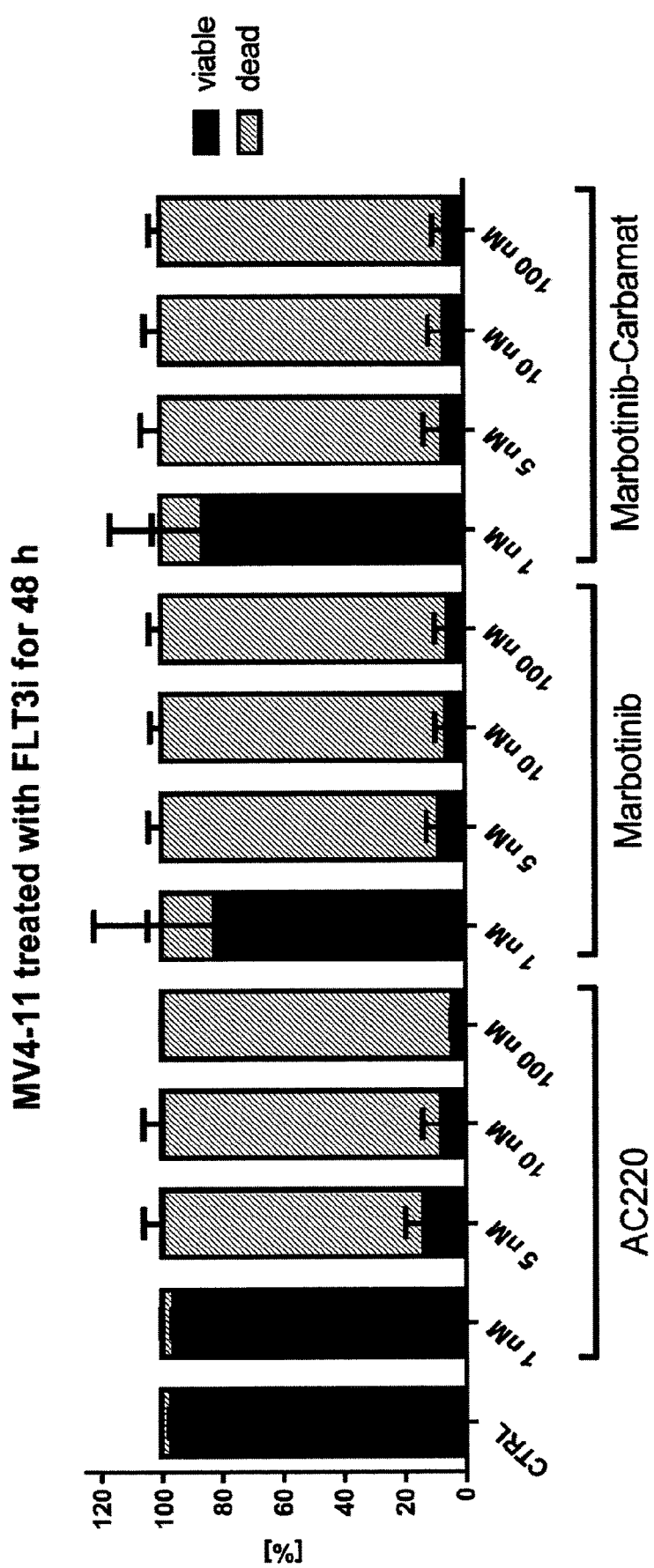
FIG. 14: Results of vitality assay in which MV4-11 cells were exposed to FLT3-inhibitors Marbotinib, Marbotinib Carbamate and ACC220, at different concentrations, and cell viability staining was performed.

The results are shown in FIG. 14. It can be seen that both Marbotinib and Marbotinib-Carbamate were more effective than compound AC220, especially at lower concentrations, i.e. 1 nM, 5 nM and 10 nM.

b) Dephosphorylation of FLT3-ITD and Effects on Downstream Targets Over Time.

Figure 15:
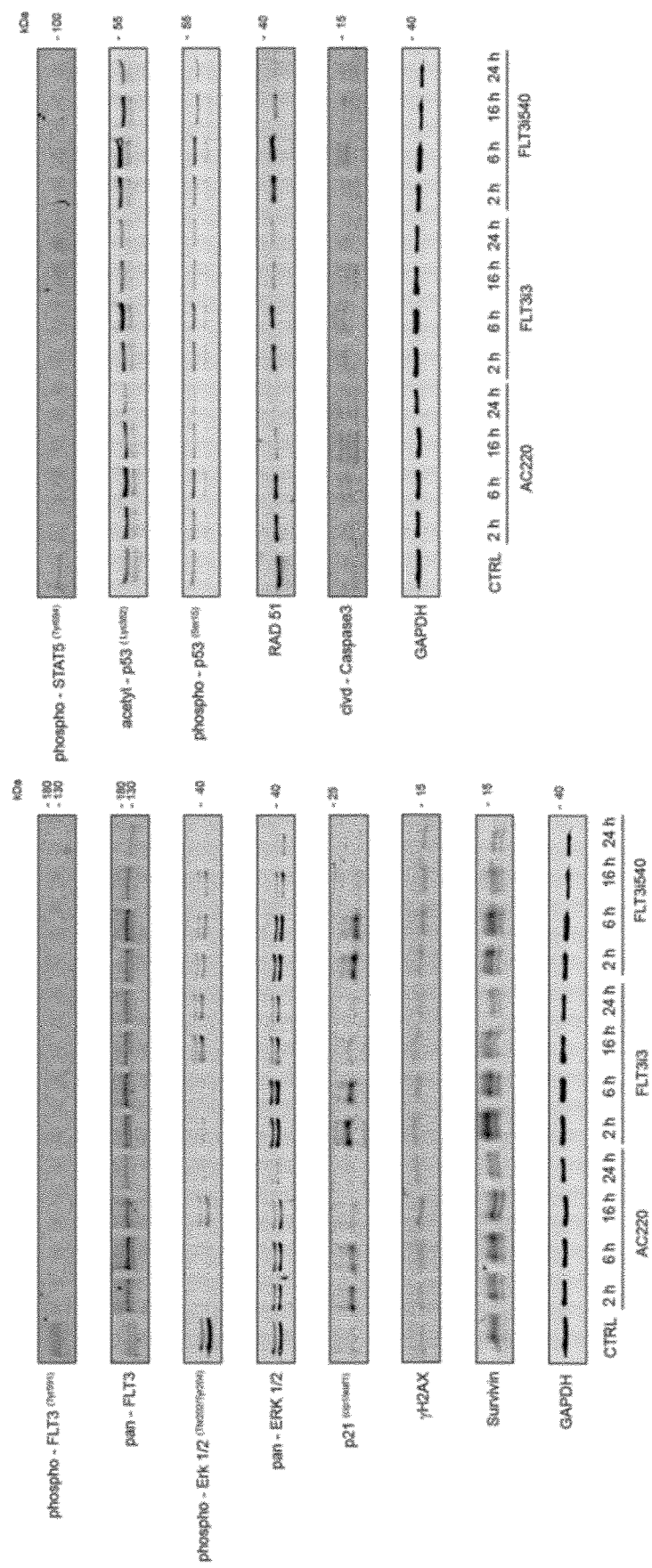
FIG. 15: Results of dephosphorylation assay in which MV4-11 cells were exposed to FLT3-inhibitors Marbotinib, Marbotinib Carbamate and AC220, at different timepoints, and thereafter whole cell lysates are analysed via SDS- PAGE and Western blot; Marbotinib is indicated as "FLT3i3", and Marbotinib Carbamate as "FLT3i540".

The results are shown in FIG. 15. MV4-11 cells were treated with 5 nM FLT3 inhibitors for different time points (2 h, 6 h, 16 h, 24 h). Whole cell lysates were used for SDS-Page and Western blot. The blots show dephosporylation of FLT3-ITD and some of its downstream targets, cell cycle regulators, and DNA damage regulators after treatment with FLT3-inhibitors over time. GAPDH was used as loading control. Control is indicated as CTRL. Marbotinib is indicated as FLT3i3 and Marbotinib-Carbamat is indicated as FLT3i540.

Thus, Marbotinib and Marbotinib-Carbamat effectively block FLT3-ITD and its associated signaling cascades.

c) In-Vivo Testing in Mouse Model

Figure 16:
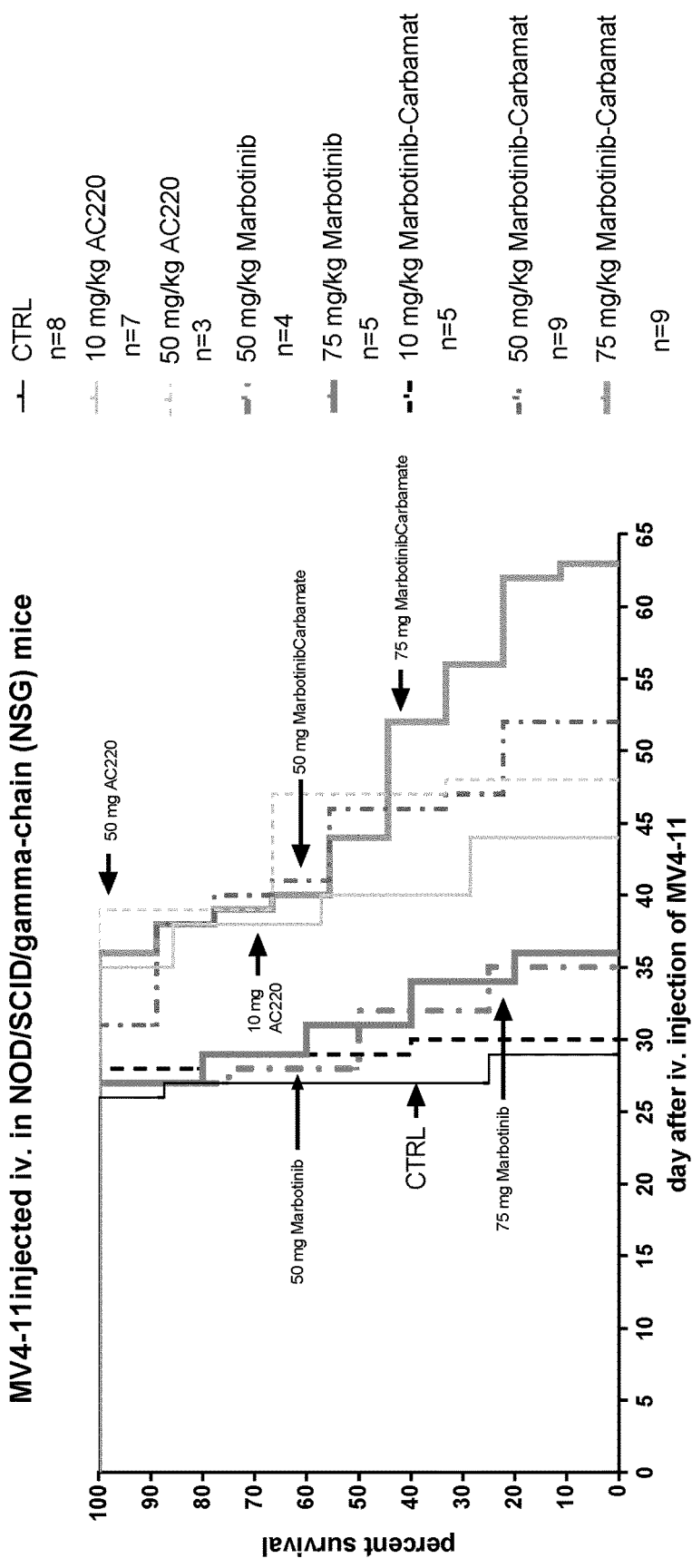
FIG. 16: Effect of Marbotinib, Marbotinib Carbamate and AC220 on different FLT3 mutations.

NOD/SCID/gamma-chain (NSG) mice were injected intravenously with $1\times10^6$ MV4-11 cells. From day 14 to day 18 after injection mice were treated with either FLT3-inhibitor (AC220, Marbotinib, Marbotinib-Carbamat) or vehicle (40% Captisol®) once per day using gavage; Marbotinib-Carbamat dissolved in double-distilled water. Mice were killed after developing symptoms of leukemia. The results are shown in FIG. 16. Shown is the percent survival of mice, which is clearly increased in the group treated with Marbotinib-Carbamat. AC220 cannot be dosed higher than 50 mg/kg while Marbotinib-Carbamat can be dosed up to 75 mg/kg.

d) Comparison of Efficacy of Marbotinib with AC220 on Different FLT3 Mutations

The efficacy of Marbotinib as an exemplary representative of the compounds according to the present invention was compared with AC220 on different FLT3 mutations. More specifically, Ba/F3 cells were incubated for 72 hours with a concentration series of the corresponding compound, i.e. Marbotinib or AC220, and the cell number was determined by means of trypan blue staining (N=3). $IC_{50}$ values were calculated by means of the Prism Graphpad software. The results are shown in the following table 2 below. As can be seen, Marbotinib always had a better efficacy (i.e. lower $IC_{50}$ value) in comparison with AC220 with all the different FLT3 mutations tested.

TABLE 2

Comparison of the $IC_{50}$ values and the activity-ratio of Marbotinib vs. 7 (AC220) in Ba/F3 cells.

| Ba/F3-cell-line/ FLT3 mutation | Marbotinib $IC_{50}$ [nM] | 7 (AC220) $IC_{50}$ [nM] | Ratio of activity |
| --- | --- | --- | --- |
| D835Y | 1.14 ± 0.853 | 6.56 ± 0.342 | 5.8 |
| D835YN676K | 17.53 ± 0.900 | 39.32 ± 0.504 | 2.3 |
| ITD | 2.06 ± 0.346 | 7.59 ± 0.789 | 3.7 |
| ITD D835Y | 17.93 ± 0.914 | 136.4 ± 0.992 | 7.8 |
| ITD N676K | 16.51 ± 0.973 | 19.63 ± 0.940 | 1.2 |
| WT | 2.95 ± 0.852 | 3.56 ± 0.326 | 1.2 |

In summary, our preliminary data indicate good tolerability, on-target efficacy and beneficial long-term survival effects compared to untreated controls.

REFERENCES

Abu-Duhier, F. M., A. C. Goodeve, et al. (2001). "Identification of novel FLT-3 Asp835 mutations in adult acute myeloid leukaemia." *Br. J. Haematol.* 113(4): 983-988.

Andaloussi, M., E. Moreau, et al. (2007). "A convenient synthesis of linear pyridinoimidazo[1,2-a]pyridine and pyrroloimidazo[1,2-a]pyridine cores." *Tetrahedron Lett.* 48(47): 8392-8395.

Arndt, J., T. Chan, et al. (2011). Preparation of heterocyclic compounds useful as PDK1 inhibitors, Biogen Idec Ma Inc., USA; Sunesis Pharmaceuticals, Inc. 370 pp.

Berenstein, R. (2015). "Class III Receptor Tyrosine Kinases in Acute Leukemia—Biological Functions and Modern Laboratory Analysis." *Biomark Insights* 10(Suppl. 3): 1-14.

Berthel, S. J., L. Chen, et al. (2011). Azaindole derivatives as glucokinase activators and their preparation and use in the treatment of metabolic disorders, Hoffmann-La Roche Inc., USA. 108 pp.

Beyer, M., N. Kiweler, et al. (2017). "How to Distinguish Between the Activity of HDAC1-3 and HDAC6 with Western Blot." *Methods Mol Biol* 1510: 355-364.

Bhagwat, S., Q. Chao, et al. (2007). Preparation of imidazolothiazole compounds for treatment of proliferative diseases or autoimmune diseases, Ambit Biosciences Corporation, USA. 138 pp.

Buchwald, M., K. Pietschmann, et al. (2010). "Ubiquitin conjugase UBCH8 targets active FMS-like tyrosine kinase 3 for proteasomal degradation." *Leukemia* 24(8): 1412-1421.

Chao, Q., K. G. Sprankle, et al. (2009). "Identification of N-(5-tert-Butyl-isoxazol-3-yl)-N'-{4-[7-(2-morpholin-4-yl-ethoxy)imidazo[2,1-b][1,3]benzothiazol-2-yl] phenyl}urea Dihydrochloride (AC220), a Uniquely Potent, Selective, and Efficacious FMS-Like Tyrosine Kinase-3 (FLT3) Inhibitor." *J. Med. Chem.* 52(23): 7808-7816.

Choudhary, C., C. Mueller-Tidow, et al. (2005). "Signal transduction of oncogenic Flt3." *Int. J. Hematol.* 82(2.): 93-99.

Dumas, J., U. Khire, et al. (2012). Preparation of substituted heterocyclic ureas as p38 kinase inhibitors, Bayer HealthCare LLC, USA. 70 pp., Division of U.S. Ser. No. 458,014.

Fathi, A. and M. Levis (2011). "FLT3 inhibitors: a story of the old and the new." *Curr. Opin. Hematol.* 18(2): 71-76.

Frohling, S., R. F. Schlenk, et al. (2002). "Prognostic significance of activating FLT3 mutations in younger adults (16 to 60 years) with acute myeloid leukemia and normal cytogenetics: A study of the AML study group Ulm." *Blood* 100(13): 4372-4380.

Galanis, A., H. Ma, et al. (2014). "Crenolanib is a potent inhibitor of FLT3 with activity against resistance-conferring point mutants." *Blood* 123(1): 94-100.

Giles, F. J., A. T. Stopeck, et al. (2003). "SU5416, a small molecule tyrosine kinase receptor inhibitor, has biologic activity in patients with refractory acute myeloid leukemia or myelodysplastic syndromes." *Blood* 102(3): 795-801.

Gilliland, D. G. and J. D. Griffin (2002). "The roles of FLT3 in hematopoiesis and leukemia." *Blood* 100(5): 1532-1542.

Grunwald, M. R. and M. J. Levis (2015). "FLT3 Tyrosine Kinase Inhibition as a Paradigm for Targeted Drug Development in Acute Myeloid Leukemia." *Semin Hematol* 52(3): 193-199.

Heldin, C.-H. (1995). "Dimerization of cell surface receptors in signal transduction." *Cell* (Cambridge, Mass.) 80(2): 213-223.

Jiang, J. and G. W. Gribble (2002). "A direct lithiation route to 2-acyl-1-(phenylsulfonyl)indoles." *Synth. Commun.* 32(13): 2035-2040.

Johansson, G., P. Brandt, et al. (2005). Preparation of novel tetrahydrospiro{piperidine-4,4'-pyrrolo[3,2-c]pyridine} derivatives and novel indole derivatives useful in the treatment of 5-HT6 receptor-related disorders, Biovitrum Ab, Swed. 62 pp.

Kayser, S. and M. J. Levis (2014). "FLT3 tyrosine kinase inhibitors in acute myeloid leukemia: clinical implications and limitations." *Leuk. Lymphoma* 55(2): 243-255.

Kindler, T., D. B. Lipka, et al. (2010). "FLT3 as a therapeutic target in AML: still challenging after all these years." *Blood* 116(24): 5089-5102.

Knapper, S., A. K. Burnett, et al. (2006). "A phase 2 trial of the FLT3 inhibitor lestaurtinib (CEP701) as first-line treatment for older patients with acute myeloid leukemia not considered fit for intensive chemotherapy." *Blood* 108(10): 3262-3270.

Konig, H. and C. D. Santos (2015). "Signal transduction in Acute Myeloid Leukemia—Implications for Novel Therapeutic Concepts." *Curr Cancer Drug Targets* 15(9): 803-821.

Kosan, C., T. Ginter, et al. (2013). "STAT5 acetylation: Mechanisms and consequences for immunological control and leukemogenesis." *JAKSTAT* 2(4): e26102.

Lee, H. K., H. W. Kim, et al. (2014). "G-749, a novel FLT3 kinase inhibitor, can overcome drug resistance for the treatment of acute myeloid leukemia." *Blood* 123(14): 2209-2219.

Leung, A. Y. H., C. H. Man, et al. (2013). "FLT3 inhibition: a moving and evolving target in acute myeloid leukaemia." *Leukemia* 27(2.): 260-268.

Lewis, N. L., L. D. Lewis, et al. (2009). "Phase I study of the safety, tolerability, and pharmacokinetics of oral CP-868,596, a highly specific platelet-derived growth factor receptor tyrosine kinase inhibitor in patients with advanced cancers." *J. Clin. Oncol.* 27(31): 5262-5269.

Lin, W.-H., J. T. A. Hsu, et al. (2013). "Discovery of 3-phenyl-1H-5-pyrazolylamine derivatives containing a urea pharmacophore as potent and efficacious inhibitors of FMS-like tyrosine kinase-3 (FLT3)." *Bioorg. Med. Chem.* 21(11): 2856-2867.

Lipka, D., F. Heidel, et al. (2008). "Development of tyrosine kinase inhibitors for hematologic neoplasms. FLT3 and JAK2 as therapeutic targets." *Pharm Unserer Zeit* 37(5): 394-403.

Liu, Y. and N. S. Gray (2006). "Rational design of inhibitors that bind to inactive kinase conformations." *Nat Chem Biol* 2(7): 358-364.

Lougiakis, N., P. Marakos, et al. (2008). "Synthesis and antiviral activity evaluation of some novel acyclic C-nucleosides." *Chem. Pharm. Bull.* 56(12): 775-780.

Lyman, S. D. (1995). "Biology of flt3 ligand and receptor." *Int J Hematol* 62(2): 63-73.

Mahboobi, S., A. Sellmer, et al. (2007). "2-Aroylindoles and 2-Aroylbenzofurans with N-Hydroxyacrylamide Substructures as a Novel Series of Rationally Designed Histone Deacetylase Inhibitors." *J. Med. Chem.* 50(18): 4405-4418.

Mahboobi, S., S. Teller, et al. (2002). "Bis(1H-2-indolyl) methanones as a Novel Class of Inhibitors of the Platelet-Derived Growth Factor Receptor Kinase." *J. Med. Chem.* 45(5): 1002-1018.

Mahboobi, S., A. Uecker, et al. (2007). "Inhibition of FLT3 and PDGFR tyrosine kinase activity by bis(benzo[b]furan-2-yl)methanones." *Bioorg. Med. Chem.* 15(5): 2187-2197.

Mahboobi, S. et al. (2009), J. Med. Chem., 52(8): 2265-2279

Mahboobi, S., A. Uecker, et al. (2006). "Novel Bis(1H-indol-2-yl)methanones as Potent Inhibitors of FLT3 and Platelet-Derived Growth Factor Receptor Tyrosine Kinase." *J. Med. Chem.* 49(11): 3101-3115.

Meshinchi, S. and F. R. Appelbaum (2009). "Structural and Functional Alterations of FLT3 in Acute Myeloid Leukemia." *Clin. Cancer Res.* 15(13): 4263-4269.

Moore, A. S., A. Faisal, et al. (2012). "Selective FLT3 inhibition of FLT3-ITD+ acute myeloid leukaemia resulting in secondary D835Y mutation: a model for emerging clinical resistance patterns." *Leukemia* 26(7): 1462-1470.

Nakao, M., S. Yokota, et al. (1996). "Internal tandem duplication of the flt3 gene found in acute myeloid leukemia." *Leukemia* 10(12): 1911-1918.

Noack, K., N. Mahendrarajah, et al. (2016). "Analysis of the interplay between all-trans retinoic acid and histone deacetylase inhibitors in leukemic cells." *Arch. Toxicol.: Ahead of Print.*

Pelkey, E. T. and G. W. Gribble (1999). "Synthesis and reactions of N-protected 3-nitroindoles." *Synthesis* (7): 1117-1122.

Pratz, K. W., J. Cortes, et al. (2009). "A pharmacodynamic study of the FLT3 inhibitor KW-2449 yields insight into the basis for clinical response." *Blood* 113(17): 3938-3946.

Reindl, C., K. Bagrintseva, et al. (2006). "Point mutations in the juxtamembrane domain of FLT3 define a new class of activating mutations in AML." *Blood* 107(9): 3700-3707.

Schenone, S., C. Brullo, et al. (2008). "Small molecules ATP-competitive inhibitors of FLT3: a chemical overview." *Curr. Med. Chem.* 15(29): 3113-3132.

Schittenhelm, M. M., K. M. Kampa, et al. (2009). "The FLT3 inhibitor tandutinib (formerly MLN518) has sequence-independent synergistic effects with cytarabine and daunorubicin." *Cell Cycle* 8(16): 2621-2630.

Schmidt-Arras, D., S.-A. Bohmer, et al. (2009). "Anchoring of FLT3 in the endoplasmic reticulum alters signaling quality." *Blood* 113(15): 3568-3576.

Small, D., M. Levenstein, et al. (1994). "STK-1, the human homolog of Flk-2/Flt-3, is selectively expressed in CD34+ human bone marrow cells and is involved in the proliferation of early progenitor/stem cells." *Proc. Natl. Acad. Sci. U.S.A* 91(2): 459-463.

Smith, B. D., M. Levis, et al. (2004). "Single-agent CEP-701, a novel FLT3 inhibitor, shows biologic and clinical activity in patients with relapsed or refractory acute myeloid leukemia." *Blood* 103(10): 3669-3676.

Smith, C. C., E. A. Lasater, et al. (2014). "Crenolanib is a selective type I pan-FLT3 inhibitor." *Proc Natl Acad Sci USA* 111(14): 5319-5324.

Smith, C. C., K. Lin, et al. (2015). "FLT3 D835 mutations confer differential resistance to type II FLT3 inhibitors." *Leukemia* 29(12): 2390-2392.

Smith, C. C., N. P. Shah, et al. (2015). "Characterizing and Overriding the Structural Mechanism of the Quizartinib-Resistant FLT3 "Gatekeeper" F691L Mutation with PLX3397." *Cancer Discov* 5(6): 668-679.

Smith, C. C., Q. Wang, et al. (2012). "Validation of ITD mutations in FLT3 as a therapeutic target in human acute myeloid leukaemia." *Nature* 485(7397): 260-263.

Ustun, C., D. L. DeRemer, et al. (2009). "Investigational drugs targeting FLT3 for leukemia." *Expert Opin. Invest. Drugs* 18(10): 1445-1456.

Vanotti, E., F. Angelucci, et al. (2007). Pyrrolopyridines as kinase inhibitors and their preparation, pharmaceutical compositions and use in the treatment of diseases linked to disregulated cell proliferation or disregulated protein kinase, Pfizer Italia Sri, Italy. 118 pp.

Wagner, E., H.-J. Wittmann, et al. (2011). "Mepyramine-JNJ7777120-hybrid compounds show high affinity to hH1R, but low affinity to hH4R." *Bioorg. Med. Chem. Lett.* 21(21): 6274-6280.

Xu, J., E. H. Q. Ong, et al. (2014). "Design, synthesis and biological evaluation of FLT3 covalent inhibitors with a resorcylic acid core." *Bioorg. Med. Chem.* 22(23): 6625-6637.

Yamamoto, Y., H. Kiyoi, et al. (2001). "Activating mutation of D835 within the activation loop of FLT3 in human hematologic malignancies." *Blood* 97(8): 2434-2439.

Yokota, S., H. Kiyoi, et al. (1997). "Internal tandem duplication of the FLT3 gene is preferentially seen in acute myeloid leukemia and myelodysplastic syndrome among various hematological malignancies. A study on a large series of patients and cell lines." *Leukemia* 11(10): 1605-1609.

Zimmerman, E. I., D. C. Turner, et al. (2013). "Crenolanib is active against models of drug-resistant FLT3-ITD-positive acute myeloid leukemia." *Blood* 122(22): 3607-3615.

The invention claimed is:

1. A compound of formula (I):

(I)

wherein

A, B, D, F, G, H, I and J are independently from each other selected from CH and N;

E is selected from C and N;

k and m are independently from each other 0 or 1

X and Y are independently from each other selected from the group consisting of NH, O and S;

Z is selected from the group consisting of C=O, C=S and CHOH;

Q is selected from the group consisting of five or six membered aromatic or heteroaromatic systems;

$R_1$ is selected from the group consisting of H, and branched or unbranched alkyl; and $R_2$ is selected from the group consisting of H, alkyl residues, OH, alkoxy, an ester, a carbamate, alkoxy or an ester or a carbamate substituted with a group comprising amino, alkylamino, cyclic alkylamino, cyclic diaminoalky, heterocyclic alkylamino; 2-hydroxysuccinic acid, an amino acid, and pharmaceutically acceptable salts or solvates thereof.

2. The compound according to claim 1, wherein Q is isoxazole, or a salt or solvate thereof.

3. The compound according to claim 1, wherein $R_1$ is tert-Butyl, or a salt or solvate thereof.

4. The compound according to claim 1, wherein $R_2$ is OH, or an ester or a carbamate or a salt or solvate thereof.

5. The compound according to claim 1, wherein $R_2$ is an amino acid selected from the group consisting of lysine, proline, histidine, and arginine, and pharmaceutically acceptable salts or solvates thereof.

6. The compound according to claim 1, wherein X is O, or a salt or solvate thereof.

7. The compound according to claim 1, wherein Y is NH, or a salt or solvate thereof.

8. The compound according to claim 1, wherein Z is C=O, or a salt or solvate thereof.

9. The compound according to claim 1, wherein A and/or B is CH, or a salt or solvate thereof.

10. The compound according to claim 1 having formula III (III)

or a salt or solvate thereof.

11. The compound according to claim 1, wherein the salt is selected from the group of salts consisting of hydrochloride, sulfate, phosphate, mesylate, tosylate, formiate, and acetate, or in a case of $R_2$=OH, a salt of a respective phenolate comprising sodium, potassium, calcium, zinc or another suitable cation and its solvates.

12. A pharmaceutical composition comprising a compound of claim 1.

13. A method for treating a cancer, wherein said method comprises administering, to a patient in need of such treatment, a compound according to claim 1, wherein the cancer is leukemia, wherein, in said compound, k and m are 0, Z is C=O, X and Y are independently selected from NH or O; A, B, D, F, G, H, I, and J are independently CH, and E is C.

14. The method according to claim 13, wherein the patient is a patient that is also subjected to treatment with at least one pan- or isoform-selective HDAC inhibitor, or wherein the patient is subjected to a co-treatment with at least one transcription inhibitor.

15. A method for inhibiting FLT3 wherein said method comprises administering, to a patient in need of such inhibition, a compound according to claim 1, wherein, in said compound, k and m are 0, Z is C=O, X and Y are independently selected from NH or O; A, B, D, F, G, H, I, and J are independently CH, and E is C.

16. A method of generating/synthesizing a compound as defined in claim 1, wherein k is 0, said method comprising the steps:

i) acylation of 5-(benzyloxy)-1-(phenylsulfonyl)-1H-indole at position 2 to introduce a carbonyl group, ii) bromination in alpha position to said carbonyl group introduced by said acylation of step i) to obtain an intermediate compound, iii) Reaction of said intermediate compound obtained in step ii) with 2-hydroxy-5-nitrobenzaldehyde and ring closure mediated by a base, iv) cleavage of the phenylsulfony-protection group of the compound obtained in step iii) by a base, v) catalytic hydrogenolytic cleavage of the benzyloxy group of the compound obtained in step iv, and vi) reaction of the compound obtained in step v) with an aryl isocyanate;

or comprising the steps:

i) lithiation of 1-(phenylsulfonyl)-1H-indole at position 2 using t-BuLi to obtain an aryl-lithium intermediate, which is 1-(phenylsulfonyl)-1H-indole-2-yl-lithium, and reaction of the aryl-lithium intermediate with carbonyl chloride, ii) cleavage of the sulfonyl protecting group of the compound obtained in step i), iii) acidic cleavage of the tert-butoxycarbonyl protective group of the compound obtained in step ii), and
iv) reaction of the compound obtained in step iii) with an aryl isocyanate;

or comprising the steps:
i) reaction of 1-(5-(tert-butyl)isoxazol-3-yl)-3-(2-(5-hydroxy-1H-indole-2-carbonyl)benzofuran-5-yl)urea with 1,4'-bipiperidine-1'-carbonyl chloride in pyridine, or reaction of 1,4'-bipiperidine with 2-(5-(3-(5-(tert-butyl)isoxazol-3-ureido)benzofuran-2-carbonyl)-1H-indol-5-yl carbonochloridate in the presence of trimethylamine to obtain a carbamate compound; and
ii) transformation of said carbamate compound obtained in step i) to a pharmaceutically acceptable salt by treatment of said carbamate compound with an acid.

17. The method of claim 13, wherein the leukemia is acute myeloid leukemia (AML).

18. The method of claim 13, wherein the patient is a leukemia patient having a mutation in the FLT3 gene.

19. The method of claim 16, wherein said aryl isocyanate is 5-(tert-butyl)-3-isocyanatoisoxazole.

20. The method of claim 16, wherein said carbamate compound is 2-(5-{3-(5-(tert-butyl)isoxazol-3-yl)ureido)benzofuran-2-carbonyl)-1H-indol-5-yl[1,4'-bipiperidine]-1'-carboxylate.

21. The method of claim 16, wherein said treatment of said carbamate compound with an acid is a treatment with HCl.

22. The method of claim 16, said method comprising the steps:
i) acylation of 5-(benzyloxy)-1-(phenylsulfonyl)-1H-indole at position 2 of the 5-(benzyloxy)-1-(phenylsulfonyl)-1H-indole, thereby introducing a carbonyl group, to obtain 1-(5-benzyloxy-1-phenylsulfonyl-1H-indol-2-yl)ethan-1-one,
ii) bromination in alpha position to said carbonyl group introduced by said acylation of step i), thereby obtaining 1-(5-benzyloxy-1-phenyl sulfonyl-1H-indol-2-yl)-2-bromethan-1-one,
iii) reaction of said 1-(5-benzyloxy-1-phenylsulfonyl-1H-indol-2-yl)-2-bromethan-1-one obtained in step ii) with 2-hydroxy-5-nitrobenzaldehyde, and ring closure mediated by a base,
iv) cleavage of the phenylsulfony-protection group of the compound obtained in step iii) by a base,
v) catalytic hydrogenolytic cleavage of the benzyloxy group of the compound obtained in step iv, and
vi) reaction of the compound obtained in step v) with 5-(tert-butyl)-3-isocyanatoisoxazole;

or comprising the steps:
i) lithiation of a 1-(phenylsulfonyl)-1H-indole at position 2 of the 1-(phenylsulfonyl)-1H-indole using t-BuLi to obtain an aryl-lithium intermediate, which is 1-(phenylsulfonyl)-1H-indole-2-yl-lithium, and reaction of the aryl-lithium intermediate with carbonyl chloride,
ii) cleavage of the sulfonyl protecting group of the compound obtained in step i),
iii) acidic cleavage of the tert-butoxycarbonyl protective group of the compound obtained in step ii), and
iv) reaction of the compound obtained in step iii) with 5-(tert-butyl)-3-isocyanatoisoxazole;

or comprising the steps:
i) reaction of 1-(5-(tert-butyl)isoxazol-3-yl)-3-(2-(5-hydroxy-1H-indole-2-carbonyl)benzofuran-5-yl)urea with 1,4'-bipiperidine-1'-carbonyl chloride in pyridine, or reaction of 1,4'-bipiperidine with 2-(5-(3-(5-(tert-butyl)isoxazol-3-yl)ureido)benzofuran-2-carbonyl)-1H-indol-5-yl carbonochloridate, which can be obtained by treatment of 1-(5-(tert-butyl)isoxazol-3-yl)-3-(2-(5-hydroxy-1H-indole-2-carbonyl)benzofuran-5-yl)urea with phosgen in the presence of trimethylamine, thereby obtaining 2-(5-{3-(5-(tert-butyl)isoxazol-3-yl)ureido)benzofuran-2-carbonyl)-1H-indol-5-yl[1,4'-bipiperidine]-1'-carboxylate; and
ii) transformation of said 2-(5-{3-(5-(tert-butyl)isoxazol-3-yl)ureido)benzofuran-2-carbonyl)-1H-indol-5-yl[1,4'-bipiperidine]-1'-carboxylate obtained in step i) to a pharmaceutically acceptable salt by treatment of said 2-(5-{3-(5-(tert-butyl)isoxazol-3-yl)ureido)benzofuran-2-carbonyl)-1H-indol-5-yl[1,4'-bipiperidine]-1'-carboxylate with an acid.

* * * * *